United States Patent [19]

Kuhn et al.

[11] Patent Number: 5,646,147

[45] Date of Patent: Jul. 8, 1997

[54] ACARICIDAL, INSECTICIDAL AND NEMATICIDAL SUBSTITUTED (HETERO) ARYLALKYL KETONE OXIME O-ETHERS, PROCESSES FOR THEIR PREPARATION, AGENTS CONTAINING THEM, AND THEIR USE AS PESTICIDES

[75] Inventors: Birgit Kuhn, Hattersheim/Main; Gerhard Salbeck, deceased, late of Kriftel/Taunus, by Gisela Salbeck, heiress; Uwe Döller, Rodgau; Stefan Schnatterer, Hattersheim/Main, all of Germany; Hans-Herbert Schubert, Tokyo, Japan; Werner Knauf, Eppstein/Taunus, Germany; Anna Waltersdorfer, Frankfurt am Main, Germany; Manfred Kern, Lörzweiler, Germany

[73] Assignee: Hoechst Aktiengesellschaft, Frankfurt, Germany

[21] Appl. No.: 230,134

[22] Filed: Apr. 20, 1994

Related U.S. Application Data

[63] Continuation of Ser. No. 50,000, Apr. 20, 1993, abandoned.

[30] Foreign Application Priority Data

Apr. 22, 1992 [DE] Germany .................. 42 13 149.9

[51] Int. Cl.⁶ ............... C07D 401/00; C07D 401/02; C07D 403/00; C07D 403/02; A61K 31/50; A61K 31/495; A61K 31/44; A61K 31/38

[52] U.S. Cl. ............ 514/252; 549/366; 549/414; 549/426; 548/146; 548/205; 548/214; 548/235; 548/311.7; 548/312.1; 548/312.7; 548/315.4; 548/315.1; 548/314.7; 548/454; 548/485; 548/518; 548/526; 548/527; 548/566; 544/333; 544/335; 544/357; 544/359; 544/360; 514/396; 514/253; 514/374; 514/412; 514/414; 514/403; 514/255; 514/256; 514/378; 514/416; 514/444; 514/365; 514/332; 514/336; 514/338; 514/438; 514/461; 514/372; 514/341; 514/342; 514/343; 514/465; 514/640; 549/32; 549/58; 549/60; 549/65; 546/264; 546/268; 546/277; 546/278; 546/280; 546/281; 546/283; 546/284; 564/300; 564/256; 548/477

[58] Field of Search ............... 548/477, 146, 548/205, 214, 235, 311.7, 312.1, 312.7, 315.4, 315.1, 314.7, 454, 485, 518, 526, 527, 566; 564/300, 256; 514/640, 396, 252, 253, 374, 412, 414, 403, 255, 256, 378, 916, 444, 365, 332, 336, 338, 438, 461, 372, 341, 342, 343, 465; 546/264, 268, 277, 278, 280, 281, 283, 284; 544/333, 335, 357, 359, 360; 549/32, 58, 60, 65, 366, 414, 426

[56] References Cited

U.S. PATENT DOCUMENTS

| | | | |
|---|---|---|---|
| Re. 30,634 | 6/1981 | Henry | 424/327 |
| 4,079,149 | 3/1978 | Henry | 260/566 |
| 4,384,141 | 5/1983 | Schaefer et al. | 564/256 |
| 4,434,182 | 2/1984 | Cruickshank et al. | 424/327 |
| 4,474,815 | 10/1984 | Holan et al. | 424/327 |
| 4,753,960 | 6/1988 | Holan et al. | 514/464 |
| 5,194,662 | 3/1993 | Brand et al. | 560/35 |
| 5,231,106 | 7/1993 | Knutsen et al. | 514/340 |
| 5,376,680 | 12/1994 | Edwards et al. | 514/459 |

FOREIGN PATENT DOCUMENTS

| | | |
|---|---|---|
| 45234/79 | 11/1979 | Australia . |
| A 0 009 865 | 4/1980 | European Pat. Off. . |
| A 0 015 456 | 9/1980 | European Pat. Off. . |
| A 0 024 888 | 3/1981 | European Pat. Off. . |
| A 0 052 744 | 6/1982 | European Pat. Off. . |
| A 0 094 348 | 6/1983 | European Pat. Off. . |
| A 0 207 894 | 1/1987 | European Pat. Off. . |
| A 0 004 754 | 10/1993 | European Pat. Off. . |
| A 28 06 664 | 8/1978 | Germany . |
| A 30 05 899 | 9/1981 | Germany . |
| 2 025 407 | 1/1980 | United Kingdom . |
| WO8401772 | 5/1984 | WIPO . |
| WO86/00894 | 2/1986 | WIPO . |

OTHER PUBLICATIONS

Chemical Abstracts, vol. 109, No. 9, 1988, Abstract No. 73101n.
Chemical Abstracts, vol. 100, No. 15, 1984, Abstract No. 120606g.
Chemical Abstracts, vol. 94, No. 23, 1981, Abstract No. 191841y.
Chemical Abstracts, vol. 51, No. 2, 1957, Abstract No. 6603h.
Chemical Abstracts, vol. 109, No. 13, 1988, Abstract No. 106489a.
Chemical Abstracts, vol. 105, No. 15, 1986, Abstract No. 129392v.
Chemical Abstracts, vol. 102, No. 17, 1985, Abstract No. 144795.
Chemical Abstracts, vol. 101, No. 23, 1984, Abstract No. 210639v.
Chemical Abstracts, vol. 98, No. 17, 1983, Abstract No. 143124c.

(List continued on next page.)

Primary Examiner—Matthew V. Grumbling
Attorney, Agent, or Firm—Curtis, Morris & Safford, P.C.

[57] ABSTRACT

Acaricidal, insecticidal and nematicidal substituted (hetero) arylalkyl ketone oxime O-ethers, processes for their preparation, agents containing them, and their use as pesticides.

The invention relates to compounds of the formula

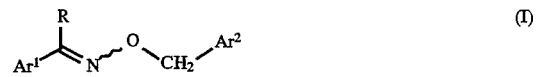

in which $Ar^1$ and $Ar^2$ are aryl or heteroaryl, each of which is optionally substituted, and R is an optionally substituted aliphatic or alicyclic radical, to processes for their preparation, and to agents containing these compounds, and to their use for controlling animal pests.

16 Claims, No Drawings

OTHER PUBLICATIONS

Chemical Abstracts, vol. 92, No. 23, 1980, Abstract No. 198103b.

Chemical Abstracts, vol. 92, No. 17, 1980, Abstract No. 141746j.

Chemical Abstracts, vol. 90, No. 23, 1979, Abstract No. 103840m.

Chemical Abstracts, vol. 101, No. 19, 1984, Abstract No. 165582h.

Chemical Abstracts, vol. 101, No. 15, 1984, Abstract No. 124827y.

Chemical Abstracts, vol. 99, No. 17, 1983, Abstract No. 135477a.

Chemical Abstracts, vol. 95, No. 3, 1981, Abstract No. 24511e.

Chemical Abstracts, vol. 104, No. 1, 1986, Abstract No. 2161t.

ACARICIDAL, INSECTICIDAL AND NEMATICIDAL SUBSTITUTED (HETERO) ARYLALKYL KETONE OXIME O-ETHERS, PROCESSES FOR THEIR PREPARATION, AGENTS CONTAINING THEM, AND THEIR USE AS PESTICIDES

This application is a continuation of application Ser. No. 08/050,000, filed Apr. 20, 1993, now abandoned.

The invention relates to novel substituted (hetero) arylalkyl ketone oxime O-ethers, processes for their preparation, agents containing them, and their use for controlling pests, in particular insects, Acarina and nematodes.

Some oxime ethers and their use as pesticides are known already [G. Holan et al., Recent Advances in the Chemistry of Insect Control II, p. 114 et seq. Cambridge 1990; T. G. Cullen et al., ACS Symp. Ser. 335 (1987) 173; M. J. Bull et al., Pestic. Sci. 11 (1980) 349; WO-A-84/01772].

Heteroaromatic oxime ethers which have insecticidal properties are known from EP-A-4,754 and EP-A-24,888. The activity of some of them, however, is insufficient.

Novel oxime O-ethers having advantageous pesticidal, in particular insecticidal, acaricidal and/or nematicidal properties, have been found.

The invention therefore relates to compounds of the formula I and salts thereof,

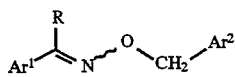

(I)

in which

I. $Ar^1$ and $Ar^2$ are identical or different and
a) $(C_6-C_{12})$-aryl or heteroaryl having up to 10 carbon atoms or
b) are defined as under I.a) end have up to 5 identical or different substituents selected from the group comprising
1. $(C_1-C_6)$-alkyl,
2. $(C_2-C_6)$-alkenyl,
3. $(C_2-C_6)$-alkynyl
4. $(C_3-C_8)$-cycloalkyl which is optionally substituted by up to 6 identical or different radicals selected from the group comprising halogen and $(C_1-C_4)$-alkyl,
5. halogen,
6. $(C_1-C_6)$-haloalkyl,
7. $(C_2-C_6)$-haloalkenyl,
8. $(C_2-C_6)$-haloalkynyl,
9. $(C_1-C_6)$-alkoxy-$(C_1-C_6)$-alkyl,
10. $(C_6-C_{12})$-aryl which is optionally up to trisubstituted by identical or different radicals selected from the group comprising $(C_1-C_6)$-alkyl, $(C_1-C_6)$-alkoxy, halogen, $(C_1-C_6)$-haloalkyl and $(C_1-C_6)$-haloalkoxy,
11. heteroaryl which has up to 10 carbon atoms and which is optionally substituted as described under I.b) 10.,
12. $(C_6-C_{12})$-aryl-$(C_1-C_4)$-alkyl which is optionally substituted in the aryl moiety as described under I.b) 10.,
13. heteroaryl-$(C_1-C_4)$-alkyl which has up to 10 carbon atoms in the heteroaryl moiety and is optionally substituted in this moiety as described under I.b) 10.,
14. $(C_1-C_4)$-alkoxy,
15. $(C_2-C_6)$-alkenyloxy,
16. $(C_2-C_6)$-alkynyloxy,
17. $(C_3-C_8)$-cycloalkyloxy which is optionally substituted as described under I.b) 4.,
18. $(C_1-C_6)$-alkoxy-$(C_1-C_4)$-alkoxy,
19. $(C_6-C_{12})$-aryloxy which is optionally substituted as described under I.b) 10.,
20. heteroaryloxy which has up to 10 carbon atoms and which is optionally substituted as described under I.b) 10.,
21. $(C_1-C_6)$-haloalkoxy,
22. $(C_2-C_6)$-haloalkenyloxy,
23. $(C_2-C_6)$-haloalkynyloxy,
24. —O—N=CR$'_2$ in which R' radicals are identical or different radicals selected from the group comprising hydrogen, $(C_1-C_6)$-alkyl, $(C_3-C8)$-cycloalkyl and $(C_6-C_{12})$-aryl,
25. $(C_1-C_6)$-alkylamino,
26. di-$(C_1-C_6)$-alkylamino,
27. $(C_3-C_8)$-cycloalkylamino which is optionally substituted as described under I.b) 4. ,
28. $(C_6-C_{12})$-arylamino which is optionally substituted as described under I.b) 10.,
29. heteroarylamino which has up to 10 carbon atoms and is optionally substituted as described under I.b) 10.,
30. $(C_1-C_6)$-alkylmercapto,
31. $(C_6-C_{12})$-arylmercapto,
32. heteroarylmercapto having up to 10 carbon atoms,
33. $(C_1-C_6)$-alkylsulfinyl,
34. $(C_6-C_{12})$-arylsulfinyl,
35. heteroarylsulfinyl having up to 10 carbon atoms,
36. $(C_1-C_6)$-alkylsulfonyl,
37. $(C_6-C_{12})$-arylsulfonyl,
38. heteroarylsulfonyl having up to 10 carbon atoms,
39. nitro,
40. cyano,
41. cyano-$(C_1-C_6)$-alkyl,
42. $(C_1-C_6)$-alkoxycarbonyl,
43. $(C_6-C_{12})$-aryloxycarbonyl and
44. heteroaryloxycarbonyl having up to 10 carbon atoms in the heteroaryl moiety, or
45. a) two of the substituents represent methylenedioxy,
b) the methylenedioxy group optionally being substituted by one or two identical or different radicals selected from the group comprising halogen and $(C_1-C_4)$-alkyl;

II. R is
a) $(C_1-C_6)$-alkyl,
b) $(C_2-C_6)$-alkenyl,
c) $(C_2-C_6)$-alkynyl or
d) $(C_3-C_8)$-cycloalkyl, or
e) as defined under II.a)–d) and has up to 3 identical or different substituents selected from the group comprising
1. halogen,
2. hydroxyl,
3. $(C_1-C_6)$-alkoxy,
4. $(C_1-C_6)$-alkylmercapto,
5. $(C_1-C_6)$-alkylsulfinyl,
6. $(C_1-C_6)$-alkylsulfonyl,
7. cyano,
8. nitro and
9. $(C_1-C_6)$-alkoxycarbonyl or
f) as defined under II.a)–d) and, if the number of hydrogen atoms $\geq 5$, some or all of these hydrogen atoms are replaced by halogen, the number of halogen atoms being $\geq 4$;

it also being possible for aryl and heteroaryl as defined in I.a) and b) to be partially hydrogenated and for one or two $CH_2$ groups in these aryl and heteroaryl moieties to be replaced by $CO_2$;

III. with the proviso that,
a) if R is methyl or substituted methyl which has 1, 2 or 3 identical or different radicals as defined under II.e) 1. or 3.–9., of which at least 1 radical is halogen, end if Ar¹ is aryl which is substituted as described under I.b) 2.–4., 7., 8., 11., 13., 15.–44. or 45.b), or optionally substituted heteroaryl, Ar² is as defined under I.a) or b),
b) if R is methyl or substituted methyl which has 1, 2 or 3 identical or different radicals as defined under II.e) 1. or 3.–9. of which at least one radical is halogen, and if Ar¹ is aryl which is substituted as described under I.b) 1., 5., 6., 9., 10., 12., 14. or 45a)., Ar² is as defined under I.a) or b), but is not 4-fluoro-3-phenoxyphenyl, 3-phenoxyphenyl, pentafluorophenyl or 2,6-dihalophenyl;
c) if R is (C₂–C₆)-alkyl or defined as under II.b)–f) and if Ar¹ is as defined under I.a) or is aryl as defined under I.b) or heteroaryl as defined under I.b) 1.–20. or 24.–45.), Ar² is as defined under I.a and b) but is not

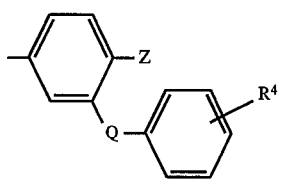

2,6-dihalophenyl, pentafluorophenyl,

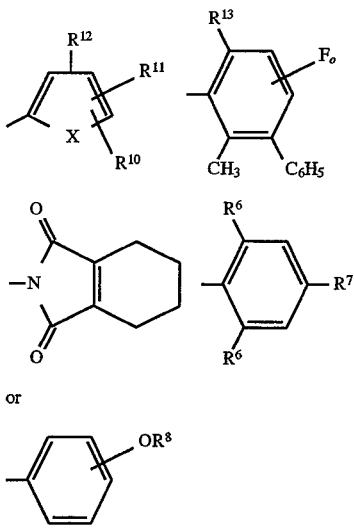

in which
Z is halogen or hydrogen,
Q is O, S, NH or CH₂,
R⁴ is halogen,
X is O or S,
R¹⁰, R¹¹ and R¹² are identical or different and are hydrogen or are as defined under I.b) 1.–45.,
R¹³ is hydrogen, fluorine or methyl,
o is 0, 1 or 2,
R⁶ is hydrogen, fluorine or alkyl,
R⁷ is halophenoxy, halobenzyl, O—CH₂—CH=CH₂, O—CH₂C≡CH; CH₂—CH=CH₂ or CH₂—C≡CH and
R⁸ is alkenyl or haloalkenyl;
d) if R is (C₂–C₆)-alkyl or as defined under II.b)–f) and if Ar¹ is heteroaryl as defined under I.b) 21.–23., Ar² can additionally be as defined under I.a and b);

e) if R is (C₂–C₆)-alkyl or as defined under II.b)–f) and if Ar¹ is heteroaryl as defined under I.a) or b), Ar² can additionally be pentafluorophenyl or

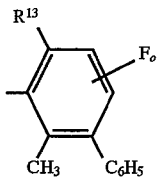

in which R¹³ and o are as defined above;
f) if R is substituted (C₂–C₆)-alkyl, (C₂–C₆)-alkenyl or (C₂–C₆)-alkynyl as defined under II.e) and if Ar¹ is aryl as defined under I.a)
or b), Ar² can additionally be

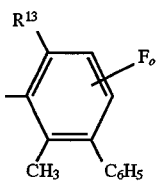

in which R¹³ and o are as defined above; and
g) if R is (C₂–C₆)-alkyl or as defined under II.b)–f) and if Ar¹ is substituted (C₆–C₁₂)-aryl as defined under I.b) 21., Ar² can additionally be pentafluorophenyl.

Alkyl, alkenyl and alkynyl can be straight-chain or branched. This applies also to radicals which are derived therefrom, such as alkoxy, alkylmercapto, haloalkyl and arylalkyl.

Haloalkyl, haloalkenyl and haloalkynyl are to be understood as meaning alkyl, alkenyl or alkynyl in which one, more than one or all hydrogen atoms are replaced by halogen. The same applies analogously to radicals derived therefrom, such as haloalkoxy, haloalkenyloxy or haloalkynyloxy.

Halogen is fluorine, chlorine, bromine or iodine, preferably fluorine, chlorine or bromine.

(C₆–C₁₂)-Aryl is preferably phenyl and radicals derived therefrom, such as naphthyl, biphenyl and indanyl.

A heteroaryl radical having up to 10 carbon atoms is preferably a mono- or bicyclic aryl radical in which at least one CH is replaced by N, and/or in which at least two adjacent CH groups are replaced by NH, O and/or S. Examples of such radicals are thienyl, benzothienyl, furyl, benzofuryl, pyrrolyl, imidazolyl, pyrazolyl, pyridyl, pyrazinyl, pyrimidinyl, pyridazinyl, indolyl, oxazolyl, isoxazolyl, thiazolyl and isothiazolyl.

If the compounds of the formula I can form salts, then the invention also relates to the salts thereof, in particular to the acid addition salts thereof. Acids which can be used for salt formation are inorganic acids such as hydrochloric acid, hydrobromic acid, nitric acid, sulfuric acid, phosphoric acid or organic acids such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Preferred compounds of the formula I are those in which
Ar¹ is phenyl, naphthyl, indanyl, benzofuryl, benzothienyl,

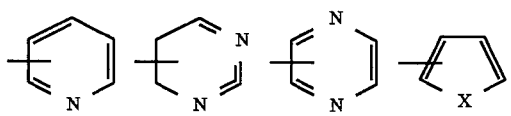

such as thienyl or furanyl or

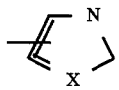

such as thiazolyl,
each of which is optionally substituted as defined above and in which X is O, S or $NR^3$ and $R^3$ is hydrogen,
- $(C_1-C_6)$-alkyl,
- $(C_2-C_6)$-alkenyl, preferably —$CH_2$—CH=$CH_2$,
- $(C_2-C_6)$-alkynyl, preferably —$CH_2$—C≡CH,
- $(C_3-C_8)$-cycloalkyl which is optionally substituted by up to 6 identical or different radicals selected from the group comprising halogen and $(C_1-C_4)$-alkyl,
- $(C_1-C_6)$-haloalkyl,
- $(C_2-C_6)$-haloalkenyl,
- $(C_2-C_6)$-haloalkynyl,
- $(C_1-C_6)$-alkoxy-$(C_1-C_6)$-alkyl,
- $(C_6-C_{12})$-aryl-$(C_1-C_4)$-alkyl,
- heteroaryl-$(C_1-C_4)$-alkyl having up to 10 carbon atoms in the heteroaryl moiety,
- cyano-$(C_1-C_6)$-alkyl,
- $(C_1-C_6)$-alkoxycarbonyl,
- $(C_6-C_{12})$-aryloxycarbonyl or
- heteroaryloxycarbonyl having up to 10 carbon atoms, in particular those compounds of the formula I in which $Ar^1$ is a radical of the formula

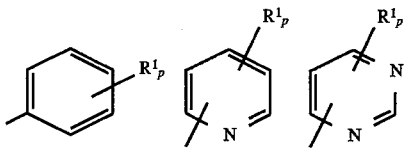

or

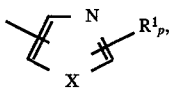

X is as defined above, p is an integer from 0 to 5, and $R^1$ radicals are identical or different and are halogen,
- $(C_1-C_6)$-alkyl,
- $(C_2-C_6)$-alkenyl,
- $(C_2-C_6)$-alkynyl,
- $(C_3-C_8)$-cycloalkyl which is optionally substituted by up to 6 identical or different radicals selected from the group comprising halogen and $(C_1-C_4)$-alkyl,
- $(C_1-C_6)$-haloalkyl,
- $(C_2-C_6)$-haloalkenyl,
- $(C_2-C_6)$-haloalkynyl,
- $(C_1-C_6)$-alkoxy-$(C_1-C_6)$-alkyl,
- $(C_6-C_{12})$-aryl which is optionally up to tri-substituted by identical or different radicals selected from the group comprising halogen, $(C_1-C_6)$-alkyl, $(C_1-C_6)$-alkoxy, $(C_1-C_6)$-haloalkyl, and $(C_1-C_6)$-haloalkoxy,
- heteroaryl which has up to 10 carbon atoms and which is optionally substituted like the abovementioned aryl,
- $(C_6-C_{12})$-aryl-$(C_1-C_4)$-alkyl which is optionally substituted in the aryl moiety like the abovementioned aryl,
- heteroaryl-$(C_1-C_6)$-alkyl which has up to 10 carbon atoms in the heteroaryl moiety and is optionally substituted in this moiety like the abovementioned aryl,
- $(C_1-C_6)$-alkoxy,
- $(C_2-C_6)$-alkenyloxy,
- $(C_2-C_6)$-alkynyloxy,
- $(C_3-C_8)$-cycloalkyloxy,
- $(C_1-C_6)$-alkoxy-$(C_1-C_6)$-alkoxy,
- $(C_6-C_{12})$-aryloxy which is optionally substituted like the abovementioned aryl,
- heteroaryloxy which has up to 10 carbon atoms and which is optionally substituted like the abovementioned aryl,
- $(C_1-C_6)$-haloalkoxy,
- $(C_2-C_6)$-haloalkenyloxy,
- $(C_2-C_6)$-haloalkynyloxy or
- —O—N=$CR'_2$ in which R' radicals are identical or different radicals selected from the group comprising hydrogen $(C_1-C_6)$-alkyl, $(C_3-C_8)$-cycloalkyl and $(C_6-C_{12})$-aryl, or
- two of the radicals $R^1$ are methylenedioxy which is optionally substituted as described under I.b) 45.b), in which $R^1$ is preferably
- $(C_1-C_6)$-alkyl,
- $(C_2-C_6)$-alkenyl,
- $(C_2-C_6)$-alkynyl,
- $C_3-C_8$)-cycloalkyl, halogen,
- $(C_1-C_6)$-haloalkyl,
- $(C_2-C_6)$-haloalkenyl,
- $(C_2-C_6)$-haloalkynyl,
- heteroaryl having up to 10 carbon atoms or $(C_6-C_{12})$-aryl, optionally substituted as described above,
- $(C_1-C_6)$-alkoxy,
- $(C_2-C_6)$-alkenyloxy,
- $(C_2-C_6)$-alkynyloxy,
- $(C_3-C_8)$-cycloalkyloxy,
- heteroaryloxy having up to 10 carbon atoms or $(C_6-C_{12})$-aryloxy, optionally substituted as described above,
- $(C_1-C_6)$-alkoxy-$(C_1-C_6)$-alkyl,
- $(C_1-C_6)$-alkoxy-$(C_1-C_6)$-alkoxy,
- $(C_1-C_6)$-haloalkoxy,
- $(C_2-C_6)$-haloalkenyloxy or
- $(C_2-C_6)$-haloalkynyloxy,
- or two of the radicals $R^1$ are methylenedioxy which is optionally substituted as described under I.b) 45. b), in which $R^1$ is, in particular, $(C_1-C_6)$-haloalkoxy such as $OCHF_2$, $OCF_3$, $OCF_2CF_2H$, $OCH_2CF_3$ or OCH $(CF_3)_2$, $(C_1-C_6)$-alkoxy, fluorine, chlorine, bromine, $(C_1-C_6)$-alkyl, $(C_2-C_6)$-haloalkenyloxy, $(C_2-C_6)$-haloalkynyloxy, $(C_1-C_6)$-haloalkyl, $(C_2-C_6)$-haloalkenyl or $(C_2-C_6)$-haloalkynyl.

The radicals $R^1$ which have been mentioned as being preferred are preferably in the 4-position of the phenyl

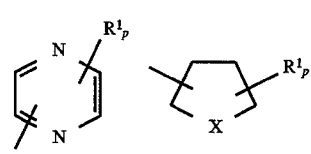

radical, in the corresponding position of a heteroaromatic six-membered ring or in an analogous position in a heterocyclic five-membered ring (see below), the following radicals $Ar^1$ being particularly preferred:

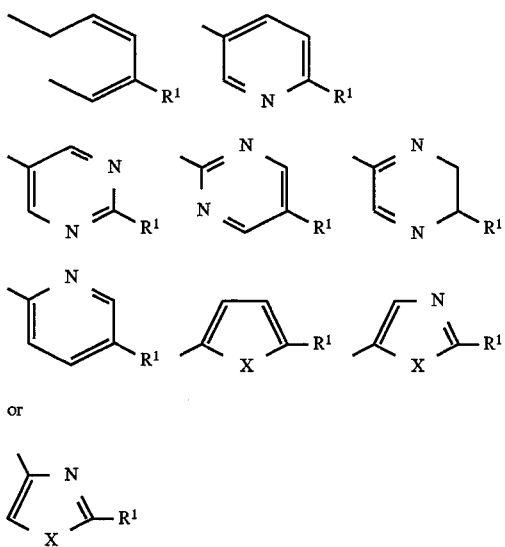

R is preferably $(C_1-C_6)$-alkyl or $(C_3-C_8)$-cycloalkyl, each of which can be partially or fully substituted by halogen, in particular $(C_1-C_6)$-alkyl which can be substituted by up to 3 fluorine atoms, such as $CF_3$, $CF_2H$, or isopropyl or cyclopropyl.

$Ar^2$ is preferably

A

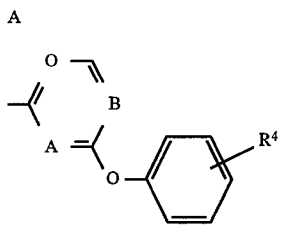

B.

a) Pentafluorophenyl, b) 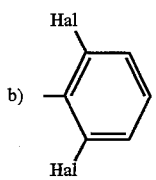

c) 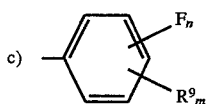

d) 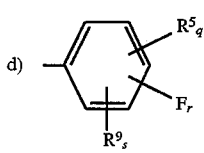

C.

a) 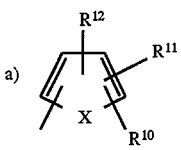

X = O or S b) 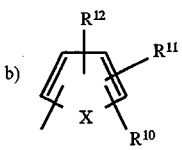

X = $NR^3$ c) 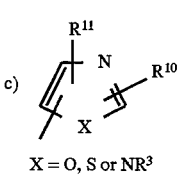

X = O, S or $NR^3$ d) 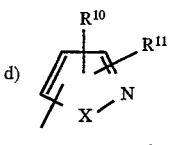

X = O, S or $NR^3$

D. 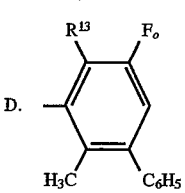

E. 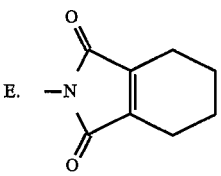

F.

a) 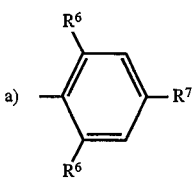

or b) 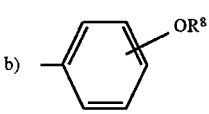

and in which

A, B and C are identical or different and are N, CH or C-Hal,

Q is O, S, NH or $CH_2$, preferably O or $CH_2$, $R^4$ is hydrogen, halogen, O—$CH_2$—CH=$CH_2$ or O—$CH_2$—C≡CH, preferably hydrogen, 4-F, 3-F, 4-Cl, Hal is halogen, $R^9$ is hydrogen or is as defined for $R^1$, m and n are identical or different and are in each case 1, 2, 3 or 4, m+n is 5, $R^5$ is hydrogen or as defined for $R^1$, q, r and s are identical or different and are in each case 1, 2 or 3, q+r+s is 5, $R^3$ is as defined above, $R^{10}$, $R^{11}$ and $R^{12}$ are as defined above, preferably $CH_3$, $CF_3$, CN, phenyl, $CH_2$—$CH=CH_2$, —$CH_2$—$C\equiv CH$ or benzyl, $R^{13}$ is hydrogen, fluorine or methyl, o is 0, 1 or 2, $R^6$ is hydrogen, fluorine or $(C_1-C_6)$-alkyl, $R^7$ is halophenoxy, halobenzyl, O—$CH_2$—$CH=CH_2$, O—$CH_2$—$C\equiv CH$, $CH_2$—$CH=CH_2$ or $CH_2$—$C\equiv CH$ and $R^8$ is $(C_2-C_6)$-alkenyl or $(C_2-C_6)$-haloalkenyl.

If $Ar^2$ is as defined above under A., then preferred compounds are those in which A, B and C are not all simultaneously N, in particular those in which only one of the groups A, B or C is N. The following are preferred:

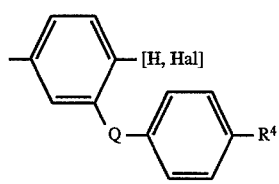

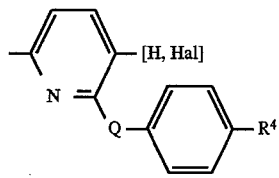

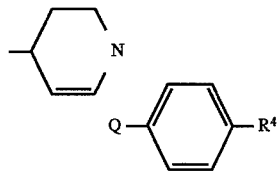

The preferred radical from amongst the $Ar^2$ radicals defined above under B. c) is

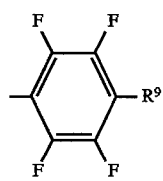

in which $R^9$ is $(C_1-C_6)$-alkyl, in particular methyl, $(C_1-C_6)$-alkoxy, $(C_1-C_6)$-haloalkoxy or $(C_1-C_6)$-haloalkyl.

Preferred radicals from amongst the $Ar^2$ radicals defined above under B. d) are

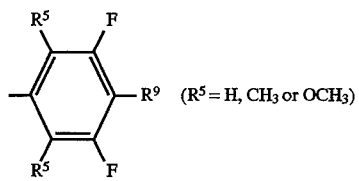 ($R^5$ = H, $CH_3$ or $OCH_3$)

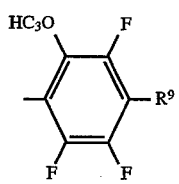

Preferred radicals from amongst the $Ar^2$ radicals defined above under C. are

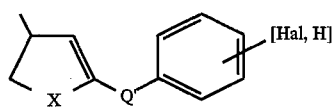

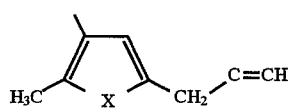

in which

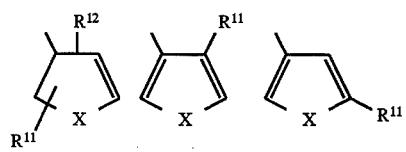

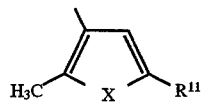

X is $NR^3$, O or S, Q' is O or $CH_2$ and $R^{11}$ and $R^{12}$ are as defined above.

Preferred radicals from those defined above under D. are radicals in which o is 0, in particular those in which $R^{13}$ is hydrogen.

Particularly preferred compounds of the formula I are those in which $Ar^2$ radicals are as defined above under B. c), B. d), C. b), C. c) or C. d), and those in which $Ar^1$ is optionally substituted heteroaryl and R is trifluoromethyl, or in which $Ar^1$ is optionally substituted aryl or heteroaryl, $Ar^2$ is as defined above under D. or E., and R is trifluoromethyl.

The oxime ethers of the formula I can exist in two isomeric forms: the "syn" and the "anti" form. "syn" in this case, independently on the substituent R, designates the oxime ether in which the oxime oxygen is in the syn-position relative to the aromatic or heteroaromatic radical $Ar^1$.

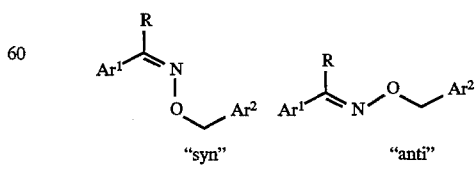

"syn"        "anti"

The invention relates to the syn as well as to the anti form and to mixtures of both forms.

Moreover, compounds of the formula I can have one or more asymmetric carbon atoms. In this case, racemates and diastereomers are possible. The invention in this case embraces the pure isomers as well as mixtures thereof. The diastereomer mixtures can be resolved into the components by customary methods, for example by selective crystallization from suitable solvents or by chromatography. Racemates can be resolved to give the enantiomers by customary methods, for example by salt formation with an optically active acid, separation of the diastereomeric salts and liberation of the pure enantiomers by means of a base.

The invention also relates to a process for the preparation of compounds of the formula I, which comprises a) reacting a compound of the formula II

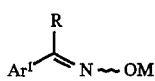
(II)

in which $Ar^1$ and R are as defined in formula I and M is hydrogen or an alkali metal atom, with a compound of the formula III

(III)

in which $Ar^2$ is as defined in formula I and X is a leaving group; if M is hydrogen, in the presence of a suitable base; or b) reacting a compound of the formula IV

(IV)

with a compound of the formula V or a salt thereof such as, for example, a hydrogen halide thereof

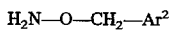
(V)

if appropriate in the presence of a base and then, if appropriate, converting the resulting compound of the formula I into a salt thereof (references: Houben-Weyl, Methoden der organischen Chemie [Methods in Organic Chemistry], Volume 10/4, p. 55 et seq., p. 217 et seq., p. 352 et seq.) Volume E 14b Part 1, p. 287 et seq., p. 307 et seq., p. 367 et seq.).

If, according to process variant a), the starting material used is the oximes (M=hydrogen), the reaction is carried out in the presence of a suitable base such as tertiary amines, alkali metals, alkali metal hydrides, alkali metal amides, alkali metal alkoxides, organolithium and organomagnesium compounds, alkali metal hydroxides, alkali metal hydrogen carbonates, alkali metal carbonates, in a suitable solvent, preferably from the group of the ethers (such as, inter alia, diethyl ether, THF, dimethoxyethane and dioxane), aromatic and non-aromatic, also halogenated hydrocarbons (such as, inter alia, toluene, heptane and chlorobenzene) as well as aprotic, dipolar solvents such as DMF, DMSO, acetonitrile, acetone or N-methylpyrrolidone, at temperatures between −20° and +150° C. The alkylating process can also be carried out with phase-transfer catalysis.

Suitable leaving groups X are halogen (with the exception of fluorine), $OSO_2CH_3$, $OSO_2CF_3$, p-toluenesulfonyloxy or quaternary ammonium salts etc.

An isolated alkali metal oximate (M=alkali metal atom) is alkylated under the same conditions. The presence of a base is not necessary.

The stereochemistry on the oxime is generally retained during alkylation of the oxime/oximate, i.e. "syn"-oxime/oximate gives "syn"-oxime ethers. The same applies analogously to the "anti" compounds.

The oxime ethers according to the invention can furthermore be synthesized by condensing a hydroxylamine O-alkyl-aryl$^2$ ether (salt) with the corresponding ketone, if appropriate in the presence of a suitable base and of a suitable solvent, at temperatures between −20° and +150° C. (variant b).

Bases which are particularly suitable are alkali metal carboxylates, tertiary amines, alkali metal hydroxides, alkali metal carbonates and alkali metal hydrogen carbonates, preferred suitable solvents (also in the form of mixtures) are alcohols, hydrocarbons, halogenated and unhalogenated (also aromatic) hydrocarbons and ethers. The hydroxylamine O-ethers can be prepared by processes described in the literature (Kaztreiner et al., Acta Chem. Hung. 80 (1975) 167).

The ketone oximes of the formula II (M=hydrogen) can be synthesized by the customary preparation processes from the ketone by reacting it with a hydroxylammonium salt such as hydroxylamine hydrochloride at temperatures between −20° and +150° C. in a suitable solvent, from the group comprising the alcohols, the (halogenated) aromatic and non-aromatic hydrocarbons and the ethers (THF, dioxane, diethyl ether, dimethoxyethane), preferably water, if appropriate with an addition of a suitable base as defined under (b) (see also Houben-Weyl; Methoden der organischen Chemie [Methods in Organic Chemistry], Volume 10/4 p. 55 et seq., 352 et seq.; Volume E 14b Part 1, p. 287 et seq., 307 et seq., 367 et seq. and R. L. Salvador et al., J. Med. Chem. 15 (1972) 646).

The oximes, or mixtures of the isomeric oximes, can be converted into the thermodynamically more stable form with the aid of (Lewis) acids such as, inter alia, boron trifluoride etherate, titanium tetrachloride and HCl, by processes described in the literature (U.S. Pat. No. 4,158,015).

Structure elucidation, also of the oxime ethers according to the invention, was carried out analogously to G. J. Karabatsos, N. M. Si, Tetrahedron 23 (1967) 1079 and A. Boder, A. Barabs, Tetrahedron 35 (1979) 233.

Trifluoromethyl ketones, or perfluoroalkyl ketones, of the formula IV.

The trifluoromethyl ketones can be synthesized by several methods, for example those described in the literature (J.-P. Begue et al., Tetrahedron 47 (1991) 3207), but preferably via a) the organolithium and/or Grignard reaction

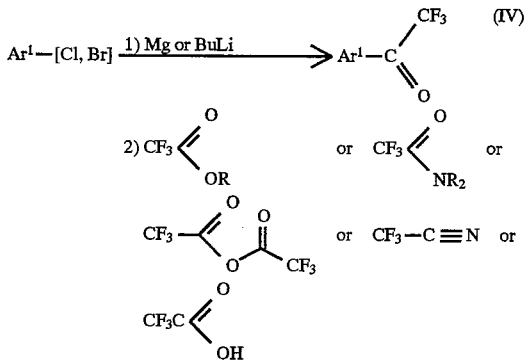

in which $Ar^1$ is an aromatic or heteroaromatic radical (Houben-Weyl, Volume 7/2a, p. 548 et seq., X. Creary, J. Org. Chem. 52 (1987) 5026)

b) or via an addition reaction of trifluorobromomethane/ zinc with the corresponding aldehydes followed by oxidation (HOE 92/F 011)

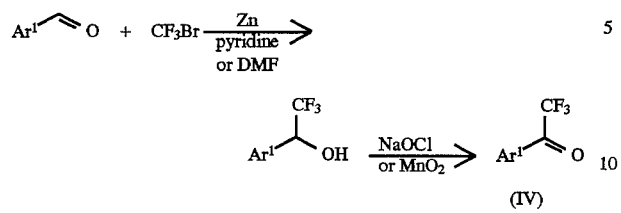

(IV)

c) activated, electron-rich aromatics can be acylated by a Friedel-Crafts reaction or by the Houben-Hoesch reaction (using trifluoroacetonitrile) [Houben-Weyl, Methoden der organischen Chemie [Methods in Organic Chemistry], Volume 7/2a, p. 39, 83].

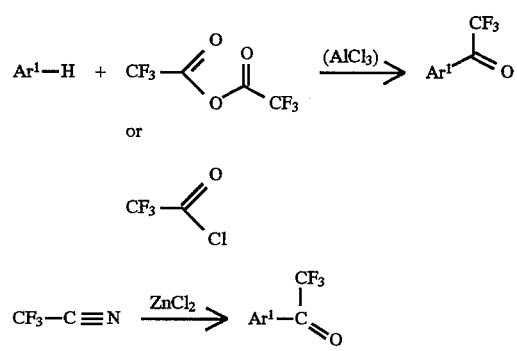

Alkyl aryl ketones.

Alkyl(cycloalkyl) $Ar^1$ ketones were prepared (reference: Houben-Weyl, Methoden der organischen Chemie [Methods in Organic Chemistry], Volume 7/2a) by reacting a) $aryl^1$-Grignard compounds, or $aryl^1$-lithium compounds, with the corresponding carboxylic acid derivatives (X=Li, MgHal)

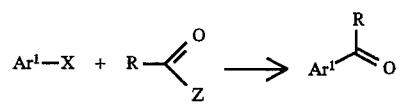

or with the corresponding aldehydes followed by oxidation

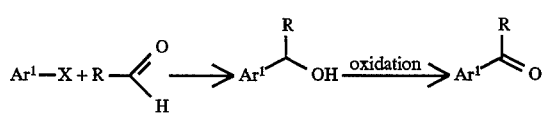

c) the corresponding nitrile and the corresponding organometal compound

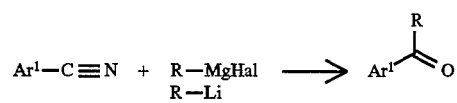

Synthesis of the alkylating agents of the formula III:

The alkylating agents, especially sulfonates and benzyl halides, were synthesized by standard procedure either from the corresponding alcohols by reacting them with sulfonyl chloride (sulfonic anhydride), with thionyl chloride (X=Cl), with hydrobromic acid or phosphorus tribromide (X=Br), or by halogenating the corresponding methylaromatic compound $CH_3$—$Ar^2$ (X=Br, Cl) (see also K. Naumann, Synthetic Pyrethroid Insecticides, Chemistry and Patents, Volume 5, Berlin 1990 and references cited therein).

The active substances are suitable for controlling animal pests, in particular insects, arachnids, helminths, nematodes and molluscs, very particularly preferably for controlling insects and arachnids, which can be found in agriculture, in livestock breeding, in forests, in the protection of stored products and materials and in the hygiene field, while being well tolerated by plants and having a favorable toxicity to warm-blooded species. They are active against normally sensitive and resistant species and against all or individual development stages. The abovementioned pests include:

From the order of the Acarina, for example, *Acarus siro, Argas* spp., *Ornithodoros* spp., *Dermanyssus gallinae, Eriophyes ribis, Phyllocoptruta oleivora,* Boophilus spp., Rhipicephalus spp.,Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Eotetranychus spp., Oligonychus spp., Eutetranychus spp.

From the order of the Isopoda, for example, *Oniscus asellus, Armadium vulgare, Porcellio scaber.*

From the order of the Diplopoda, for example, *Blaniulus guttulatus.*

From the order of the Chilopoda, for example, *Geophilus carpophagus,* Scutigera spp.

From the order of the Symphyla, for example, *Scutigerella immaculata.*

From the order of the Tysanura, for example, *Lepisma saccharina.*

From the order of the Collembola, for example, *Onychiurus armatus.*

From the order of the Orthoptera, for example, *Blatta orientalis, Periplaneta americana, Leucophaea madeirae, Blatella germanica, Acheta domesticus,* Gryllotalpa spp., *Locusta migratoria migratorioides, Melanoplus differentialis, Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp., Linognathus spp.

From the order of the Mallophaga, for example, Damalinea spp.

From the order of the Thysanoptera, for example, *Hercinothrips femoralis, Thrips tabaci.*

From the order of the Heteroptera, for example, Eurygaster spp., *Dysdercus intermedius, Piesma quadrata, Cimex lectularius, Rhodnius prolixus,* Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Photodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis*

*chrysorrhoea*, Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana.*

From the order of the Coleoptera, for example, *Anobium punctatum, Rhizopertha dominica, Bruchidus obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hyperia postica,* Dermestes spp., Trogoderma, Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica.*

From the order of the Hymenoptera, for example, Diprion spp., Hoplocampa spp., Lasius spp., *Monomorium pharaonis,* Vespa spp.

From the order of the Diptera, for example, Aedes spp., Anopheles spp., Culex spp., *Drosophila melanogaster,* Musca spp., Tannia spp., *Calliophora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa.*

From the order of the Siphonaptera, for example, *Xenopsylla cheopsis,* Ceratophyllus spp.

From the order of the Arachnida, for example, *Scorpio maurus, Latrodectus mactans.*

From the class of the Helminthes, for example, Haemonchus, Trichostrongulus, Ostertagia, Cooperia, Chabertia, Strongyloides, Oesophagostomum, Hyostrongulus, Ancylostoma, Ascaris and Heterakis as well as Fasciola as well as nematodes which are harmful to plants and animals, for example those from the genera Meloidogyne, Heterodera, Ditylenchus, Aphelenchoides, Radopholus, Globodera, Pratylenchus, Longidorus and Xiphinema.

From the class of the Gastropoda, for example, Deroceras spp., Arion spp., Lymnaea spp., Galba spp., Succinea spp., Biomphalaria spp., Bulinus spp., Oncomelania spp.

From the class of the Bivalva, for example Dreissena spp.

The invention also relates to agents which comprise the compounds of the formula I in addition to suitable formulation auxiliaries.

The agents according to the invention generally comprise the active substances of the formula I in amounts of 1 to 95% by weight.

They can be formulated in a variety of ways, as predetermined by the biological and/or chemico-physical parameters. The following possibilities are therefore suitable for formulation: wettable powders (WP), emulsifiable concentrates (EC), aqueous solutions (SC), emulsions, sprayable solutions, dispersions on an oil or water base (SC), suspoemulsions (SC), dusts (DP), seed-dressing agents, granules in the form of microgranules, spray granules, coated granules and adsorption granules, water-dispersible granules (WG), ULV formulations, microcapsules, waxes and baits.

These individual formulation types are known in principle and are described, for example, in: Winnacker-Küchler, "Chemische Technologie" [Chemical Technology], Volume 7, C. Hauser Verlag Munich, 4th Ed. 1986; van Falkenberg, "Pesticides Formulations", Marcel Dekker N.Y., 2nd Ed. 1972–73; K. Martens, "Spray Drying Handbook", 3rd Ed. 1979, G. Goodwin Ltd. London.

The formulation auxiliaries required, such as inert materials, surfactants, solvents and other additives are equally known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marschen, "Solvents Guide", 2nd Ed., Interscience, N.Y. 1950; McCutcheon's, "Detergents and Emulsifiers Annual", MC Pubabl. I. Corp., Ridgewood N.J.; Sisley and Wood. "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Combinations with other pesticidally active substances, fertilizers and/or growth regulators may also be prepared on the basis of these formulations, for example in the form of a readymix or a tank mix. Wettable powders are preparations which are uniformly dispersible in water and which, besides the active substance, also contain wetting agents, for example polyoxethylated alkylphenols, polyoxethylated fatty alcohols, alkylsulfonates or alkylphenolsulfonates, and dispersants, for example sodium ligninsulfonate, sodium 2,2'-dinaphthylmethane-6,6'-disulfonate, sodium dibutylnaphthalenesulfonate, or else sodium oleylmethyltaurinate, in addition to a diluent or inert substance. Emulsifiable concentrates are prepared by dissolving the active substance in an organic solvent, for example butanol, cyclohexanone, dimethylformamide, xylene or else higher-boiling aromatics or hydrocarbons, with an addition of one or more emulsifiers. Examples of emulsifiers which can be used are: calcium alkylarylsulfonates, such as calcium dodecylbenzenesulfonate, or non-ionic emulsifiers such as fatty acid polyglycol esters, alkylaryl polyglycol ethers, fatty alcohol polyglycol ethers, propylene oxide/ ethylene oxide condensation products, alkyl polyethers, sorbitan fatty acid esters, polyoxyethylene sorbitan fatty acid esters or polyoxethylene sorbitol esters.

Dusts are obtained by grinding the active substance with finely divided solid substances, for example talc, natural clays such as kaolin, bentonite, pyrophyllite or diatomaceous earth. Granules can be prepared either by spraying the active substance onto adsorptive, granulated inert material or by applying active substance concentrates to the surface of carriers, such as sand, kaolinites or granulated inert material, by means of binders, for example polyvinyl alcohol, sodium polyacrylate or else mineral oils. Suitable active substances can also be granulated in the fashion which is conventional for the production of fertilizer granules, if desired as a mixture with fertilizers.

The concentration of active substance in wettable powders is, for example, approximately 10 to 90% by weight, the remainder to 100% is composed of conventional formulation components. In the case of emulsifiable concentrates, the concentration of active substance can be approximately 5 to 80% by weight. Formulations in the form of dusts usually contain 5 to 20% of active substance, sprayable solutions approximately 2 to 20% by weight. In granules, the active substance content depends partly on whether the active compound is liquid or solid and on which granulation auxiliaries, fillers etc., are used.

In addition, the active substance formulations mentioned contain, if appropriate, the adhesives, wetting agents, dispersants, emulsifiers, penetrants, solvents, fillers or carriers which are conventional in each case.

For use, the concentrates which are present in commercially available form are, if appropriate, diluted in the customary manner, for example in wettable powders, emulsifiable concentrates, dispersions and in some cases also in microgranules using water, while preparations in the form of dusts and granulated preparations as well as sprayable solutions are customarily not further diluted with other inert substances before use.

The application rate required varies with the external conditions such as, inter alia, temperature and humidity. It can vary within wide limits, for example between 0.005 and 10.0 kg/ha or more of active substance, but it is preferably between 0.01 and 5 kg/ha.

In their commercially available formulations and in the use forms prepared with these formulations, the active substances according to the invention can exist in the form of a mixture with other active substances such as insecticides, attractants, sterilants, acaricides, nematicides, fungicides, growth-regulating substances or herbicides.

The pesticides include, for example, phosphoric esters, carbamates, carboxylates, formamidines, tin compounds, substances prepared by microorganisms and the like. Preferred components in the mixtures are 1. from the group comprising the phosphorus compounds acephate, azamethiphos, azinphos-ethyl, azinphosmethyl, bromophos, bromophos-ethyl, chlorfenvinphos, chlormephos, chlorpyrifos, chlorpyriphos-methyl, demeton, demeton-S-methyl, demeton-S-methylsulphone, dialifos, diazinon, dichlorvos, dicrotophos, O,O-1,2,2,2-tetrachloroethylphosphorthioate (SD 208 304), dimethoate, disulfoton, EPN, ethion, ethoprophos, etrimfos, famphur, fenamiphos, fenitrothion, fensulfothion, fenthion, fonofos, formothion, heptenophos, isazophos, Isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphos-methyl, profenofos, propaphos, propetamphos, thiometon, triazophos, trichlorphon, vamidothion;

2. from the group comprising the carbamates aldicarb, 2-sec-butylphenyl methylcarbamate (BPMC), carbaryl, carbofuran, carbosulfan, cloethocarb, benfuracarb ethiofencarb, furathiocarb, isoprocarb, methomyl, 5-methyl-m-cumenylbutyryl (methyl)carbamate, oxamyl, pirymicarb, propoxur, thiodicarb, thiofanox, ethyl, 4,6,9-triaza-4-benzyl-6,10-dimethyl-8-oxa-7-oxo-5,11-dithia-9-dodecenoate (OK 135), 1-methylthio (ethylidenamino) N-methyl-N-(morpholinothio) carbamate (UC 51717);

3. from the group comprising the carboxylates allethrin, alphametrin, 5-benzyl-3-furylmethyl (E)-(1R)-cis-2,2-dimethyl-3-(2-oxothiolan-3-ylidene-methyl)-cyclopropanecarboxylate, bioallethrin, bioallethrin ((S)-cyclopentyl isomer), bioresmethrin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyfluthrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, phenothrin ((R) isomer), d-prallethrin, pyrethrins (natural products), resmethrin, tefluthrin, tetramethrin, tralamethrin, 4. from the group comprising the amidines amitraz, chloridime form;

5. from the group comprising the tin compounds cyhexatin, fenbutin oxide;

6. others abarnectin, *Bacillus thuringiensis,* bensultap, binapacryl, bromopropylate, buprofezin, camphector, cartap, chlorobenzilate, chlorfluazuron, 2-(4-chlorophenyl)-4,5-diphenylthiophene (UBI-T 930), chlorfentezine, 2-naphthylmethyl cyclopropane carboxylate (Ro 12-0470), cyromazin, ethyl N-(3,5-dichloro-4-(1,1,2,3,3,3-hexafluoro-1-propyloxy) phenyl)carbamoyl)-2-chlorobenzcarboximidate, DDT, diflubenzuron, N-(2,3-dihydro-3-methyl-1,3-thiazol-2-ylidene)-2,4-xylidene, dinobuton, dinocap, enclosulfan, ethofenprox, (4-ethoxyphenyl) (dimethyl) (3-(3-phenoxyphenyl)propyl)silane, (4-ethoxyphenyl) (3-(4-fluoro-3-phenoxyphenyl)propyl)dimethylsilane, fenoxycarb, flubenzimine, flucycloxuron, flufenoxuron, gamma-HCH, hexythiazox, hydramethylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazanan-3-ylcarbamaldehyde (WL 108477), propargite, teflubenzuron, tetradifon, tetrasul, thiocyclam and triflumuron.

The active substance content of the use forms prepared from the commercially available formulations can be from 0.00000001 to 99% by weight of active substance, preferably between 0.00001 and 1% by weight. Application is effected in a conventional fashion, matched to the use forms.

The active substances according to the invention are also suitable for controlling endo- and ectoparasites as well as nematodes in the field of veterinary medicine and animal husbandry.

The active substances according to the invention are applied in a known fashion, such as by oral administration in the form of, for example, tablets, capsules, drinks, granules, by, for example, dipping, spraying, pouring on and spotting on and powdering, as well as by parenteral administration, in the form of, for example, an injection.

Accordingly, the novel compounds of the formula I according to the invention can also be employed particularly advantageously in livestock breeding (for example cattle, sheep, pigs, and poultry such as chickens, geese etc.). In a preferred embodiment of the invention, the novel compounds, if appropriate in suitable formulations (cf. above) and if appropriate with the drinking water or feed, are administered orally to the animals. Since excretion in the feces is effective, the development of insects in the feces of the animals can be prevented very simply in this fashion. The dosages and formulations suitable in each case depend particularly on the species and development stage of the productive livestock and also on the danger of infestation, and they can be determined and fixed readily by conventional methods. In the case of cattle, the novel compounds can be employed, for example, at dosage rates of 0.01 to 1 mg/kg of body weight.

The following examples are intended to illustrate the invention without imposing any limitation.

Formulation Examples a) A dust is obtained by mixing 10 parts by weight of active substance and 90 parts by weight of talc as inert substance and comminuting the mixture in a hammer mill.

b) A dispersion concentrate which is readily dispersible in water is prepared by mixing 25 parts by weight of active substance, 65 parts by weight of kaolin-containing quartz as inert substance, 10 parts by weight of potassium ligninsulfonate and 1 part by weight of sodium oleoylmethyltaurinate as wetting and dispersing agent, and grinding the mixture in a pinned-disk mill.

c) A dispersion concentrate which is readily dispersible in water is prepared by mixing 40 parts by weight of active substance with 7 parts by weight of a sulfosuccinic monoester, 2 parts by weight of a sodium salt of ligninsulfonic acid and 51 parts by weight of water and grinding the mixture in a ball mill to a fineness of below 5 microns.

d) An emulsifiable concentrate is prepared from 15 parts by weight of active substance, 75 parts by weight of cyclohexanone as solvent and 10 parts by weight of oxethylated nonylphenol (10 EO) as emulsifier.

e) Granules can be prepared from 2 to 15 parts by weight of active substance and an inert granule carrier material such as attapulgite, pumice granules and/or quartz sand.

It is expedient to use a suspension of the wettable powder of Example b) with a solids content of 30% and to spray the suspension onto the surface of attapulgite granules which are then dried and mixed intimately. The amount by weight of the wettable powder is approx. 5% and that of the inert carrier material approx. 95% of the finished granules.

Chemical Examples

General Procedures for Synthesizing the Oxime Ethers

Procedure A (Tabulated Example 65)

1.44 g (5.0 mmol) of 6-(2,2,2-trifluoroethoxy)pyridin-3-yl trifluoromethyl ketone oxime (m.p. 57°–58° C.) and 0.69 g (5.0 mmol) of potassium carbonate are stirred in 7 ml of toluene together with 0.13 g (0.05 mmol) of 18-crown-6. 1.53 g (5.1 mmol) of 4-fluoro-3-(4-fluorophenoxy)benzyl bromide in 5 ml of toluene are added dropwise. After 3 hours (DC check), insoluble particles are filtered off, and the organic phase is washed three times using water. Drying over magnesium sulfate gives 2.45 g (97%) of a colorless, viscous oil of analytical reagent quality.

Procedure B (Tabulated Example 27)

5.46 g (20.0 mmol) of 6-(2,2,2-trifluoroethoxy)pyridin-3-yl trifluoromethyl ketone and 5.53 g (20.5 mmol) of hydroxylamine O-(4-fluoro-3-phenoxyphenyl) methyl ether hydrochloride together with 1.40 g (10.2 mmol) of potassium carbonate are heated at the boil in 20 ml of dry ethanol (DC check). After 15 hours (DC check), the mixture is cooled, and undissolved particles are filtered off. The mixture is taken up in ethyl acetate/water, and the organic phase is washed three times with water. Drying over magnesium sulfate gives 9.32 g (95%) of oil which contains a small amount of impurities and which was chromatographed over silica gel using ethyl acetate:heptane=1:20.

Yield: 8.75 g (90%) of oil of analytical reagent quality b.p. 367° C. (GC) purity (GC)=98%

General Procedure for Synthesizing the Oximes

Procedure C:

11.76 g (50.04 mmol) of 6-propyloxypyridin-3-yl trifluoromethyl ketone and 3.85 g (55.7 mmol) of hydroxylamine hydrochloride together with 3.48 g (25.2 mmol) of potassium carbonate are refluxed for 8 hours in 40 ml of ethanol (DC check). When the mixture has cooled to room temperature, the ethanol is removed by distillation in vacuo (12 torr/40° C.), the residue is taken up in water, and the mixture is extracted several times using ethyl acetate. Drying over magnesium sulfate gives 12.03 g (96%) of a yellowish wax which can be reacted without further purification.

All oximes and oxime ethers were synthesized analogously to these procedures.

For the sake of simplicity, the radicals $Ar^2$ will be abreviated in the following table, to $E^x$ (x=1–61).

| $Ar^2$ | Name or formula |
|---|---|
| $E^1$ | 4-fluoro-3-phenoxyphenyl |
| $E^2$ | 3-phenoxyphenyl |
| $E^3$ | 6-phenoxy-pyridin-2-yl |
| $E^4$ | 6-chloropyridin-3-yl |
| $E^5$ | 3-(4-chlorophenoxy)phenyl |
| $E^6$ | 4-fluoro-3-(3-fluorophenoxy)phenyl |
| $E^7$ | 4-fluoro-3-(4-fluorophenoxy)phenyl |
| $E^8$ | pentafluorophenyl |
| $E^9$ | 4-methyl-2,3,5,6-tetrafluorophenyl |
| $E^{10}$ | 4-methoxy-2,3,5,6-tetrafluorophenyl |
| $E^{11}$ | 4-ethylthio-2,3,5,6-tetrafluorophenyl |
| $E^{12}$ | 4-ethylsulfonyl-2,3,5,6-tetrafluorophenyl |
| $E^{13}$ | 4-tert.-butoxy-2,3,5,6-tetrafluorophenyl |
| $E^{14}$ | 4-difluoromethoxy-2,3,5,6-tetrafluorophenyl |
| $E^{15}$ | 4-allyl-2,3,5,6-tetrafluorophenyl |
| $E^{16}$ | 4-vinyl-2,3,5,6-tetrafluorophenyl |
| $E^{17}$ | 4-bromomethyl-2,3,5,6-tetrafluorophenyl |
| $E^{18}$ | 4-methoxymethyl-2,3,5,6-tetrafluorophenyl |
| $E^{19}$ | 4-allyloxymethyl-2,3,5,6-tetrafluorophenyl |
| $E^{20}$ | 3,5-difluorophenyl |
| $E^{21}$ | 2,4-difluorophenyl |
| $E^{22}$ | 2,6-difluorophenyl |
| $E^{23}$ | 2-chloro-3-fluorophenyl |
| $E^{24}$ | 3,4-difluorophenyl |
| $E^{25}$ | 2,3-difluorophenyl |
| $E^{26}$ | 2,5-difluorophenyl |
| $E^{27}$ | 2,4,6-trifluorophenyl |
| $E^{28}$ | 4-benzyloxyphenyl |
| $E^{29}$ | 3-(1,1,2,2-tetrafluoroethoxy)phenyl |
| $E^{30}$ | 3-(2,2-dichlorovinyloxy)phenyl |
| $E^{31}$ | 3-benzyloxyphenyl |
| $E^{32}$ | 4-methylphenyl |
| $E^{33}$ | 4-tert.-butylphenyl |
| $E^{34}$ | (5-benzyl)fur-3-yl |
| $E^{35}$ | (5-benzyl)thien-3-yl |
| $E^{36}$ | N-propargyl-2-trifluoromethylpyrrol-3-yl |
| $E^{37}$ | N-allyl-3-cyanopyrrol-3-yl |
| $E^{38}$ | 2-methyl-3-phenylphenyl |
| $E^{39}$ | 2-cyanophenyl |
| $E^{40}$ | 3-cyanophenyl |
| $E^{41}$ | 4-cyanophenyl |
| $E^{42}$ | 2-trifluoromethylphenyl |
| $E^{43}$ | 3-trifluoromethylphenyl |
| $E^{44}$ | 4-trifluoromethylphenyl |
| $E^{45}$ | 2-(phenylsulfonylmethyl)phenyl |
| $E^{46}$ | 3,4-methylenedioxyphenyl |
| $E^{47}$ | p-biphenyl |
| $E^{48}$ | 2-naphthyl |
| $E^{49}$ | 3-trifluoromethoxy |
| $E^{50}$ | 4-trifluoromethoxy |
| $E^{51}$ | N-tetrahydrophthalimidyl |
| $E^{52}$ | 3-benzoyloxyphenyl |
| $E^{53}$ | 6-bromobenzo-1,3-dioxan-8-yl |
| $E^{54}$ | 6-nitrobenzo-1,3-dioxan-8-yl |
| $E^{55}$ | (3-phenyloxymethyl)phenyl |

-continued

| Ar² | Name or formula |
|---|---|
| E⁵⁶ | [thiazole linked to 4-CF₃-phenyl] |
| E⁵⁷ | [thiazole linked to 4-tBu-phenyl] |
| E⁵⁸ | [thiazole linked to 3-pyridyl] |
| E⁵⁹ | [methyl-thiazole with CH₃] |
| E⁶⁰ | [thiazole linked to 4-Cl-phenyl] |
| E⁶⁰ | [2,3,5,6-tetrafluorophenyl-CH₂-O-N=C(CF₃)-(6-chloropyridin-3-yl)] |

-continued

| Ar² | Name or formula |
|---|---|
| E⁶¹ | [2,3,5,6-tetrafluorophenyl-CH₂-O-N=C(CF₃)-(6-(OCH₂-CF₃)pyridin-3-yl)] |
| E⁶² | 2,3,6-trifluorophenyl |
| E⁶³ | 2,3,4-trifluorophenyl |
| E⁶⁴ | 2,3,5-trifluorophenyl |
| E⁶⁵ | 3,4,5-trifluorophenyl |
| E⁶⁶ | 3-[3-(4-chlorophenyl)-1,2,4-(oxadiazol-5-yl)phen-1-yl |
| E⁶⁷ | 6-chloro-(3,4-methylenedioxy)phenyl |
| E⁶⁸ | (2,6-dichloropyridin-4-yl) |
| E⁶⁹ | (2-chlorothiazol-5-yl) |
| E⁷⁰ | (3-chloro-4-nitrophenyl) |
| E⁷¹ | [6-(2,2,2-trifluoroethoxy)pyridin-3-yl] |
| E⁷² | phenyl |
| E⁷³ | (5,7-dichlorobenzoxazol-2-yl) |

In addition, in the table below,

M is methyl,

Et is ethyl,

Bu is butyl, t-Bu is tert.-butyl and

Ph is phenyl

TABLE 1

$$R^1-Ar^1-\underset{\underset{R}{|}}{C}=N-O-CH_2-Ar^2$$

| No. | R¹ | Ar¹ | R | Ar² |
|---|---|---|---|---|
| 1 | 6-H | 3-pyridyl | CF₃ | E¹ |
| 2 | 6-Cl | " | " | E¹ |
| 3 | 6-Br | " | " | E¹ |
| 4 | 6-OMe | " | " | E¹ |
| 5 | 6-OCH₂CH₃ | " | " | E¹ |
| 6 | 6-OCH₂CH₂CH₃ | " | " | E¹ |
| 7 | 6-OCH—CH₃)₂ | " | " | E¹ |
| 8 | 6-OBu | " | " | E¹ |
| 9 | 6-OCH₂CH(CH₃)₂ | " | " | E¹ |
| 10 | 6-OCH(CH₃)₂ | " | " | E¹ |
| 11 | 6-O(CH₂)₄CH₃ | " | " | E¹ |
| 12 | 6-O(CH₂)₂CH(CH₃)₂ | " | " | E¹ |
| 13 | 6-OC(CH₃)₂—CH₂CH₃ | " | " | E¹ |
| 14 | 6-O(CH₂)₅CH₃ | " | " | E¹ |
| 15 | 6-O—CH₂—CH₂—OMe | " | " | E¹ |
| 16 | 6-O—CH₂—CH=CH₂ | " | " | E¹ |
| 17 | 6-O—CH₂—C≡CH | " | " | E¹ |
| 18 | 6-OPh | " | " | E¹ |
| 19 | 6-cyclopentyloxy | " | " | E¹ |
| 20 | 6-CH₃ | " | " | E¹ |
| 21 | 6-CH₂OCH₃ | " | " | E¹ |
| 22 | 6-CH₂O—CH=CH₂ | " | " | E¹ |
| 23 | 6-CH₂O—C≡CH | " | " | E¹ |

TABLE 1-continued $$R^1-Ar^1-\underset{\underset{R}{|}}{C}=N\sim O-CH_2-Ar^2$$

| No. | $R^1$ | $Ar^1$ | R | $Ar^2$ |
|---|---|---|---|---|
| 24 | 6-CH$_2$SMe | " | " | E$^1$ |
| 25 | 6-CH$_2$SPh | " | " | E$^1$ |
| 26 | 6-CH$_2$NMe$_2$ | " | " | E$^1$ |
| 27 | 6-OCH$_2$CF$_3$ | " | " | E$^1$ |
| 28 | 6-OCH—(CF$_3$)$_2$ | " | " | E$^1$ |
| 29 | 6-SMe | " | " | E$^1$ |
| 30 | 6-SPh | " | " | E$^1$ |
| 31 | 6-NMe$_2$ | " | " | E$^1$ |
| 32 | 6-N-morpholino | " | " | E$^1$ |
| 33 | 6-Cl | " | " | E$^2$ |
| 34 | 6-Br | " | " | E$^2$ |
| 35 | 6-OMe | " | " | E$^2$ |
| 36 | 6-OCH$_2$CH$_3$ | " | " | E$^2$ |
| 37 | 6-OCH$_2$CH$_2$CH$_3$ | " | " | E$^2$ |
| 38 | 6-OCH(CH$_3$)$_2$ | " | " | E$^2$ |
| 39 | 6-OCH$_2$CH(CH$_3$)$_2$ | " | " | E$^2$ |
| 40 | 6-O—CH$_2$CH$_2$—OMe | " | " | E$^2$ |
| 41 | 6-O—CH$_2$CH═CH$_2$ | " | " | E$^2$ |
| 42 | 6-O—CH$_2$C≡CH | " | " | E$^2$ |
| 43 | 6-OPh | " | " | E$^2$ |
| 44 | 6-CH$_3$ | " | " | E$^2$ |
| 45 | 6-CH$_2$OCH$_3$ | " | " | E$^2$ |
| 46 | 6-CH$_2$O—CH$_2$—CH═CH$_2$ | " | " | E$^2$ |
| 47 | 6-CH$_2$O—C≡CH | " | " | E$^2$ |
| 48 | 6-OCH$_2$CF$_3$ | " | " | E$^2$ |
| 49 | 6-OCH(CF$_3$)$_2$ | " | " | E$^2$ |
| 50 | 6-NMe$_2$ | " | " | E$^2$ |
| 51 | 6-N-morpholino | " | " | E$^2$ |
| 52 | 6-H | " | " | E$^3$ |
| 53 | 6-Cl | " | " | E$^3$ |
| 54 | 6-Br | " | " | E$^3$ |
| 55 | 6-OCH$_2$CH$_3$ | " | " | E$^3$ |
| 56 | 6-OCH(CH$_3$)$_2$ | " | " | E$^3$ |
| 57 | 6-O(CH$_2$)CH$_2$CH$_3$ | " | " | E$^3$ |
| 58 | 6-OCH$_2$CF$_3$ | " | " | E$^3$ |
| 59 | 6-OCH$_2$CF$_3$ | " | " | E$^4$ |
| 60 | 6-Cl | " | " | E$^5$ |
| 61 | 6-OCH$_2$CH$_3$ | " | " | E$^5$ |
| 62 | 6-OCH$_2$CF$_3$ | " | " | E$^5$ |
| 63 | 6-Cl | " | " | E$^6$ |
| 64 | 6-OCH$_2$CF$_3$ | " | " | E$^6$ |
| 65 | 6-OCH$_2$CF$_3$ | " | " | E$^7$ |
| 66 | 6-Cl | " | " | E$^7$ |
| 67 | 6-Cl | " | " | E$^8$ |
| 68 | 6-OCH$_2$CH$_3$ | " | " | E$^8$ |
| 69 | 6-OCH$_2$CH$_2$CH$_3$ | " | " | E$^8$ |
| 70 | 6-OCH(CH$_3$)$_2$ | " | " | E$^8$ |
| 71 | 6-OCH(CH$_3$)$_2$ | " | " | E$^8$ |
| 72 | 6-O(CH$_2$)$_5$CH$_3$ | " | " | E$^8$ |
| 73 | 6-OCH$_2$CF$_3$ | " | " | E$^8$ |
| 74 | 6-OCH(CF$_3$)$_2$ | " | " | E$^8$ |
| 75 | 6-OCH$_2$CH$_2$O—CH$_3$ | " | " | E$^8$ |
| 76 | 6-OCH$_3$ | " | " | E$^8$ |
| 77 | 6-OPh | " | " | E$^8$ |
| 78 | 6-cyclopentyloxy | " | " | E$^8$ |
| 79 | 6-CH$_3$ | " | " | E$^8$ |
| 80 | 6-CH$_2$OMe | " | " | E$^8$ |
| 81 | 2-CH$_2$OMe | 5-pyrimidinyl | CF$_3$ | E$^1$ |
| 82 | 2-Cl | " | " | E$^7$ |
| 83 | 2-Br | " | " | E$^7$ |
| 84 | 2-OMe | " | " | E$^7$ |
| 85 | 2-OCH$_2$CH$_3$ | " | " | E$^7$ |
| 86 | 2-OCH$_2$CH$_2$CH$_3$ | " | " | E$^7$ |
| 87 | 2-OCH(CH$_3$)$_2$ | " | " | E$^7$ |
| 88 | 2-O(CH$_2$)$_5$CH$_3$ | " | " | E$^7$ |
| 89 | 2-OPh | " | " | E$^7$ |
| 90 | 2-OCH$_2$CF$_3$ | " | " | E$^7$ |
| 91 | 6-H | 3-pyridyl | CF$_3$ | E$^9$ |
| 92 | 6-Cl | " | " | E$^9$ |
| 93 | 6-Br | " | " | E$^9$ |
| 94 | 6-OCH$_3$ | " | " | E$^9$ |

TABLE 1-continued $$R^1-Ar^1-\underset{\underset{R}{|}}{C}=N\sim O-CH_2-Ar^2$$

| No. | R$^1$ | Ar$^1$ | R | Ar$^2$ |
|---|---|---|---|---|
| 95 | 6-OCH$_2$CH$_3$ | " | " | E$^9$ |
| 96 | 6-OCH(CH$_3$)$_2$ | " | " | E$^9$ |
| 97 | 6-OCH$_2$CH$_2$CH$_3$ | " | " | E$^9$ |
| 98 | 6-OCH$_2$CH(CH$_3$)$_2$ | " | " | E$^9$ |
| 99 | 6-O(CH$_2$)$_5$CH$_3$ | " | " | E$^9$ |
| 100 | 6-O—CH$_2$CH$_2$OCH$_3$ | " | " | E$^9$ |
| 101 | 6-O—CH$_2$—CH=CH$_2$ | " | " | E$^9$ |
| 102 | 6-O—CH$_2$—C≡CH | " | " | E$^9$ |
| 103 | 6-OPh | " | " | E$^9$ |
| 104 | 6-OCH$_2$CF$_3$ | " | " | E$^9$ |
| 105 | 6-OCH(CF$_3$)$_2$ | " | " | E$^9$ |
| 106 | 6-cyclopentyloxy | " | " | E$^9$ |
| 107 | 6-NMe$_2$ | " | " | E$^9$ |
| 108 | 6-N-morpholino | " | " | E$^9$ |
| 109 | 6-SMe | " | " | E$^9$ |
| 110 | 6-SPh | " | " | E$^9$ |
| 111 | 6-CH$_3$ | " | " | E$^9$ |
| 112 | 6-CH$_2$OCH$_3$ | " | " | E$^9$ |
| 113 | 6-CH$_2$O—CH=CH$_2$ | " | " | E$^9$ |
| 114 | 6-CH$_2$NMe$_2$ | " | " | E$^9$ |
| 115 | 6-SPh | " | " | E$^9$ |
| 116 | 6-SMe | " | " | E$^9$ |
| 117 | 6-NMe$_2$ | " | " | E$^9$ |
| 118 | 6-N-morpholino | " | " | E$^9$ |
| 119 | 6-NHPh | " | " | E$^9$ |
| 120 | 6-H | " | " | E$^{10}$ |
| 121 | 6-Cl | " | " | E$^{10}$ |
| 122 | 6-Br | " | " | E$^{10}$ |
| 123 | 6-OMe | " | " | E$^{10}$ |
| 124 | 6-OCH$_2$CH$_3$ | " | " | E$^{10}$ |
| 125 | 6-O(CH$_2$)$_2$CH$_3$ | " | " | E$^{10}$ |
| 126 | 6-OCH(CH$_3$)$_2$ | " | " | E$^{10}$ |
| 127 | 6-OCH$_2$CH(CH$_3$)$_2$ | " | " | E$^{10}$ |
| 128 | 6-OCH$_2$CF$_3$ | " | " | E$^{10}$ |
| 129 | 6-O—CH(CF$_3$)$_2$ | " | " | E$^{10}$ |
| 130 | 6-OPh | " | " | E$^{10}$ |
| 131 | 6-O(CH$_2$)$_5$CH$_3$ | " | " | E$^{10}$ |
| 132 | 6-O—CH$_2$—CH$_2$—OCH$_3$ | " | " | E$^{10}$ |
| 133 | 6-CH$_3$ | " | " | E$^{10}$ |
| 134 | 6-CH$_2$OCH$_3$ | " | " | E$^{10}$ |
| 135 | 6-CH$_2$O—CH=CH$_2$ | " | " | E$^{10}$ |
| 136 | 6-NMe$_2$ | " | " | E$^{10}$ |
| 137 | 6-N-morpholino | " | " | E$^{10}$ |
| 138 | 6-SPh | " | " | E$^{10}$ |
| 139 | 6-SMe | " | " | E$^{10}$ |
| 140 | 6-H | " | " | E$^{11}$ |
| 141 | 6-Cl | " | " | E$^{11}$ |
| 142 | 6-Br | " | " | E$^{11}$ |
| 143 | 6-OMe | " | " | E$^{11}$ |
| 144 | 6-OCH$_2$—CH$_3$ | " | " | E$^{11}$ |
| 145 | 6-OCH$_2$CH$_2$CH$_3$ | " | " | E$^{11}$ |
| 146 | 6-O—CH(CH$_3$)$_2$ | " | " | E$^{11}$ |
| 147 | 6-O—CH$_2$CH(CH$_3$)$_2$ | " | " | E$^{11}$ |
| 148 | 6-OCH$_2$CF$_3$ | " | " | E$^{11}$ |
| 149 | 6-O—CH(CF$_3$)$_2$ | " | " | E$^{11}$ |
| 150 | 6-O—CH$_2$—CH$_2$—OMe | " | " | E$^{11}$ |
| 151 | 6-OPh | " | " | E$^{11}$ |
| 152 | 6-CH$_3$ | " | " | E$^{11}$ |
| 153 | 6-OCH$_2$CF$_3$ | " | " | E$^{12}$ |
| 154 | 6-H | " | " | E$^{13}$ |
| 155 | 6-Cl | " | " | E$^{13}$ |
| 156 | 6-OCH$_2$CH$_3$ | " | " | E$^{13}$ |
| 157 | 6-OCH$_2$CH$_2$CH$_3$ | " | " | E$^{13}$ |
| 158 | 6-O—CH(CH$_3$)$_2$ | " | " | E$^{13}$ |
| 159 | 6-OCH$_2$CF$_3$ | " | " | E$^{13}$ |
| 160 | 6-O—CH(CF$_3$)$_2$ | " | " | E$^{13}$ |
| 161 | 6-O—CH$_2$—CH$_2$—OMe | " | " | E$^{13}$ |
| 162 | 6-CH$_3$ | " | " | E$^{13}$ |
| 163 | 6-CH$_2$OMe | " | " | E$^{13}$ |
| 164 | 6-Cl | " | " | E$^{14}$ |
| 165 | 6-OCH$_2$CH$_3$ | " | " | E$^{14}$ |
| 166 | 6-OCH$_2$CH$_2$CH$_3$ | " | " | E$^{14}$ |

TABLE 1-continued $$R^1-Ar^1-\underset{\underset{R}{|}}{C}=N\sim O-CH_2-Ar^2$$

| No. | R¹ | Ar¹ | R | Ar² |
|---|---|---|---|---|
| 167 | 6-OCH₂CF₃ | " | " | E¹⁴ |
| 168 | OPh | " | " | E¹⁴ |
| 169 | 6-CH₃ | " | " | E¹⁴ |
| 170 | 6-CH₂OMe | " | " | E¹⁴ |
| 171 | 6-H | " | " | E¹⁵ |
| 172 | 6-Cl | " | " | E¹⁵ |
| 173 | 6-Br | " | " | E¹⁵ |
| 174 | 6-OCH₃ | " | " | E¹⁵ |
| 175 | 6-OCH₂CH₃ | " | " | E¹⁵ |
| 176 | 6-OCH₂CH₂CH₃ | " | " | E¹⁵ |
| 177 | 6-OCH(CH₃)₂ | " | " | E¹⁵ |
| 178 | 6-OCH₂—CH(CH₃)₂ | " | " | E¹⁵ |
| 179 | 6-O—CH₂—CH₂—OMe | " | " | E¹⁵ |
| 180 | 6-OPh | " | " | E¹⁵ |
| 181 | 6-OCH₂CF₃ | " | " | E¹⁵ |
| 182 | 6-OCH(CF₃)₂ | " | " | E¹⁵ |
| 183 | 6-CH₃ | " | " | E¹⁵ |
| 184 | 6-CH₂OMe | " | " | E¹⁵ |
| 185 | 6-SPh | " | " | E¹⁵ |
| 186 | 6-H | " | " | E¹⁶ |
| 187 | 6-Cl | " | " | E¹⁶ |
| 188 | 6-Br | " | " | E¹⁶ |
| 189 | 6-OMe | " | " | E¹⁶ |
| 190 | 6-OCH₂CH₃ | " | " | E¹⁶ |
| 191 | 6-O(CH₂)₂CH₃ | " | " | E¹⁶ |
| 192 | 6-OCH(CH₃)₂ | " | " | E¹⁶ |
| 193 | 6-OCH₂—CH(CH₃)₂ | " | " | E¹⁶ |
| 194 | 6-OCH₂CF₃ | " | " | E¹⁶ |
| 195 | 6-OCH(CF₃)₂ | " | " | E¹⁶ |
| 196 | 6-OPh | " | " | E¹⁶ |
| 197 | 6-SPh | " | " | E¹⁶ |
| 198 | 6-CH₃ | " | " | E¹⁶ |
| 199 | 6-CH₂OCH₃ | " | " | E¹⁶ |
| 200 | 6-H | " | " | E¹⁷ |
| 201 | 6-Cl | " | " | E¹⁷ |
| 202 | 6-Br | " | " | E¹⁷ |
| 203 | 6-OMe | " | " | E¹⁷ |
| 204 | 6-OCH₂CH₃ | " | " | E¹⁷ |
| 205 | 6-O(CH₂)₂CH₃ | " | " | E¹⁷ |
| 206 | 6-OCH(CH₃)₂ | " | " | E¹⁷ |
| 207 | 6-OCH₂—CH(CH₃)₂ | " | " | E¹⁷ |
| 208 | 6-OCH₂CF₃ | " | " | E¹⁷ |
| 209 | 6-OCH(CF₃)₂ | " | " | E¹⁷ |
| 210 | 6-OPh | " | " | E¹⁷ |
| 211 | 6-O—CH₂—CH₂—OMe | " | " | E¹⁷ |
| 212 | 6-SPh | " | " | E¹⁷ |
| 213 | 6-CH₃ | " | " | E¹⁷ |
| 214 | 6-CH₂OMe | " | " | E¹⁷ |
| 215 | 6-H | " | " | E¹⁸ |
| 216 | 6-Cl | " | " | E¹⁸ |
| 217 | 6-Br | " | " | E¹⁸ |
| 218 | 6-OCH₃ | " | " | E¹⁸ |
| 219 | 6-OCH₂CH₃ | " | " | E¹⁸ |
| 220 | 6-O(CH₂)₂CH₃ | " | " | E¹⁸ |
| 221 | 6-OCH(CH₃)₂ | " | " | E¹⁸ |
| 222 | 6-OCH₂—CH(CH₃)₂ | " | " | E¹⁸ |
| 223 | 6-OCH₂CF₃ | " | " | E¹⁸ |
| 224 | 6-OCH(CF₃)₂ | " | " | E¹⁸ |
| 225 | 6-O—CH₂—CH₂—OMe | " | " | E¹⁸ |
| 226 | 6-OPh | " | " | E¹⁸ |
| 227 | 6-SPh | " | " | E¹⁸ |
| 228 | 6-CH₃ | " | " | E¹⁸ |
| 229 | 6-CH₂OMe | " | " | E¹⁸ |
| 230 | 6-H | " | " | E¹⁹ |
| 231 | 6-Cl | " | " | E¹⁹ |
| 232 | 6-Br | " | " | E¹⁹ |
| 233 | 6-OMe | " | " | E¹⁹ |
| 234 | 6-OCH₂CH₃ | " | " | E¹⁹ |
| 235 | 6-O(CH₂)₂CH₃ | " | " | E¹⁹ |
| 236 | 6-O—CH(CH₃)₂ | " | " | E¹⁹ |
| 237 | 6-OCH₂—CH(CH₃)₂ | " | " | E¹⁹ |
| 238 | 6-OCH₂CF₃ | " | " | E¹⁹ |
| 239 | 6-OCH(CF₃)₂ | " | " | E¹⁹ |

TABLE 1-continued $$R^1-Ar^1-\underset{\underset{R}{|}}{C}=N\sim O-CH_2-Ar^2$$

| No. | $R^1$ | $Ar^1$ | R | $Ar^2$ |
|---|---|---|---|---|
| 240 | 6-O—CH$_2$—CH$_2$—OMe | " | " | E$^{19}$ |
| 241 | 6-OPh | " | " | E$^{19}$ |
| 242 | 6-CH$_3$ | " | " | E$^{19}$ |
| 243 | 6-SPh | " | " | E$^{19}$ |
| 244 | 6-Cl | " | " | E$^{60}$ |
| 245 | 6-OCH$_2$CF$_3$ | " | " | E$^{60}$ |
| 246 | 6-Cl | " | " | E$^{61}$ |
| 247 | 6-OCH$_2$CF$_3$ | " | " | E$^{61}$ |
| 248 | 6-Cl | " | " | E$^{20}$ |
| 249 | 6-OCH$_2$CH$_3$ | " | " | E$^{20}$ |
| 250 | 6-OCH$_2$CF$_3$ | " | " | E$^{20}$ |
| 251 | 6-Cl | " | " | E$^{21}$ |
| 252 | 6-OCH$_2$CF$_3$ | " | " | E$^{21}$ |
| 253 | 6-Cl | " | " | E$^{22}$ |
| 254 | 6-OCH$_2$CH$_3$ | " | " | E$^{22}$ |
| 255 | 6-OCH$_2$CF$_3$ | " | " | E$^{22}$ |
| 256 | 6-Cl | " | " | E$^{23}$ |
| 257 | 6-OCH$_2$CH$_3$ | " | " | E$^{23}$ |
| 258 | 6-OCH$_2$CF$_3$ | " | " | E$^{23}$ |
| 259 | 6-Cl | " | " | E$^{24}$ |
| 260 | 6-OCH$_2$CH$_3$ | " | " | E$^{24}$ |
| 261 | 6-OCH$_2$CF$_3$ | " | " | E$^{24}$ |
| 262 | 6-Cl | " | " | E$^{25}$ |
| 263 | 6-OCH$_2$CH$_2$CH$_3$ | " | " | E$^{25}$ |
| 264 | 6-OCH$_2$CF$_3$ | " | " | E$^{25}$ |
| 265 | 6-Cl | " | " | E$^{26}$ |
| 266 | 6-OCH$_2$CH$_3$ | " | " | E$^{26}$ |
| 267 | 6-OCH$_2$CF$_3$ | " | " | E$^{26}$ |
| 268 | 6-Cl | " | " | E$^{27}$ |
| 269 | 6-OCH$_2$CH$_3$ | " | " | E$^{27}$ |
| 270 | 6-OCH$_2$CF$_3$ | " | " | E$^{27}$ |
| 271 | 6-Cl | " | " | E$^{28}$ |
| 272 | 6-OCH$_2$CH$_3$ | " | " | E$^{28}$ |
| 273 | 6-OCH$_2$CF$_3$ | " | " | E$^{28}$ |
| 274 | 6-Cl | " | " | E$^{29}$ |
| 275 | 6-O—CH$_2$CH$_2$CH$_3$ | " | " | E$^{29}$ |
| 276 | 6-O—CH$_2$CF$_3$ | " | " | E$^{29}$ |
| 277 | 6-Cl | " | " | E$^{30}$ |
| 278 | 6-OCH$_2$CH$_2$CH$_3$ | " | " | E$^{30}$ |
| 279 | 6-OCH$_2$CF$_3$ | " | " | E$^{30}$ |
| 280 | 6-Cl | " | " | E$^{52}$ |
| 281 | 6-OCH$_2$CH$_2$CH$_3$ | " | " | E$^{52}$ |
| 282 | 6-OCH$_2$CF$_3$ | " | " | E$^{52}$ |
| 283 | 6-Cl | " | " | E$^{32}$ |
| 284 | 6-OCH$_2$CH$_2$CH$_3$ | " | " | E$^{32}$ |
| 285 | 6-OCH$_2$CF$_3$ | " | " | E$^{32}$ |
| 286 | 6-Cl | " | " | E$^{33}$ |
| 287 | 6-OCH$_2$CH$_2$CH$_3$ | " | " | E$^{33}$ |
| 288 | 6-OCH$_2$CF$_3$ | " | " | E$^{33}$ |
| 289 | 6-H | " | " | E$^{34}$ |
| 290 | 6-Cl | " | " | E$^{34}$ |
| 291 | 6-OCH$_3$ | " | " | E$^{34}$ |
| 292 | 6-OCH$_2$CH$_3$ | " | " | E$^{34}$ |
| 293 | 6-OCH$_2$CH$_2$CH$_3$ | " | " | E$^{34}$ |
| 294 | 6-OCH(CH$_3$)$_2$ | " | " | E$^{34}$ |
| 295 | 6-O(CH$_2$)$_3$CH$_3$ | " | " | E$^{34}$ |
| 296 | 6-OCH$_2$—CH(CH$_3$)$_2$ | " | " | E$^{34}$ |
| 297 | 6-O(CH$_2$)$_5$CH$_3$ | " | " | E$^{34}$ |
| 298 | 6-cyclopentyloxy | " | " | E$^{34}$ |
| 299 | 6-O—CH$_2$—CH$_2$—OMe | " | " | E$^{34}$ |
| 300 | 6-O—CH$_2$—CH=CH$_2$ | " | " | E$^{34}$ |
| 301 | 6-OPh | " | " | E$^{34}$ |
| 302 | 6-OCH$_2$CF$_3$ | " | " | E$^{34}$ |
| 303 | 6-OCH(CF$_3$)$_2$ | " | " | E$^{34}$ |
| 304 | 6-SMe | " | " | E$^{34}$ |
| 305 | 6-SPh | " | " | E$^{34}$ |
| 306 | 6-CH$_3$ | " | " | E$^{34}$ |
| 307 | 6-CH$_2$OMe | " | " | E$^{34}$ |
| 308 | 6-CH$_2$NMe | " | " | E$^{34}$ |
| 309 | 6-Cl | " | " | E$^{35}$ |
| 310 | 6-Br | " | " | E$^{35}$ |
| 311 | 6-OMe | " | " | E$^{35}$ |
| 312 | 6-OCH$_2$CH$_3$ | " | " | E$^{35}$ |

TABLE 1-continued $$R^1-Ar^1-\underset{\underset{\|}{R}}{C}=N\sim O-CH_2-Ar^2$$

| No. | R¹ | Ar¹ | R | Ar² |
|---|---|---|---|---|
| 313 | 6-OCH₂CH₂CH₃ | " | " | E³⁵ |
| 314 | 6-OCH(CH₃)₂ | " | " | E³⁵ |
| 315 | 6-O(CH₂)₃CH₃ | " | " | E³⁵ |
| 316 | 6-O—CH₂—CH(CH₃)₂ | " | " | E³⁵ |
| 317 | 6-O—CH₂—CH₂—OCH₃ | " | " | E³⁵ |
| 318 | 6-OPh | " | " | E³⁵ |
| 319 | 6-OCH₂CF₃ | " | " | E³⁵ |
| 320 | 6-OCH(CF₃)₂ | " | " | E³⁵ |
| 321 | 6-CH₃ | " | " | E³⁵ |
| 322 | 6-CH₂OMe | " | " | E³⁵ |
| 323 | 6-H | " | " | E³⁶ |
| 324 | 6-Cl | " | " | E³⁶ |
| 325 | 6-Br | " | " | E³⁶ |
| 326 | 6-OCH₃ | " | " | E³⁶ |
| 327 | 6-OCH₂CH₃ | " | " | E³⁶ |
| 328 | 6-OCH₂CH₂CH₃ | " | " | E³⁶ |
| 329 | 6-OCH(CH₃)₂ | " | " | E³⁶ |
| 330 | 6-OCH₂CH(CH₃)₂ | " | " | E³⁶ |
| 331 | 6-O(CH₂)₅CH₃ | " | " | E³⁶ |
| 332 | 6-cyclopentyloxy | " | " | E³⁶ |
| 333 | 6-OCH₂CF₃ | " | " | E³⁶ |
| 334 | 6-O—CH(CF₃)₂ | " | " | E³⁶ |
| 335 | 6-OPh | " | " | E³⁶ |
| 336 | 6-O—CH₂—CH₂—OMe | " | " | E³⁶ |
| 337 | 6-SMe | " | " | E³⁶ |
| 338 | 6-SPh | " | " | E³⁶ |
| 339 | 6-CH₃ | " | " | E³⁶ |
| 340 | 6-CH₂OCH₃ | " | " | E³⁶ |
| 341 | 6-CH₂NMe₂ | " | " | E³⁶ |
| 342 | 6-CH₂SMe | " | " | E³⁶ |
| 343 | 6-H | " | " | E³⁷ |
| 344 | 6-OCH₃ | " | " | E³⁷ |
| 345 | 6-OCH₂CH₃ | " | " | E³⁷ |
| 346 | 6-OCH₂CH₂CH₃ | " | " | E³⁷ |
| 347 | 6-OCH(CH₃)₂ | " | " | E³⁷ |
| 348 | 6-OCH₂CH(CH₃)₂ | " | " | E³⁷ |
| 349 | 6-O-cyclopentyloxy | " | " | E³⁷ |
| 350 | 6-OCH₂CF₃ | " | " | E³⁷ |
| 351 | 6-OCH(CF₃)₂ | " | " | E³⁷ |
| 352 | 6-O—CH₂—CH₂—OMe | " | " | E³⁷ |
| 353 | 6-OPh | " | " | E³⁷ |
| 354 | 6-SMe | " | " | E³⁷ |
| 355 | 6-SPh | " | " | E³⁷ |
| 356 | 6-NMe₂ | " | " | E³⁷ |
| 357 | 6-NHPh | " | " | E³⁷ |
| 358 | 6-CH₃ | " | " | E³⁷ |
| 359 | 6-CH₂OMe | " | " | E³⁷ |
| 360 | 6-CH₂NMe₂ | " | " | E³⁷ |
| 361 | 6-H | 2-pyridyl | CF₃ | E¹ |
| 362 | " | " | " | E⁸ |
| 363 | | | | E⁹ |
| 364 | | | | E¹⁰ |
| 365 | | | | E³⁴ |
| 366 | | | | E³⁶ |
| 367 | 6-OCH₂CH₃ | " | " | E¹ |
| 368 | " | " | " | E⁸ |
| 369 | " | " | " | E⁹ |
| 370 | 6-OCH₂CH₃ | " | " | E¹⁰ |
| 371 | " | " | " | E³⁶ |
| 372 | 6-OCH₂CF₃ | " | " | E¹ |
| 373 | " | " | " | E⁸ |
| 374 | " | " | " | E⁹ |
| 375 | " | " | " | E¹⁰ |
| 376 | " | " | " | E³⁴ |
| 377 | " | " | " | E³⁶ |
| 378 | 6-OPh | " | " | E¹ |
| 379 | " | " | " | E⁸ |
| 380 | " | " | " | E⁹ |
| 381 | " | " | " | E¹⁰ |
| 382 | " | " | " | E³⁴ |
| 383 | " | " | " | E³⁶ |
| 384 | 6-H | 4-pyridyl | CF₃ | E¹ |
| 385 | " | " | " | E⁸ |

TABLE 1-continued $$R^1-Ar^1-\underset{\underset{R}{|}}{C}=N\sim O-CH_2-Ar^2$$

| No. | R¹ | Ar¹ | R | Ar² |
|---|---|---|---|---|
| 386 | " | " | " | E⁹ |
| 387 | " | " | " | E¹⁰ |
| 388 | " | " | " | E³⁴ |
| 389 | " | " | " | E³⁶ |
| 390 | 6-OEt | " | " | E¹ |
| 391 | 6-OEt | " | " | E⁸ |
| 392 | 6-OEt | " | " | E⁹ |
| 393 | " | " | " | E¹⁰ |
| 394 | " | " | " | E³⁴ |
| 395 | " | " | " | E³⁶ |
| 396 | 6-OCH₂CF₃ | 3-pyridyl | CH₃ | E¹ |
| 397 | " | " | " | E⁸ |
| 398 | " | " | " | E⁹ |
| 399 | " | " | " | E¹⁰ |
| 400 | " | " | " | E³⁴ |
| 401 | 6-OCH₂CF₃ | " | " | E³⁶ |
| 402 | " | " | CH(CH₃)₂ | E¹ |
| 403 | " | " | " | E² |
| 404 | " | " | " | E³ |
| 405 | " | " | " | E⁸ |
| 406 | " | " | " | E⁹ |
| 407 | " | " | " | E¹⁰ |
| 408 | " | " | " | E¹³ |
| 409 | " | " | " | E¹⁴ |
| 410 | " | " | " | E¹⁸ |
| 411 | 6-OCH₂CF₃ | " | " | E¹⁹ |
| 412 | " | " | " | E¹¹ |
| 413 | " | " | " | E¹⁵ |
| 414 | 6-OCH₂CF₃ | " | " | E¹⁷ |
| 415 | " | " | " | E³⁴ |
| 416 | " | " | " | E³⁶ |
| 417 | 6-OCH₃ | " | " | E⁸ |
| 418 | " | " | " | E⁹ |
| 419 | " | " | " | E¹⁰ |
| 420 | " | " | " | E¹⁴ |
| 421 | " | " | " | E¹¹ |
| 422 | " | " | " | E¹⁷ |
| 423 | " | " | " | E¹⁸ |
| 424 | " | " | " | E¹⁹ |
| 425 | " | " | " | E¹⁵ |
| 426 | " | " | " | E¹⁶ |
| 427 | " | " | " | E³⁴ |
| 428 | " | " | " | E³⁶ |
| 429 | 6-OCH₂CH₃ | " | " | E⁸ |
| 430 | " | " | " | E⁹ |
| 431 | " | " | " | E¹⁰ |
| 432 | " | " | " | E¹¹ |
| 433 | " | " | " | E¹² |
| 434 | " | " | " | E¹⁵ |
| 435 | " | " | " | E¹⁶ |
| 436 | 6-OCH₂CH₃ | " | " | E³⁶ |
| 437 | 6-Cl | " | " | E⁸ |
| 438 | " | " | " | E⁹ |
| 439 | " | " | " | E¹⁰ |
| 440 | " | " | " | E¹¹ |
| 441 | " | " | " | E¹² |
| 442 | " | " | " | E¹⁵ |
| 443 | " | " | " | E¹⁶ |
| 444 | " | " | " | E¹⁸ |
| 445 | " | " | " | E¹⁹ |
| 446 | " | " | " | E³⁶ |
| 447 | 6-OPh | " | " | E⁸ |
| 448 | " | " | " | E⁹ |
| 449 | " | " | " | E¹⁰ |
| 450 | " | " | " | E¹¹ |
| 451 | 6-Cl | " | CF₃ | E³⁹ |
| 452 | 6-OCH₂CH₃ | " | " | E³⁹ |
| 453 | 6-OCH₂CH₂CH₃ | " | " | E³⁹ |
| 454 | 6-OCH₂CF₃ | " | " | E³⁹ |
| 455 | 6-Cl | " | " | E⁴⁰ |
| 456 | 6-OCH₂CH₃ | " | " | E⁴⁰ |
| 457 | 6-OCH₂CH₂CH₃ | " | " | E⁴⁰ |
| 458 | 6-OCH₂CF₃ | " | " | E⁴⁰ |

TABLE 1-continued $$R^1-Ar^1-\overset{\overset{R}{|}}{C}=N\sim O-CH_2-Ar^2$$

| No. | R¹ | Ar¹ | R | Ar² |
|---|---|---|---|---|
| 459 | 6-Cl | " | " | E⁴¹ |
| 460 | 6-OCH₂CF₃ | " | " | E⁴¹ |
| 461 | 6-OCH₂CH₂CH₃ | " | " | E⁴¹ |
| 462 | 6-Cl | " | " | E⁴² |
| 463 | 6-OCH₂CH₃ | " | " | E⁴² |
| 464 | 6-OCH₂CH₂CH₃ | " | " | E⁴² |
| 465 | 6-OCH₂CF₃ | " | " | E⁴² |
| 466 | 6-Cl | " | " | E⁴³ |
| 467 | 6-OCH₂CH₃ | " | " | E⁴³ |
| 468 | 6-OCH₂CH₂CH₃ | " | " | E⁴³ |
| 469 | 6-OCH₂CF₃ | " | " | E⁴³ |
| 470 | 6-Cl | " | " | E⁴⁴ |
| 471 | 6-N-morpholino | " | " | E⁴⁴ |
| 472 | 6-OCH₂CH₂CH₃ | " | " | E⁴⁴ |
| 473 | 6-OCH₂CF₃ | " | " | E⁴⁴ |
| 474 | 6-OCH₂CF₃ | " | " | E⁴⁵ |
| 475 | 6-Cl | " | " | E⁴⁶ |
| 476 | 6-OCH₂CH₃ | " | " | E⁴⁶ |
| 477 | 6-OCH₂CH₂CH₃ | " | " | E⁴⁶ |
| 478 | 6-OCH₂CF₃ | " | " | E⁴⁶ |
| 479 | 6-Cl | " | " | E⁴⁷ |
| 480 | 6-OCH₂CF₃ | " | " | E⁴⁸ |
| 481 | 6-OCH₂CF₃ | " | " | E⁴⁷ |
| 482 | 6-Cl | " | " | E⁴⁹ |
| 483 | 6-OCH₂CH₃ | " | " | E⁴⁹ |
| 484 | 6-OCH₂CH₂CH₃ | " | " | E⁴⁹ |
| 485 | 6-OCH₂CF₃ | " | " | E⁴⁹ |
| 486 | 6-Cl | " | " | E⁵⁰ |
| 487 | 6-OCH₂CH₃ | " | " | E⁵⁰ |
| 488 | 6-OCH₂CH₂CH₃ | " | " | E⁵⁰ |
| 489 | 6-OCH₂CF₃ | " | " | E⁵⁰ |
| 490 | 6-Cl | " | " | E⁵¹ |
| 491 | 6-OCH₂CH₃ | " | " | E⁵¹ |
| 492 | 6-OCH₂CH₂CH₃ | " | " | E⁵¹ |
| 493 | 6-OCH₂CF₃ | " | " | E⁵¹ |
| 494 | 6-Cl | " | " | E²⁸ |
| 495 | 6-OCH₂CH₃ | " | " | E²⁸ |
| 496 | 6-OCH₂CH₂CH₃ | " | " | E²⁸ |
| 497 | 6-OCH₂CF₃ | " | " | E²⁸ |
| 498 | 6-Cl | " | " | E⁵⁵ |
| 499 | 6-OCH₂CH₃ | " | " | E⁵⁵ |
| 500 | 6-OCH₂CH₂CH₃ | " | " | E⁵⁵ |
| 501 | 6-OCH₂CF₃ | " | " | E⁵⁵ |
| 502 | 6-Cl | " | " | E³⁸ |
| 503 | 6-Br | " | " | E³⁸ |
| 504 | 6-OMe | " | " | E³⁸ |
| 505 | 6-OCH₂CH₃ | " | " | E³⁸ |
| 506 | 6-OCH₂CH₂CH₃ | " | " | E³⁸ |
| 507 | 6-OCH₂CF₃ | " | " | E³⁸ |
| 508 | 6-O=CH₂=CH₂=OMe | " | " | E³⁸ |
| 509 | 6-OCH₃ | " | " | E³⁸ |
| 510 | 6-OCH₂OMe | " | " | E³⁸ |
| 511 | 6-Cl | " | " | E⁵³ |
| 512 | 6-OCH₂CH₃ | " | " | E⁵³ |
| 513 | 6-OCH₂CH₂CH₃ | " | " | E⁵³ |
| 514 | 6-OCH₂CF₃ | " | " | E⁵³ |
| 515 | 6-Cl | " | " | E⁵⁴ |
| 516 | 6-OCH₂CH₃ | " | " | E⁵⁴ |
| 517 | 6-OCH₂CH₂CH₃ | " | " | E⁵⁴ |
| 518 | 6-OCH₂CF₃ | " | " | E⁵⁴ |
| 519 | 6-OPh | " | CH(CH₃)₂ | E¹⁵ |
| 520 | " | " | " | E¹⁶ |
| 521 | " | " | " | E³⁶ |
| 522 | 6-OCH₂CF₃ | " | " | E⁵¹ |
| 523 | 6-OCH(CF₃)₂ | " | " | E⁵¹ |
| 524 | 6-OCH₂CF₃ | " | " | E³⁸ |
| 525 | 6-OCH(CF₃)₂ | " | " | E³⁸ |
| 526 | 2-Cl | 5-pyrimidinyl | CF₃ | E² |
| 527 | 2-Br | " | " | E² |
| 528 | 2-OMe | " | " | E² |
| 529 | 2-OCH₂CH₃ | " | " | E² |
| 530 | 2-OCH₂CH₂CH₃ | " | " | E² |
| 531 | 2-OCH(CH₃)₂ | " | " | E² |

TABLE 1-continued $$R^1-Ar^1-\underset{\underset{R}{|}}{C}=N\sim O-CH_2-Ar^2$$

| No. | R¹ | Ar¹ | R | Ar² |
|---|---|---|---|---|
| 532 | 2-O(CH₂)₅CH₃ | " | " | E² |
| 533 | 2-OCH₂CH₂OMe | " | " | E² |
| 534 | 2-O—CH₂—CH=CH₂ | " | " | E² |
| 535 | 2-OPh | " | " | E² |
| 536 | 2-OCH₂CF₃ | " | " | E² |
| 537 | 2-OCH(CF₃)₂ | " | " | E² |
| 538 | 2-SCH₃ | " | " | E² |
| 539 | 2-SCH₂CH₃ | " | " | E² |
| 540 | 2-SPh | " | " | E² |
| 541 | 2-NHPh | " | " | E² |
| 542 | 2-NMe₂ | " | " | E² |
| 543 | 2-CH₃ | " | " | E² |
| 544 | 2-CH₂OCH₃ | " | " | E² |
| 545 | 2-PH | " | " | E² |
| 546 | 2-Cl | " | " | E¹ |
| 547 | 2-OMe | " | " | E¹ |
| 548 | 2-OCH₂CH₃ | " | " | E¹ |
| 549 | 2-OCH₂CH₂CH₃ | " | " | E¹ |
| 550 | 2-OCH(CH₃)₂ | " | " | E¹ |
| 551 | 2-O(CH₂)₅CH₃ | " | " | E¹ |
| 552 | 2-OCH₂CH₂OMe | " | " | E¹ |
| 553 | 2-OPh | " | " | E¹ |
| 554 | 2-OCH₂CF₃ | " | " | E¹ |
| 555 | 2-OCH(CF₃)₂ | " | " | E¹ |
| 556 | 2-S—CH₃ | " | " | E¹ |
| 557 | 2-S—Ph | " | " | E¹ |
| 558 | 2-NHPh | " | " | E¹ |
| 559 | 2-NMe₂ | " | " | E¹ |
| 560 | 2-CH₃ | " | " | E¹ |
| 561 | 2-SMe | " | " | E⁷ |
| 562 | 2-S—Ph | " | " | E⁷ |
| 563 | 2-CH₃ | " | " | E⁷ |
| 564 | 2-Cl | " | " | E³ |
| 565 | 2-Br | " | " | E³ |
| 566 | 2-OMe | " | " | E³ |
| 567 | 2-OCH₂CH₃ | " | " | E³ |
| 568 | 2-OCH₂CH₂CH₃ | " | " | E³ |
| 569 | 2-OCH(CH₃)₂ | " | " | E³ |
| 570 | 2-O(CH₂)₂CH₃ | " | " | E³ |
| 571 | 2-OCH₂CF₃ | " | " | E³ |
| 572 | 2-OCH(CF₃)₂ | " | " | E³ |
| 573 | 2-Cl | " | " | E⁸ |
| 574 | 2-Br | " | " | E⁸ |
| 575 | 2-OMe | " | " | E⁸ |
| 576 | 2-OCH₂CH₃ | " | " | E⁸ |
| 577 | 2-OCH(CH₃)₂ | " | " | E⁸ |
| 578 | 2-O(CH₂)₅CH₃ | " | " | E⁸ |
| 579 | 2-OPh | " | " | E⁸ |
| 580 | 2-OCH₂CF₃ | " | " | E⁸ |
| 581 | 2-OCH(CF₃)₂ | " | " | E⁸ |
| 582 | 2-OCH₂CH₂OMe | " | " | E⁸ |
| 583 | 2-Cl | " | " | E⁹ |
| 584 | 2-Br | " | " | E⁹ |
| 585 | 2-OMe | " | " | E⁹ |
| 586 | 2-OCH₂CH₃ | " | " | E⁹ |
| 587 | 2-OCH₂CH₂CH₃ | " | " | E⁹ |
| 588 | 2-OCH(CH₃)₂ | " | " | E⁹ |
| 589 | 2-O(CH₂)₂CH₃ | " | " | E⁹ |
| 590 | 2-OPh | " | " | E⁹ |
| 591 | 2-OCH₂CF₃ | " | " | E⁹ |
| 592 | 2-OCH(CF₃)₂ | " | " | E⁹ |
| 593 | 2-SPh | " | " | E⁹ |
| 594 | 2-SMe | " | " | E⁹ |
| 595 | 2-CH₃ | " | " | E⁹ |
| 596 | 2-Cl | " | " | E¹⁰ |
| 597 | 2-Br | " | " | E¹⁰ |
| 598 | 2-OMe | " | " | E¹⁰ |
| 599 | 2-OCH₂CH₃ | " | " | E¹⁰ |
| 600 | 2-OCH₂CH₂CH₃ | " | " | E¹⁰ |
| 601 | 2-OCH(CH₃)₂ | " | " | E¹⁰ |
| 602 | 2-OPh | " | " | E¹⁰ |
| 603 | 2-OCH₂CF₃ | " | " | E¹⁰ |
| 604 | 2-OCH(CF₃)₂ | " | " | E¹⁰ |

TABLE 1-continued $$R^1-Ar^1-\overset{R}{\underset{|}{C}}=N\sim O-CH_2-Ar^2$$

| No. | R¹ | Ar¹ | R | Ar² |
|---|---|---|---|---|
| 605 | 2-O—CH₂—CH₂—OMe | " | " | E¹⁰ |
| 606 | 2-SPh | " | " | E¹⁰ |
| 607 | 2-S—CH₃ | " | " | E¹⁰ |
| 608 | 2-Me | " | " | E¹⁰ |
| 609 | 2-tBu | " | " | E¹⁰ |
| 610 | 2-Cl | " | " | E¹¹ |
| 611 | 2-OMe | " | " | E¹¹ |
| 612 | 2-OCH₂CH₃ | " | " | E¹¹ |
| 613 | 2-OCHCH₂CH₃ | " | " | E¹¹ |
| 614 | 2-OCH(CH₃)₂ | " | " | E¹¹ |
| 615 | 2-OCH₂CF₃ | " | " | E¹¹ |
| 616 | 2-OCH(CF₃)₂ | " | " | E¹¹ |
| 617 | 2-O—CH₂—CH₂—OMe | " | " | E¹¹ |
| 618 | 2-SPh | " | " | E¹¹ |
| 619 | 2-Me | " | " | E¹¹ |
| 620 | 2-tBu | " | " | E¹¹ |
| 621 | 2-Cl | " | " | E¹⁹ |
| 622 | 2-OMe | " | " | E¹⁹ |
| 623 | 2-OCH₂CH₃ | " | " | E¹⁹ |
| 624 | 2-OCH₂CH₂CH₃ | " | " | E¹⁹ |
| 625 | 2-OCH(CH₃)₂ | " | " | E¹⁹ |
| 626 | 2-O—CH₂—CH₂—OMe | " | " | E¹⁹ |
| 627 | 2-OCH₂CF₃ | " | " | E¹⁹ |
| 628 | 2-OCH(CF₃)₂ | " | " | E¹⁹ |
| 629 | 2-OPh | " | " | E¹⁹ |
| 630 | 2-SMe | " | " | E¹⁹ |
| 631 | 2-SPh | " | " | E¹⁹ |
| 632 | 2-Me | " | " | E¹⁹ |
| 633 | 2-tBu | " | " | E¹⁹ |
| 634 | 2-Cl | " | " | E¹⁶ |
| 635 | 2-OMe | " | " | E¹⁶ |
| 636 | 2-OCH₂CH₃ | " | " | E¹⁶ |
| 637 | 2-OCH₂CH₂CH₃ | " | " | E¹⁶ |
| 638 | 2-OCH(CH₃)₂ | " | " | E¹⁶ |
| 639 | 2-OCH₂CF₃ | " | " | E¹⁶ |
| 640 | 2-OCH(CF₃)₂ | " | " | E¹⁶ |
| 641 | 2-O—CH₂—CH₂—Me | " | " | E¹⁶ |
| 642 | 2-OPh | " | " | E¹⁶ |
| 643 | 2-SPh | " | " | E¹⁶ |
| 644 | 2-tBu | " | " | E¹⁶ |
| 645 | 2-Me | " | " | E¹⁶ |
| 646 | 2-Cl | " | " | E¹⁵ |
| 647 | 2-OCH₃ | " | " | E¹⁵ |
| 648 | 2-OCH₂CH₃ | " | " | E¹⁵ |
| 649 | 2-OCH₂CH₂CH₃ | " | " | E¹⁵ |
| 650 | 2-OCH(CH₃)₂ | " | " | E¹⁵ |
| 651 | 2-OCH₂CF₃ | " | " | E¹⁵ |
| 652 | 2-OCH(CF₃)₂ | " | " | E¹⁵ |
| 653 | 2-OPh | " | " | E¹⁵ |
| 654 | 2-SPh | " | " | E¹⁵ |
| 655 | 2-Me | " | " | E¹⁵ |
| 656 | 2-tBu | " | " | E¹⁵ |
| 657 | 2-Cl | " | " | E³⁸ |
| 658 | 2-Br | " | " | E³⁸ |
| 659 | 2-OMe | " | " | E³⁸ |
| 660 | 2-OCH₂CH₃ | " | " | E³⁸ |
| 661 | 2-OCH₂CH₂CH₃ | " | " | E³⁸ |
| 662 | 2-OCH(CH₃)₂ | " | " | E³⁸ |
| 663 | 2-OCH₂CF₃ | " | " | E³⁸ |
| 664 | 2-OCH(CF₃)₂ | " | " | E³⁸ |
| 665 | 2-O—CH₂—CH₂—OMe | " | " | E³⁸ |
| 666 | 2-OPh | " | " | E³⁸ |
| 667 | 2-SPh | " | " | E³⁸ |
| 668 | 2-SMe | " | " | E³⁸ |
| 669 | 2-CH₃ | " | " | E³⁸ |
| 670 | 2-tBu | " | " | E³⁸ |
| 671 | 2-Cl | " | " | E³⁴ |
| 672 | 2-Br | " | " | E³⁴ |
| 673 | 2-OMe | " | " | E³⁴ |
| 674 | 2-OCH₂CH₃ | " | " | E³⁴ |
| 675 | 2-OCH₂CH₂CH₃ | " | " | E³⁴ |
| 676 | 2-OCH(CH₃)₂ | " | " | E³⁴ |
| 677 | 2-OCH₂CF₃ | " | " | E³⁴ |

TABLE 1-continued $$R^1-Ar^1-\underset{\underset{R}{|}}{C}=N\sim O-CH_2-Ar^2$$

| No. | R¹ | Ar¹ | R | Ar² |
|---|---|---|---|---|
| 678 | 2-OCH(CF₃)₂ | " | " | E³⁴ |
| 679 | 2-O—CH₂—CH₂—OMe | " | " | E³⁴ |
| 680 | 2-OPh | " | " | E³⁴ |
| 681 | 2-SPh | " | " | E³⁴ |
| 682 | 2-CH₃ | " | " | E³⁴ |
| 683 | 2-tBu | " | " | E³⁴ |
| 684 | 2-Cl | " | " | E³⁶ |
| 685 | 2-Br | " | " | E³⁶ |
| 686 | 2-OMe | " | " | E³⁶ |
| 687 | 2-OCH₂CH₃ | " | " | E³⁶ |
| 688 | 2-OCH₂CH₂CH₃ | " | " | E³⁶ |
| 689 | 2-OCH(CH₃)₂ | " | " | E³⁶ |
| 690 | 2-OCH₂CF₃ | " | " | E³⁶ |
| 691 | 2-OCH(CF₃)₂ | " | " | E³⁶ |
| 692 | 2-OPh | " | " | E³⁶ |
| 693 | 2-SPh | " | " | E³⁶ |
| 694 | 2-Me | " | " | E³⁶ |
| 695 | 2-tBu | " | " | E³⁶ |
| 696 | 2-Cl | " | CH(CH₃)₂ | E⁸ |
| 697 | 2-OMe | " | " | E⁸ |
| 698 | 2-OCH₂CH₃ | " | " | E⁸ |
| 699 | 2-OCH₂CH₂CH₃ | " | " | E⁸ |
| 700 | 2-OCH(CH₃)₂ | " | " | E⁸ |
| 701 | 2-OCH₂CF₃ | " | " | E⁸ |
| 702 | 2-OCH(CF₃)₂ | " | " | E⁸ |
| 703 | 2-OPh | " | " | E⁸ |
| 704 | 2-SPh | " | " | E⁸ |
| 705 | 2-SMe | " | " | E⁸ |
| 706 | 2-Me | " | " | E⁸ |
| 707 | 2-tBu | " | " | E⁸ |
| 708 | 2-Cl | " | " | E⁹ |
| 709 | 2-Br | " | " | E⁹ |
| 710 | 2-OMe | " | " | E⁹ |
| 711 | 2-OCH₂CH₃ | " | " | E⁹ |
| 712 | 2-OCH₂CH₂CH₃ | " | " | E⁹ |
| 713 | 2-OCH—CH₃ | " | " | E⁹ |
| 714 | 2-OCH₂CF₃ | " | " | E⁹ |
| 715 | 2-OCH(CF₃)₂ | " | " | E⁹ |
| 716 | 2-OPh | " | " | E⁹ |
| 717 | 2-SPh | " | " | E⁹ |
| 718 | 2-Cl | " | " | E¹⁰ |
| 719 | 2-Br | " | " | E¹⁰ |
| 720 | 2-OMe | " | " | E¹⁰ |
| 721 | 2-OCH₂CH₃ | " | " | E¹⁰ |
| 722 | 2-OCH₂CH₂CH₃ | " | " | E¹⁰ |
| 723 | 2-OCH(CH₃)₂ | " | " | E¹⁰ |
| 724 | 2-OCH₂CF₃ | " | " | E¹⁰ |
| 725 | 2-OCH(CF₃)₂ | " | " | E¹⁰ |
| 726 | 2-OPh | " | " | E¹⁰ |
| 727 | 2-SPh | " | " | E¹⁰ |
| 728 | 2-Me | " | " | E¹⁰ |
| 729 | 2-tBu | " | " | E¹⁰ |
| 730 | 2-OCH₂CF₃ | " | " | E³⁴ |
| 731 | 2-Cl | " | " | E³⁶ |
| 732 | 2-OMe | " | " | E³⁶ |
| 733 | 2-OCH₂CH₃ | " | " | E³⁶ |
| 734 | 2-OCH₂CH₂CH₃ | " | " | E³⁶ |
| 735 | 2-OCH(CH₃)₂ | " | " | E³⁶ |
| 736 | 2-OCH₂CF₃ | " | " | E³⁶ |
| 737 | 2-OCH(CF₃)₂ | " | " | E³⁶ |
| 738 | 2-OPh | " | " | E³⁶ |
| 739 | 2-SPh | " | " | E³⁶ |
| 740 | 2-Me | " | " | E³⁶ |
| 741 | 2-tBu | " | " | E³⁶ |
| 742 | 2-Cl | 5-thiazolyl | CF₃ | E² |
| 743 | " | " | " | E¹ |
| 744 | 2-Cl | " | " | E⁷ |
| 745 | " | " | " | E⁶ |
| 746 | " | " | " | E⁵ |
| 747 | " | " | " | E³ |
| 748 | " | " | " | E⁸ |
| 749 | " | " | " | E⁹ |
| 750 | " | " | " | E¹⁰ |

TABLE 1-continued $$R^1-Ar^1-\underset{\underset{R}{|}}{C}=N\sim O-CH_2-Ar^2$$

| No. | R¹ | Ar¹ | R | Ar² |
|---|---|---|---|---|
| 751 | " | " | " | $E^{11}$ |
| 752 | " | " | " | $E^{18}$ |
| 753 | " | " | " | $E^{17}$ |
| 754 | " | " | " | $E^{16}$ |
| 755 | " | " | " | $E^{15}$ |
| 756 | " | " | " | $E^{38}$ |
| 757 | " | " | " | $E^{34}$ |
| 758 | " | " | " | $E^{36}$ |
| 759 | 4-H | phenyl | $CF_3$ | $E^7$ |
| 760 | " | " | " | $E^6$ |
| 761 | " | " | " | $E^5$ |
| 762 | " | " | " | $E^3$ |
| 763 | " | " | " | $E^{17}$ |
| 764 | " | " | " | $E^9$ |
| 765 | " | " | " | $E^{10}$ |
| 766 | 4-H | " | " | $E^{11}$ |
| 767 | " | " | " | $E^{12}$ |
| 768 | " | " | " | $E^{18}$ |
| 769 | " | " | " | $E^{16}$ |
| 770 | " | " | " | $E^{15}$ |
| 771 | " | " | " | $E^{38}$ |
| 772 | " | " | " | $E^{36}$ |
| 773 | 4-Cl | " | " | $E^7$ |
| 774 | " | " | " | $E^6$ |
| 775 | " | " | " | $E^5$ |
| 776 | " | " | " | $E^3$ |
| 777 | " | " | " | $E^{17}$ |
| 778 | " | " | " | $E^9$ |
| 779 | " | " | " | $E^{10}$ |
| 780 | " | " | " | $E^{11}$ |
| 781 | " | " | " | $E^{12}$ |
| 782 | " | " | " | $E^{18}$ |
| 783 | " | " | " | $E^{16}$ |
| 784 | " | " | " | $E^{15}$ |
| 785 | " | " | " | $E^{38}$ |
| 786 | " | " | " | $E^{36}$ |
| 787 | 4-Br | " | " | $E^7$ |
| 788 | 4-Br | " | " | $E^6$ |
| 789 | " | " | " | $E^5$ |
| 790 | " | " | " | $E^3$ |
| 791 | " | " | " | $E^9$ |
| 792 | " | " | " | $E^{10}$ |
| 793 | " | " | " | $E^{11}$ |
| 794 | " | " | " | $E^{12}$ |
| 795 | " | " | " | $E^{18}$ |
| 796 | " | " | " | $E^{16}$ |
| 797 | " | " | " | $E^{15}$ |
| 798 | " | " | " | $E^{38}$ |
| 799 | " | " | " | $E^{36}$ |
| 800 | 4-F, 3-Br | " | " | $E^7$ |
| 801 | " | " | " | $E^6$ |
| 802 | " | " | " | $E^5$ |
| 803 | " | " | " | $E^3$ |
| 804 | " | " | " | $E^9$ |
| 805 | " | " | " | $E^{10}$ |
| 806 | " | " | " | $E^{11}$ |
| 807 | " | " | " | $E^{12}$ |
| 808 | " | " | " | $E^{18}$ |
| 809 | " | " | " | $E^{16}$ |
| 810 | " | " | " | $E^{15}$ |
| 811 | " | " | " | $E^{38}$ |
| 812 | " | " | " | $E^{36}$ |
| 813 | 4-$OCH_2CH_3$ | " | " | $E^7$ |
| 814 | " | " | " | $E^6$ |
| 815 | " | " | " | $E^5$ |
| 816 | " | " | " | $E^3$ |
| 817 | " | " | " | $E^9$ |
| 818 | " | " | " | $E^{10}$ |
| 819 | " | " | " | $E^{11}$ |
| 820 | " | " | " | $E^{12}$ |
| 821 | 4-$OCH_2CH_3$ | " | " | $E^{18}$ |
| 822 | " | " | " | $E^{16}$ |
| 823 | " | " | " | $E^{15}$ |

TABLE 1-continued $$R^1-Ar^1-C(R)=N\sim O-CH_2-Ar^2$$

| No. | R¹ | Ar¹ | R | Ar² |
|---|---|---|---|---|
| 824 | 4-OCH₂CH₃ | " | " | E⁴⁴ |
| 825 | " | " | " | E³⁸ |
| 826 | " | " | " | E³⁶ |
| 827 | 3,4-O—CH₂—O | " | " | E⁷ |
| 828 | " | " | " | E⁶ |
| 829 | " | " | " | E⁵ |
| 830 | " | " | " | E³ |
| 831 | " | " | " | E⁹ |
| 832 | 3,4-OCH₂=O | " | " | E¹⁰ |
| 833 | " | " | " | E¹¹ |
| 834 | " | " | " | E¹² |
| 835 | " | " | " | E¹⁸ |
| 836 | " | " | " | E¹⁶ |
| 837 | " | " | " | E¹⁵ |
| 838 | " | " | " | E³⁸ |
| 839 | " | " | " | E³⁶ |
| 840 | 4-OCF₂H | " | " | E⁷ |
| 841 | " | " | " | E⁶ |
| 842 | " | " | " | E⁵ |
| 843 | " | " | " | E³ |
| 844 | " | " | " | E⁸ |
| 845 | " | " | " | E⁹ |
| 846 | " | " | " | E¹⁰ |
| 847 | " | " | " | E¹¹ |
| 848 | " | " | " | E¹² |
| 849 | " | " | " | E¹⁸ |
| 850 | " | " | " | E¹⁶ |
| 851 | " | " | " | E¹⁵ |
| 852 | " | " | " | E³⁸ |
| 853 | " | " | " | E³⁶ |
| 854 | 4-OCF₃ | " | " | E⁷ |
| 855 | " | " | " | E⁶ |
| 856 | " | " | " | E¹⁵ |
| 857 | " | " | " | E³ |
| 858 | " | " | " | E⁸ |
| 859 | " | " | " | E⁹ |
| 860 | " | " | " | E¹⁰ |
| 861 | " | " | " | E¹¹ |
| 862 | " | " | " | E¹² |
| 863 | " | " | " | E¹⁸ |
| 864 | " | " | " | E¹⁶ |
| 865 | " | " | " | E¹⁵ |
| 866 | " | " | " | E³⁸ |
| 867 | " | " | " | E³⁶ |
| 868 | 4-OCH₂CF₃ | " | " | E⁷ |
| 869 | " | " | " | E⁶ |
| 870 | " | " | " | E⁵ |
| 871 | " | " | " | E³ |
| 872 | " | " | " | E⁸ |
| 873 | " | " | " | E⁹ |
| 874 | " | " | " | E¹⁰ |
| 875 | " | " | " | E¹¹ |
| 876 | 4-OCH₂CF₃ | " | " | E¹⁸ |
| 877 | " | " | " | E¹⁶ |
| 878 | " | " | " | E¹⁵ |
| 879 | " | " | " | E³⁸ |
| 880 | " | " | " | E³⁶ |
| 881 | 4-CH₃ | " | " | E⁷ |
| 882 | " | " | " | E⁶ |
| 883 | " | " | " | E⁵ |
| 884 | " | " | " | E³ |
| 885 | " | " | " | E⁵⁶ |
| 886 | " | " | " | E⁹ |
| 887 | " | " | " | E¹⁰ |
| 888 | " | " | " | E¹¹ |
| 889 | " | " | " | E¹⁸ |
| 890 | " | " | " | E¹⁶ |
| 891 | " | " | " | E¹⁵ |
| 892 | " | " | " | E³⁸ |
| 893 | " | " | " | E³⁶ |
| 894 | 4-CH₂OCH₃ | " | " | E⁷ |
| 895 | " | " | " | E⁶ |
| 896 | " | " | " | E⁵ |

TABLE 1-continued $$R^1-Ar^1-\overset{\overset{R}{|}}{C}=N\sim O-CH_2-Ar^2$$

| No. | R¹ | Ar¹ | R | Ar² |
|---|---|---|---|---|
| 897 | " | " | " | E³ |
| 898 | 4-CH₂OCH₃ | " | " | E⁹ |
| 899 | " | " | " | E¹⁰ |
| 900 | " | " | " | E¹¹ |
| 901 | 4-CHOCH₃ | " | " | E¹⁸ |
| 902 | " | " | " | E¹⁶ |
| 903 | " | " | " | E¹⁵ |
| 904 | " | " | " | E³⁸ |
| 905 | " | " | " | E³⁶ |
| 906 | 4-(6-chloro-4-trifluoromethylpyridin-2-yloxy) | " | Et | E⁷ |
| 907 | " | " | " | E⁶ |
| 908 | " | " | " | E⁵ |
| 909 | " | " | " | E³ |
| 910 | " | " | " | E⁸ |
| 911 | " | " | " | E⁹ |
| 912 | " | " | " | E¹⁰ |
| 913 | " | " | " | E¹⁸ |
| 914 | " | " | " | E¹⁶ |
| 915 | " | " | " | E¹⁵ |
| 916 | " | " | " | E³⁶ |
| 917 | 4-F | " | cyclopropyl | E⁹ |
| 918 | 4-F | " | " | E¹⁰ |
| 919 | " | " | " | E¹¹ |
| 920 | " | " | " | E¹⁸ |
| 921 | " | " | " | E¹⁶ |
| 922 | " | " | " | E¹⁵ |
| 923 | " | " | " | E³⁶ |
| 924 | 4-Cl | " | " | E⁹ |
| 925 | " | " | " | E¹⁰ |
| 926 | " | " | " | E¹¹ |
| 927 | " | " | " | E¹⁸ |
| 928 | " | " | " | E¹⁶ |
| 929 | " | " | " | E¹⁵ |
| 930 | " | " | " | E³⁶ |
| 931 | 4-OMe | " | " | E⁹ |
| 932 | " | " | " | E¹⁰ |
| 933 | " | " | " | E¹¹ |
| 934 | " | " | " | E¹⁸ |
| 935 | " | " | " | E¹⁶ |
| 936 | " | " | " | E¹⁵ |
| 937 | " | " | " | E³⁶ |
| 938 | 4-CF₃ | " | CF₃ | E⁷ |
| 939 | " | " | " | E⁶ |
| 940 | 4-CF₃ | " | " | E⁵ |
| 941 | " | " | " | E³ |
| 942 | " | " | " | E⁹ |
| 943 | " | " | " | E¹⁰ |
| 944 | " | " | " | E¹¹ |
| 945 | " | " | " | E¹⁸ |
| 946 | " | " | " | E¹⁶ |
| 947 | " | " | " | E¹⁵ |
| 948 | " | " | " | E³⁶ |
| 949 | " | " | " | E³⁸ |
| 950 | 6-OCH₂CF₃ | 3-pyridyl | CF₃ | E⁵⁶ |
| 951 | " | " | " | E⁵⁷ |
| 952 | " | " | " | E⁵⁸ |
| 953 | " | " | " | E⁵⁹ |
| 954 | " | " | " | E⁶⁰ |
| 955 | 4-OCH₂CH₃ | phenyl | " | E⁵⁶ |
| 956 | " | " | " | E⁵⁷ |
| 957 | " | " | " | E⁵⁸ |
| 958 | " | " | " | E⁵⁹ |
| 959 | " | " | " | E⁶⁰ |
| 960 | 6-H | 2-pyridinyl | CF₂H | E⁹ |
| 961 | " | " | " | E¹⁰ |
| 962 | 6-H | 2-pyridinyl | CF₂H | E⁸ |
| 963 | " | " | " | E³⁶ |
| 964 | " | " | " | E³⁸ |
| 965 | 6-H | 3-pyridinyl | CF₂H | E⁸ |
| 966 | " | " | " | E⁹ |
| 967 | " | " | " | E¹⁰ |

TABLE 1-continued $$R^1-Ar^1-\overset{\overset{R}{|}}{C}=N\sim O-CH_2-Ar^2$$

| No. | $R^1$ | $Ar^1$ | R | $Ar^2$ |
|---|---|---|---|---|
| 968 | " | " | " | $E^{36}$ |
| 969 | " | " | " | $E^{38}$ |
| 970 | 6-Chlor | 3-pyridinyl | $CF_2H$ | $E^8$ |
| 971 | " | " | " | $E^9$ |
| 972 | " | " | " | $E^{10}$ |
| 973 | " | " | " | $E^{36}$ |
| 974 | " | " | " | $E^{38}$ |
| 975 | 6-$OCH_2CH_3$ | " | " | $E^8$ |
| 976 | " | " | " | $E^9$ |
| 977 | " | " | " | $E^{10}$ |
| 978 | " | " | " | $E^{36}$ |
| 979 | " | " | " | $E^{38}$ |
| 980 | 6-$OCH_2CF_3$ | 3-pyridinyl | $CF_2H$ | $E^8$ |
| 981 | " | " | " | $E^9$ |
| 982 | " | " | " | $E^{10}$ |
| 983 | " | " | " | $E^{36}$ |
| 984 | 6-$OCH_2CF_3$ | " | " | $E^{38}$ |
| 985 | 6-Cl | 3-pyridinyl | " | $E^3$ |
| 986 | 6-$OCH_2CF_3$ | " | " | $E^3$ |
| 987 | 6-Cl | 3-pyridinyl | $CF_3$ | $E^{72}$ |
| 988 | 6-$OCH_2CF_3$ | 3-pyridinyl | $CF_3$ | $E^{72}$ |
| 989 | " | " | " | $E^{62}$ |
| 990 | " | " | " | $E^{63}$ |
| 991 | " | " | " | $E^{64}$ |
| 992 | " | " | " | $E^{65}$ |
| 993 | " | " | " | $E^{67}$ |
| 994 | " | " | " | $E^{68}$ |
| 995 | " | " | " | $E^{69}$ |
| 996 | " | " | " | $E^{70}$ |
| 997 | " | " | " | $E^{71}$ |
| 998 | " | " | " | $E^{66}$ |
| 999 | " | " | " | $E^{73}$ |
| 1000 | 6-Cl | 3-pyridinyl | $CF_2CF_2H$ | $E^3$ |
| 1001 | " | " | " | $E^4$ |
| 1002 | " | " | " | $E^8$ |
| 1003 | " | " | " | $E^9$ |
| 1004 | " | " | " | $E^{10}$ |
| 1005 | " | " | " | $E^{11}$ |
| 1006 | 6-Cl | " | " | $E^{14}$ |
| 1007 | " | " | " | $E^{18}$ |
| 1008 | " | " | " | $E^{36}$ |
| 1009 | " | " | " | $E^{38}$ |
| 1010 | 6-Cl | 3-pyrimidinyl | $CF_2CF_2H$ | $E^{44}$ |
| 1011 | " | " | " | $E^{56}$ |
| 1012 | " | " | " | $E^{64}$ |
| 1013 | 6-$OCH_2CH_3$ | " | " | $E^3$ |
| 1014 | " | " | " | $E^4$ |
| 1015 | " | " | " | $E^8$ |
| 1016 | " | " | " | $E^9$ |
| 1017 | " | " | " | $E^{10}$ |
| 1018 | " | " | " | $E^{11}$ |
| 1019 | " | " | " | $E^{14}$ |
| 1020 | " | " | " | $E^{18}$ |
| 1021 | " | " | " | $E^{36}$ |
| 1022 | " | " | " | $E^{38}$ |
| 1023 | " | " | " | $E^{44}$ |
| 1024 | " | " | " | $E^{56}$ |
| 1025 | " | " | " | $E^{64}$ |
| 1026 | 6-$OCH_2CF_3$ | 3-pyridinyl | " | $E^6$ |
| 1027 | " | " | " | $E^7$ |
| 1028 | 6-$OCH_2CF_3$ | " | " | $E^7$ |
| 1029 | " | " | " | $E^9$ |
| 1030 | " | " | " | $E^{10}$ |
| 1031 | " | " | " | $E^{11}$ |
| 1032 | " | " | " | $E^{14}$ |
| 1033 | " | " | " | $E^{18}$ |
| 1034 | " | " | " | $E^{36}$ |
| 1035 | " | " | " | $E^{38}$ |
| 1036 | " | " | " | $E^{44}$ |
| 1037 | " | " | " | $E^{56}$ |
| 1038 | " | " | " | $E^{64}$ |
| 1039 | 6-Cl | 3-pyridinyl | $CF_2Cl$ | $E^6$ |
| 1040 | " | " | " | $E^7$ |

TABLE 1-continued $$R^1-Ar^1-\underset{\underset{R}{|}}{C}=N-O-CH_2-Ar^2$$

| No. | R¹ | Ar¹ | R | Ar² |
|---|---|---|---|---|
| 1041 | " | " | " | $E^8$ |
| 1042 | " | " | " | $E^9$ |
| 1043 | " | " | " | $E^{10}$ |
| 1044 | " | " | " | $E^{11}$ |
| 1045 | " | " | " | $E^{14}$ |
| 1046 | " | " | " | $E^{18}$ |
| 1047 | " | " | " | $E^{36}$ |
| 1048 | " | " | " | $E^{38}$ |
| 1049 | " | " | " | $E^{44}$ |
| 1050 | 6-Cl | 3-pyridinyl | $CF_2Cl$ | $E^{56}$ |
| 1051 | " | " | " | $E^{64}$ |
| 1052 | 6-$OCH_2CF_3$ | " | " | $E^6$ |
| 1053 | " | " | " | $E^7$ |
| 1054 | " | " | " | $E^8$ |
| 1055 | " | " | " | $E^9$ |
| 1056 | " | " | " | $E^{10}$ |
| 1057 | " | " | " | $E^{11}$ |
| 1058 | " | " | " | $E^{14}$ |
| 1059 | " | " | " | $E^{18}$ |
| 1060 | " | " | " | $E^{36}$ |
| 1061 | " | " | " | $E^{38}$ |
| 1062 | " | " | " | $E^{44}$ |
| 1063 | " | " | " | $E^{56}$ |
| 1064 | " | " | " | $E^{64}$ |
| 1065 | 6-$OCF_3$ | 3-pyridinyl | $CF_3$ | $E^6$ |
| 1066 | " | " | " | $E^7$ |
| 1067 | " | " | " | $E^8$ |
| 1068 | " | " | " | $E^9$ |
| 1069 | " | " | " | $E^{10}$ |
| 1070 | " | " | " | $E^{11}$ |
| 1071 | " | " | " | $E^{14}$ |
| 1072 | 6-$OCF_3$ | 3-pyridinyl | $CF_3$ | $E^{18}$ |
| 1073 | " | " | " | $E^{36}$ |
| 1074 | " | " | " | $E^{38}$ |
| 1075 | " | " | " | $E^{44}$ |
| 1076 | " | " | " | $E^{56}$ |
| 1077 | " | " | " | $E^{64}$ |
| 1078 | 6-$CF_3$ | " | " | $E^6$ |
| 1079 | " | " | " | $E^7$ |
| 1080 | " | " | " | $E^8$ |
| 1081 | " | " | " | $E^9$ |
| 1082 | " | " | " | $E^{10}$ |
| 1083 | " | " | " | $E^{11}$ |
| 1084 | " | " | " | $E^{14}$ |
| 1085 | " | " | " | $E^{18}$ |
| 1086 | " | " | " | $E^{36}$ |
| 1087 | " | " | " | $E^{38}$ |
| 1088 | " | " | " | $E^{44}$ |
| 1089 | " | " | " | $E^{56}$ |
| 1090 | " | " | " | $E^{64}$ |
| 1091 | 4-$OCH_2CH_3$ | phenyl | tBu | $E^9$ |
| 1092 | " | " | " | $E^{10}$ |
| 1093 | 4-OPh | phenyl | tBu | $E^9$ |
| 1094 | 4-OPh | phenyl | tBu | $E^{10}$ |
| 1095 | 3-Br, 4-F | " | $CF_3$ | $E^{44}$ |
| 1096 | 4-$OCH_3$ | " | cyclopropyl | $E^{44}$ |
| 1097 | 4-$OCH_2CH_3$ | " | " | $E^{44}$ |
| 1098 | " | " | $CF_3$ | $E^{66}$ |
| 1099 | " | " | " | $E^{73}$ |
| 1100 | " | " | " | $E^{67}$ |
| 1101 | " | " | " | $E^{62}$ |
| 1102 | " | " | " | $E^{63}$ |
| 1103 | " | " | " | $E^{64}$ |
| 1104 | " | " | " | $E^{65}$ |
| 1105 | " | " | " | $E^{27}$ |
| 1106 | 4-Br | " | cyclopropyl | $E^9$ |
| 1107 | " | " | " | $E^{10}$ |
| 1108 | " | " | " | $E^{11}$ |
| 1109 | " | " | " | $E^{14}$ |
| 1110 | " | phenyl | " | $E^{18}$ |
| 1111 | " | " | " | $E^{36}$ |
| 1112 | " | " | " | $E^{44}$ |
| 1113 | " | " | " | $E^{56}$ |

TABLE 1-continued $$R^1-Ar^1-\underset{\underset{R}{|}}{C}=N\sim O-CH_2-Ar^2$$

| No. | R¹ | Ar¹ | R | Ar² |
|---|---|---|---|---|
| 1114 | 3-Br, 4-F | " | " | E⁹ |
| 1115 | " | " | " | E¹⁰ |
| 1116 | 3-Br, 4-F | phenyl | cyclopropyl | E¹⁴ |
| 1117 | " | " | " | E¹⁸ |
| 1118 | " | " | " | E¹⁸ |
| 1119 | " | " | " | E⁴⁴ |
| 1120 | " | " | " | E⁵⁶ |
| 1121 | 3,4,5-trifluoro | " | " | E⁹ |
| 1122 | " | " | " | E¹⁰ |
| 1123 | " | " | " | E¹¹ |
| 1124 | " | " | " | E¹⁴ |
| 1125 | " | " | " | E¹⁸ |
| 1126 | " | " | " | E³⁶ |
| 1127 | " | " | " | E⁴⁴ |
| 1128 | " | " | " | E⁵⁶ |
| 1129 | 4-CF₃ | " | " | E⁹ |
| 1130 | " | " | " | E¹⁰ |
| 1131 | " | " | " | E¹¹ |
| 1132 | " | " | " | E¹⁴ |
| 1133 | " | " | " | E¹⁸ |
| 1134 | " | " | " | E³⁶ |
| 1135 | " | " | " | E⁴⁴ |
| 1136 | " | " | " | E⁵⁶ |
| 1137 | 4-OCH₂CH₃ | " | " | E⁹ |
| 1138 | 4-OCH₂CH₃ | phenyl | cyclopropyl | E¹⁰ |
| 1139 | " | " | " | E¹¹ |
| 1140 | " | " | " | E¹⁴ |
| 1141 | " | " | " | E¹⁸ |
| 1142 | " | " | " | E³⁶ |
| 1143 | " | " | " | E⁴⁴ |
| 1144 | " | " | " | E⁵⁶ |
| 1145 | 4-OCH₂CF₃ | " | " | E⁹ |
| 1146 | " | " | " | E¹⁰ |
| 1147 | " | " | " | E¹¹ |
| 1148 | " | " | " | E¹⁴ |
| 1149 | " | " | " | E¹⁸ |
| 1150 | " | " | " | E³⁶ |
| 1151 | " | " | " | E⁴⁴ |
| 1152 | " | " | " | E⁵⁶ |
| 1153 | 4-OCF₂H | " | " | E⁹ |
| 1154 | " | " | " | E¹⁰ |
| 1155 | " | " | " | E¹¹ |
| 1156 | " | " | " | E¹⁴ |
| 1157 | " | " | " | E¹⁸ |
| 1158 | " | " | " | E³⁶ |
| 1159 | " | " | " | E⁴⁴ |
| 1160 | 4-OCF₂H | phenyl | cyclopropyl | E⁵⁶ |
| 1161 | 4-OCF₃ | " | " | E⁹ |
| 1162 | " | " | " | E¹⁰ |
| 1163 | " | " | " | E¹¹ |
| 1164 | " | " | " | E¹⁴ |
| 1165 | " | " | " | E¹⁸ |
| 1166 | " | " | " | E³⁶ |
| 1167 | " | " | " | E⁴⁴ |
| 1168 | " | " | " | E⁵⁶ |
| 1169 | 4-OCF₂CF₂H | " | " | E⁹ |
| 1170 | " | " | " | E¹⁰ |
| 1171 | " | " | " | E¹¹ |
| 1172 | " | " | " | E¹⁴ |
| 1173 | " | " | " | E¹⁸ |
| 1174 | " | " | " | E³⁶ |
| 1175 | " | " | " | E⁴⁴ |
| 1176 | " | " | " | E⁵⁶ |
| 1177 | 4-Cl₃C | " | " | E⁹ |
| 1178 | " | " | " | E¹⁰ |
| 1179 | " | " | " | E¹¹ |
| 1180 | " | " | " | E¹⁴ |
| 1181 | " | " | " | E¹⁸ |
| 1182 | 4-Cl₃C | phenyl | cyclopropyl | E³⁶ |
| 1183 | " | " | " | E⁴⁴ |
| 1184 | " | " | " | E⁵⁶ |
| 1185 | 3,4-OCF₂O | " | " | E⁹ |
| 1186 | " | " | " | E¹⁰ |

TABLE 1-continued $$R^1-Ar^1-\underset{\underset{R}{|}}{C}=N\sim O-CH_2-Ar^2$$

| No. | R¹ | Ar¹ | R | Ar² |
|---|---|---|---|---|
| 1187 | " | " | " | $E^{11}$ |
| 1188 | " | " | " | $E^{14}$ |
| 1189 | " | " | " | $E^{18}$ |
| 1190 | " | " | " | $E^{36}$ |
| 1191 | " | " | " | $E^{44}$ |
| 1192 | " | " | " | $E^{56}$ |
| 1193 | 4-OCH(CH₃)O—CH₂CH₃ | " | " | $E^{9}$ |
| 1194 | " | " | " | $E^{10}$ |
| 1195 | " | " | " | $E^{11}$ |
| 1196 | " | " | " | $E^{14}$ |
| 1197 | " | " | " | $E^{18}$ |
| 1198 | " | " | " | $E^{36}$ |
| 1199 | " | " | " | $E^{44}$ |
| 1200 | " | " | " | $E^{56}$ |
| 1201 | 4-F | " | CF₃ | $E^{9}$ |
| 1202 | " | " | " | $E^{10}$ |
| 1203 | " | " | " | $E^{11}$ |
| 1204 | 4-F | phenyl | CF₃ | $E^{14}$ |
| 1205 | " | " | " | $E^{18}$ |
| 1206 | " | " | " | $E^{36}$ |
| 1207 | " | " | " | $E^{38}$ |
| 1208 | " | " | " | $E^{44}$ |
| 1209 | " | " | " | $E^{56}$ |
| 1210 | 3-OPh 4-F | " | " | $E^{9}$ |
| 1211 | " | " | " | $E^{10}$ |
| 1212 | " | " | " | $E^{11}$ |
| 1213 | " | " | " | $E^{14}$ |
| 1214 | " | " | " | $E^{18}$ |
| 1215 | " | " | " | $E^{36}$ |
| 1216 | " | " | " | $E^{38}$ |
| 1217 | " | " | " | $E^{44}$ |
| 1218 | " | " | " | $E^{56}$ |
| 1219 | 3-OPh | " | " | $E^{9}$ |
| 1220 | " | " | " | $E^{10}$ |
| 1221 | " | " | " | $E^{11}$ |
| 1222 | " | " | " | $E^{14}$ |
| 1223 | " | " | " | $E^{18}$ |
| 1224 | " | " | " | $E^{36}$ |
| 1225 | 3-OPh | phenyl | CF₃ | $E^{38}$ |
| 1226 | " | " | " | $E^{44}$ |
| 1227 | " | " | " | $E^{56}$ |
| 1228 | 3-CF₃ | " | " | $E^{9}$ |
| 1229 | " | " | " | $E^{10}$ |
| 1230 | " | " | " | $E^{11}$ |
| 1231 | " | " | " | $E^{14}$ |
| 1232 | " | " | " | $E^{18}$ |
| 1233 | " | " | " | $E^{36}$ |
| 1234 | " | " | " | $E^{38}$ |
| 1235 | " | " | " | $E^{44}$ |
| 1236 | " | " | " | $E^{56}$ |
| 1237 | 3,4-OCF₂O | " | " | $E^{9}$ |
| 1238 | " | " | " | $E^{10}$ |
| 1239 | " | " | " | $E^{11}$ |
| 1240 | " | " | " | $E^{14}$ |
| 1241 | " | " | " | $E^{18}$ |
| 1242 | " | " | " | $E^{36}$ |
| 1243 | " | " | " | $E^{38}$ |
| 1244 | " | " | " | $E^{44}$ |
| 1245 | " | " | " | $E^{56}$ |
| 1246 | 4-OCF₂CF₂H | " | " | $E^{9}$ |
| 1247 | 4-OCF₂CF₂H | phenyl | CF₃ | $E^{10}$ |
| 1248 | " | " | " | $E^{11}$ |
| 1249 | " | " | " | $E^{14}$ |
| 1250 | " | " | " | $E^{18}$ |
| 1251 | " | " | " | $E^{36}$ |
| 1252 | " | " | " | $E^{38}$ |
| 1253 | " | " | " | $E^{44}$ |
| 1254 | " | " | " | $E^{56}$ |
| 1255 | 2-Cl 4-OCF₂H | " | " | $E^{9}$ |
| 1256 | " | " | " | $E^{10}$ |
| 1257 | " | " | " | $E^{11}$ |

TABLE 1-continued $$R^1-Ar^1-\underset{\underset{R}{|}}{C}=N\sim O-CH_2-Ar^2$$

| No. | $R^1$ | $Ar^1$ | R | $Ar^2$ |
|---|---|---|---|---|
| 1258 | " | " | " | $E^{14}$ |
| 1259 | " | " | " | $E^{18}$ |
| 1260 | " | " | " | $E^{36}$ |
| 1261 | " | " | " | $E^{38}$ |
| 1262 | " | " | " | $E^{44}$ |
| 1263 | " | " | " | $E^{56}$ |
| 1264 | 4-OCH(CH$_3$)—OCH$_2$CH$_3$ | " | " | $E^9$ |
| 1265 | " | " | " | $E^{10}$ |
| 1266 | " | " | " | $E^{11}$ |
| 1267 | " | " | " | $E^{14}$ |
| 1268 | 4-OCH(CH$_3$)—OCH$_2$CH$_3$ | phenyl | CF$_3$ | $E^{18}$ |
| 1269 | " | " | " | $E^{36}$ |
| 1270 | " | " | " | $E^{38}$ |
| 1271 | " | " | " | $E^{44}$ |
| 1272 | " | " | " | $E^{56}$ |
| 1273 | 4-OCH$_2$CH$_2$Cl | " | " | $E^9$ |
| 1274 | " | " | " | $E^{10}$ |
| 1275 | " | " | " | $E^{11}$ |
| 1276 | " | " | " | $E^{14}$ |
| 1277 | " | " | " | $E^{18}$ |
| 1278 | " | " | " | $E^{36}$ |
| 1279 | " | " | " | $E^{38}$ |
| 1280 | " | " | " | $E^{44}$ |
| 1281 | " | " | " | $E^{56}$ |
| 1282 | 4-OCH$_2$CH$_2$—O—CH$_2$CH$_3$ | " | " | $E^9$ |
| 1283 | " | " | " | $E^{10}$ |
| 1284 | " | " | " | $E^{11}$ |
| 1285 | " | " | " | $E^{14}$ |
| 1286 | " | " | " | $E^{18}$ |
| 1287 | " | " | " | $E^{36}$ |
| 1288 | " | " | " | $E^{38}$ |
| 1289 | " | " | " | $E^{44}$ |
| 1290 | 4-O—CH$_2$—CH$_2$—O—CH$_2$CH$_3$ | phenyl | CF$_3$ | $E^{56}$ |
| 1291 | 4-CH$_2$OCH$_2$CH=CH$_2$ | " | " | $E^9$ |
| 1292 | " | " | " | $E^{10}$ |
| 1293 | " | " | " | $E^{11}$ |
| 1294 | " | " | " | $E^{14}$ |
| 1295 | " | " | " | $E^{18}$ |
| 1296 | " | " | " | $E^{36}$ |
| 1297 | " | " | " | $E^{38}$ |
| 1298 | " | " | " | $E^{44}$ |
| 1299 | " | " | " | $E^{56}$ |
| 1300 | 4-CCl$_3$ | " | " | $E^9$ |
| 1301 | " | " | " | $E^{10}$ |
| 1302 | " | " | " | $E^{11}$ |
| 1303 | " | " | " | $E^{14}$ |
| 1304 | " | " | " | $E^{18}$ |
| 1305 | " | " | " | $E^{36}$ |
| 1306 | " | " | " | $E^{38}$ |
| 1307 | " | " | " | $E^{44}$ |
| 1308 | " | " | " | $E^{56}$ |
| 1309 | 3,4,5-trifluoro | " | " | $E^9$ |
| 1310 | " | " | " | $E^{10}$ |
| 1311 | " | " | " | $E^{11}$ |
| 1312 | 3,4,5-trifluoro | phenyl | CF$_3$ | $E^{14}$ |
| 1313 | " | " | " | $E^{18}$ |
| 1314 | " | " | " | $E^{36}$ |
| 1315 | " | " | " | $E^{38}$ |
| 1316 | " | " | " | $E^{44}$ |
| 1317 | " | " | " | $E^{56}$ |
| 1318 | 4-OCH$_2$CH$_3$ | " | CH$_2$CH$_3$ | $E^9$ |
| 1319 | " | " | " | $E^{10}$ |
| 1320 | " | " | " | $E^{11}$ |
| 1321 | " | " | " | $E^{14}$ |
| 1322 | " | " | " | $E^{18}$ |
| 1323 | " | " | " | $E^{36}$ |
| 1324 | " | " | " | $E^{37}$ |
| 1325 | " | " | " | $E^{44}$ |
| 1326 | " | " | " | $E^{56}$ |
| 1327 | 4-Cl | " | CH$_2$=C(CH$_3$) | $E^9$ |
| 1328 | " | " | " | $E^{10}$ |
| 1329 | " | " | " | $E^{11}$ |
| 1330 | " | " | " | $E^{14}$ |

TABLE 1-continued $$R^1-Ar^1-\underset{\underset{R}{|}}{C}=N\sim O-CH_2-Ar^2$$

| No. | R¹ | Ar¹ | R | Ar² |
|---|---|---|---|---|
| 1331 | " | " | " | $E^{18}$ |
| 1332 | " | " | " | $E^{36}$ |
| 1333 | " | " | " | $E^{38}$ |
| 1334 | 4-Cl | phenyl | $CH_2=C(CH_3)$ | $E^{44}$ |
| 1335 | " | " | " | $E^{56}$ |
| 1336 | 4-$OCH_2CH_3$ | " | $H_2C=C(CH_3)$ | $E^9$ |
| 1337 | " | " | " | $E^{10}$ |
| 1338 | " | " | " | $E^{11}$ |
| 1339 | " | " | " | $E^{14}$ |
| 1340 | " | " | " | $E^{18}$ |
| 1341 | " | " | " | $E^{36}$ |
| 1342 | " | " | " | $E^{38}$ |
| 1343 | " | " | " | $E^{44}$ |
| 1344 | " | " | " | $E^{56}$ |
| 1345 | " | " | $(CH_3)_2C=CH$ | $E^9$ |
| 1346 | " | " | " | $E^{10}$ |
| 1347 | " | " | " | $E^{11}$ |
| 1348 | " | " | " | $E^{14}$ |
| 1349 | " | " | " | $E^{18}$ |
| 1350 | " | " | " | $E^{36}$ |
| 1351 | " | " | " | $E^{38}$ |
| 1352 | " | " | " | $E^{44}$ |
| 1353 | " | " | " | $E^{56}$ |
| 1354 | " | " | $CH_2=C(CF_3)$ | $E^9$ |
| 1355 | " | " | " | $E^{10}$ |
| 1356 | 4-$OCH_2CH_3$ | phenyl | $CH_2=C(CF_3)$ | $E^{11}$ |
| 1357 | " | " | " | $E^{14}$ |
| 1358 | " | " | " | $E^{18}$ |
| 1359 | " | " | " | $E^{36}$ |
| 1360 | " | " | " | $E^{38}$ |
| 1361 | " | " | " | $E^{44}$ |
| 1362 | " | " | " | $E^{56}$ |
| 1363 | " | " | $CH_2=C(F)$ | $E^9$ |
| 1364 | " | " | " | $E^{10}$ |
| 1365 | " | " | " | $E^{11}$ |
| 1366 | " | " | " | $E^{14}$ |
| 1367 | " | " | " | $E^{18}$ |
| 1368 | " | " | " | $E^{36}$ |
| 1369 | " | " | " | $E^{38}$ |
| 1370 | " | " | " | $E^{44}$ |
| 1371 | " | " | " | $E^{56}$ |
| 1372 | " | " | $CH_3CH=CH$ | $E^9$ |
| 1373 | " | " | " | $E^{10}$ |
| 1374 | " | " | " | $E^{11}$ |
| 1375 | " | " | " | $E^{14}$ |
| 1376 | " | " | " | $E^{18}$ |
| 1377 | " | " | " | $E^{36}$ |
| 1378 | 4-$OCH_2CH_3$ | phenyl | $CH_3CH=CH$ | $E^{38}$ |
| 1379 | " | " | " | $E^{44}$ |
| 1380 | " | " | " | $E^{56}$ |
| 1381 | " | " | $(CF_3)_2C=CH$ | $E^9$ |
| 1382 | " | " | " | $E^{10}$ |
| 1383 | " | " | " | $E^{11}$ |
| 1384 | " | " | " | $E^{14}$ |
| 1385 | " | " | " | $E^{18}$ |
| 1386 | " | " | " | $E^{36}$ |
| 1387 | " | " | " | $E^{38}$ |
| 1388 | " | " | " | $E^{44}$ |
| 1389 | " | " | " | $E^{56}$ |
| 1390 | 4-Cl | " | $(CF_3)_2CHCH_2$ | $E^9$ |
| 1391 | " | " | " | $E^{10}$ |
| 1392 | " | " | " | $E^{11}$ |
| 1393 | " | " | " | $E^{14}$ |
| 1394 | " | " | " | $E^{18}$ |
| 1395 | " | " | " | $E^{36}$ |
| 1396 | " | " | " | $E^{38}$ |
| 1397 | " | " | " | $E^{44}$ |
| 1398 | 4-$OCH_2CH_3$ | " | " | $E^9$ |
| 1399 | " | " | " | $E^{10}$ |
| 1400 | 4-$OCH_2CH_3$ | phenyl | $(CF_3)_2CH-CH_2$ | $E^{11}$ |
| 1401 | " | " | " | $E^{14}$ |
| 1402 | " | " | " | $E^{18}$ |
| 1403 | " | " | " | $E^{36}$ |

TABLE 1-continued $$R^1-Ar^1-\overset{\overset{R}{|}}{C}=N\sim O-CH_2-Ar^2$$

| No. | $R^1$ | $Ar^1$ | R | $Ar^2$ |
|---|---|---|---|---|
| 1404 | " | " | " | $E^{38}$ |
| 1405 | " | " | " | $E^{44}$ |
| 1406 | " | " | " | $E^{56}$ |
| 1407 | 4-Cl | " | " | $E^{56}$ |
| 1408 | 4-OCH$_2$CH$_3$ | " | CF$_3$CH$_2$CH$_2$ | $E^9$ |
| 1409 | " | " | " | $E^{10}$ |
| 1410 | " | " | " | $E^{11}$ |
| 1411 | " | " | " | $E^{14}$ |
| 1412 | " | " | " | $E^{18}$ |
| 1413 | " | " | " | $E^{36}$ |
| 1414 | " | " | " | $E^{38}$ |
| 1415 | " | " | " | $E^{44}$ |
| 1416 | " | " | " | $E^{56}$ |
| 1417 | " | " | CF$_2$Cl | $E^9$ |
| 1418 | " | " | " | $E^{10}$ |
| 1419 | " | " | " | $E^{11}$ |
| 1420 | " | " | CF$_2$Cl | $E^{14}$ |
| 1421 | " | " | " | $E^{18}$ |
| 1422 | 4-OCH$_2$CH$_3$ | phenyl | CF$_2$Cl | $E^{36}$ |
| 1423 | " | " | " | $E^{38}$ |
| 1424 | " | " | " | $E^{44}$ |
| 1425 | " | " | " | $E^{56}$ |
| 1426 | H | 2-thienyl | CF$_3$ | $E^1$ |
| 1427 | " | " | " | $E^9$ |
| 1428 | " | " | " | $E^{10}$ |
| 1429 | " | " | " | $E^{11}$ |
| 1430 | " | " | " | $E^{14}$ |
| 1431 | " | " | " | $E^{18}$ |
| 1432 | " | " | " | $E^{36}$ |
| 1433 | " | " | " | $E^{38}$ |
| 1434 | " | " | " | $E^{44}$ |
| 1435 | " | " | " | $E^{56}$ |
| 1436 | " | " | cyclopropyl | $E^8$ |
| 1437 | " | " | " | $E^9$ |
| 1438 | " | " | " | $E^{10}$ |
| 1439 | " | " | " | $E^{11}$ |
| 1440 | " | " | " | $E^{14}$ |
| 1441 | " | " | " | $E^{18}$ |
| 1442 | " | " | " | $E^{36}$ |
| 1443 | " | " | " | $E^{38}$ |
| 1444 | H | 2-thienyl | cyclopropyl | $E^{44}$ |
| 1445 | " | " | " | $E^{56}$ |
| 1446 | " | 2-naphthyl | CF$_3$ | $E^9$ |
| 1447 | " | " | " | $E^{10}$ |
| 1448 | " | " | " | $E^{11}$ |
| 1449 | " | " | " | $E^{14}$ |
| 1450 | " | " | " | $E^{18}$ |
| 1451 | " | " | " | $E^{36}$ |
| 1452 | " | " | " | $E^{38}$ |
| 1453 | " | " | " | $E^{44}$ |
| 1454 | " | " | " | $E^{56}$ |
| 1455 | 2-CH$_3$ | 5-benzofuranyl | " | $E^9$ |
| 1456 | " | " | " | $E^{10}$ |
| 1457 | " | " | " | $E^{11}$ |
| 1458 | " | " | " | $E^{14}$ |
| 1459 | " | " | " | $E^{18}$ |
| 1460 | " | " | " | $E^{36}$ |
| 1461 | " | " | " | $E^{38}$ |
| 1462 | " | " | " | $E^{44}$ |
| 1463 | " | " | " | $E^{56}$ |
| 1464 | 2-CF$_3$ | " | " | $E^9$ |
| 1465 | " | " | " | $E^9$ |
| 1466 | 2-CF$_3$ | 5-benzofuranyl | CF$_3$ | $E^{11}$ |
| 1467 | " | " | " | $E^{14}$ |
| 1468 | " | " | " | $E^{18}$ |
| 1469 | " | " | " | $E^{36}$ |
| 1470 | " | " | " | $E^{38}$ |
| 1471 | " | " | " | $E^{44}$ |
| 1472 | " | " | " | $E^{56}$ |
| 1473 | H | 2-benzothienyl | CF$_3$ | $E^9$ |
| 1474 | " | " | " | $E^{10}$ |
| 1475 | " | " | " | $E^{11}$ |
| 1476 | " | " | " | $E^{14}$ |

TABLE 1-continued $$R^1-Ar^1-\overset{R}{\underset{|}{C}}=N\sim O-CH_2-Ar^2$$

| No. | R¹ | Ar¹ | R | Ar² |
|---|---|---|---|---|
| 1477 | " | " | " | E¹⁸ |
| 1478 | " | " | " | E³⁶ |
| 1479 | " | " | " | E³⁸ |
| 1480 | " | " | " | E⁴⁴ |
| 1481 | " | " | " | E⁵⁶ |
| 1482 | 4-CF₃ | phenyl | CH₂=CH—CH₂—CF₂ | E⁹ |
| 1483 | " | " | " | E¹⁰ |
| 1484 | " | " | " | E¹¹ |
| 1485 | " | " | " | E¹⁴ |
| 1486 | " | " | " | E¹⁸ |
| 1487 | 4-CF₃ | phenyl | CH₂=CH—CH₂—CF₂ | E³⁶ |
| 1488 | " | " | " | E³⁸ |
| 1489 | " | " | " | E⁵⁶ |
| 1490 | 4-OCH₂C(Cl)=CH₂ | " | CF₃ | E⁹ |
| 1491 | " | " | " | E¹⁰ |
| 1492 | " | " | " | E⁸ |
| 1493 | " | " | " | E¹¹ |
| 1494 | " | " | " | E¹⁴ |
| 1495 | " | " | " | E¹⁸ |
| 1496 | " | " | " | E³⁶ |
| 1497 | " | " | " | E³⁸ |
| 1498 | " | " | " | E⁴⁴ |
| 1499 | " | " | " | E⁵⁶ |

Physical Data and NMR Signals

| Example Number | M.p. (°C.) | B.p. (°C.;GC) | ¹⁹F NMR (94.2 MHz, CDCl₃, CFCl₃) | |
|---|---|---|---|---|
| 2 | oil | — | syn: −131.3 (m, 1F) −66.6 (s, 3F) | |
| 6 | oil | — | syn: −131.8 (m, 1F) −66.3 (s, 3F) | |
| 27 | oil | 367 | syn: −131.7 (m, 1F) −74.1 (t, 3F) −66.3 (s, 3F) | |
| 32 | 103 | — | syn:anti = 96:4 | |
| | | | syn: −131.9 (m, 1F) −65.6 (s, 3F) | anti: −63.0 |
| 35 | oil | — | syn: −66.0 (s) | |
| 48 | oil | — | syn:anti = 85:15 | |
| | | | syn: −73.9 (t, 3F) −66.3 (s, 3F) | anti: −63.0 |
| 58 | oil | — | syn: −74.1 (t, 3F) −66.4 (s, 3F) | |
| 59 | oil | — | syn: −74.3 (t, 3F) −66.8 (s, 3F) | |
| 62 | oil | — | syn: −74.3 (t, 3F) −66.4 (s, 3F) | |
| 63 | oil | 373 | syn:anti = 57:43 | |
| | | | syn: −130.6 (m, 1F) −111.3 (m, 1F) −66.4 (s, 3F) | anti: −62.8 |
| 64 | oil | — | syn: −130.6 (m, 1F) −111.0 (m, 1F) −74.3 (t, 3F) −66.3 (s, 3F) | |
| 65 | oil | — | syn- −131.9 (m, 1F) −120.3 (m, 1F) −74.3 (t, 3F) −66.3 (s, 3F) | |
| 66 | oil | — | syn:anti = 70:30 | |
| | | | syn: −131.5 (m, 1F) −120.0 (m, 1F) −66.5 (s, 3F) | anti: −62.9 |
| 67 | oil | — | syn: −161.4 (m, 2F) −151.8 (m, 1F) −142.0 (m, 2F) −66.8 (s, 3F) | |
| 70 | oil | — | syn:anti = 91:9 | |
| | | | syn: −161.9 (m, 2F) −152.4 (m, 1F) −142.0 (m, 2F) −66.3 (s, 3F) | anti: −142.6 −62.8 |
| 72 | oil | — | syn:anti = 94:6 | |
| | | | syn: −161.9 (m, 2F) −152.5 (m, 1F) −142.3 (m, 2F) −66.3 (s, 3F) | anti: −163.0 −154.9 −142.8 −62.9 |
| 73 | oil | — | syn: −161.8 (m, 2F) −152.3 (m, 1F) −142.2 (m, 2F) −74.3 (t, 3F) −66.4 (s, 3F) | |
| 91 | oil | — | syn:anti = 63:37 | |
| | | | syn: −144.3 (m, 4F) −66.5 (s, 3F) | anti: −62.8 |
| 92 | oil | — | syn:anti = 66:34 | |
| | | | syn: −144.3 (m, 4F) −66.5 (s, 3F) | anti: −62.8 |

-continued

| Example Number | M.p. (°C.) | B.p. (°C.;GC) | ¹⁹F NMR (94.2 MHz, CDCl₃, CFCl₃) | |
|---|---|---|---|---|
| 92 | oil | — | syn:<br>−144.0 (m, 4F)<br>−66.4 (s, 3F) | |
| 96 | oil | — | syn:<br>−144.3 (m, 4F)<br>−66.4 (s, 3F) | |
| 97 | oil | — | syn:<br>−144.2 (m, 4F)<br>−66.3 (s, 3F) | |
| 99 | oil | 361 | syn:anti = 94:6 | |
| | | | syn:<br>−145.0 (m, 2F)<br>−143.8 (m, 2F)<br>−66.3 (s, 3F) | anti:<br><br><br>−62.8 |
| 104 | oil | 306 | syn:<br>−144.3 (m, 4F)<br>−74.0 (t, 3F)<br>−66.0 (s, 3F) | |
| 108 | 103 | — | syn:anti = 93:7 | |
| | | | syn:<br>−144.5 (m, 4F)<br>−65.8 (s, 3F) | anti:<br><br>−62.9 |
| 121 | oil | 328 | syn:<br>−158.0 (m, 2F)<br>−144.3 (m, 2F)<br>−66.5 (s, 3F) | |
| 125 | oil | | syn:<br>−158.5 (m, 2F)<br>−144.1 (m, 2F)<br>−66.5 (s, 3F) | |
| 127 | oil | — | syn:anti = 90:10 | |
| | | | syn:<br>−158.9 (m, 2F)<br>−144.3 (m, 2F)<br>−66.1 (s, 3F) | anti:<br><br><br>−62.8 |
| 130 | oil | — | syn:<br>−158.3 (m, 2F)<br>−144.4 (m, 2F)<br>−66.4 (s, 3F) | |
| 131 | oil | — | syn:anti = 93:7 | |
| | | | syn:<br>−158.0 (m, 2F)<br>−144.1 (m, 2F)<br>−66.5 (s, 3F) | anti:<br><br><br>−62.7 |
| 141 | oil | — | syn:anti = 61:39 | |
| | | | syn:<br>−142.8 (m, 2F)<br>−134.3 (m, 2F)<br>−66.6 (s, 3F) | anti:<br><br><br>−62.7 |
| 145 | oil | — | syn:<br>−142.8 (m, 2F)<br>−134.8 (m, 2F)<br>−66.3 (s, 3F) | |
| 148 | oil | — | syn:<br>−143.0 (m, 2F)<br>−134.5 (m, 2F)<br>−74.5 (m, 2F)<br>−66.5 (s, 3F) | |
| 153 | semi-solid | — | syn:<br>−138.8 (m, 2F)<br>−136.5 (m, 2F)<br>−74.3 (t, 3F)<br>−66.5 (s, 3F) | |
| 201 | semi-solid | — | syn:anti = 64:36 | |
| | | | syn:<br>−142.5 (m, 4F)<br>−66.5 (s, 3F) | anti:<br><br>−62.7 |
| 208 | oil | — | syn:<br>−142.3 (m, 4F)<br>−74.5 (t, 3F)<br>−66.4 (s, 3F) | |
| 244 | oil | — | syn:anti = 64:36 | |
| | | | syn:<br>−142.1 (m, 4F)<br>−66.6 (s, 3F) | anti:<br><br>−62.8 |
| 247 | oil | — | syn:<br>−142.3 (s, 3F) | |

-continued

| Example Number | M.p. (°C.) | B.p. (°C.;GC) | ¹⁹F NMR (94.2 MHz, CDCl₃, CFCl₃) | |
|---|---|---|---|---|
| | | | −74.3 (t, 6F)<br>−66.5 (s, 6F) | |
| 250 | oil | — | syn:<br>−109.3 (m, 2F)<br>−74.3 (t, 3F)<br>−66.5 (s, 3F) | |
| 252 | oil | — | syn:<br>−113.5 (m, 1F)<br>−108.8 (m, 1F)<br>−74.2 (t, 3F)<br>−66.3 (s, 3F) | |
| 254 | oil | — | syn:<br>−114.5 (m, 2F)<br>−74.1 (t, 3F)<br>−66.3 (s, 3F) | |
| 258 | oil | — | syn:<br>−113.3 (m, 1F)<br>−74.3 (t, 3F)<br>−66.3 (s, 3F) | |
| 261 | oil | — | syn:<br>−137.8 (m, 2F)<br>−74.1 (t, 3F)<br>−66.5 (s, 3F) | |
| 264 | oil | — | syn:<br>−142.9 (m, 1F)<br>−138.2 (m, 1F)<br>−74.3 (t, 3F)<br>−66.4 (s, 3F) | |
| 267 | oil | — | syn:<br>−124.1 (m, 1F)<br>−118.8 (m, 1F)<br>−74.3 (t, 3F)<br>−66.4 (s, 3F) | |
| 270 | oil | — | syn:<br>−113.4 (m, 2F)<br>−105.8 (m, 1F)<br>−74.3 (t, 3F)<br>−66.4 (s, 3F) | |
| 274 | oil | — | syn:anti = 59:41 | |
| | | | syn:<br>−137.3 (m, 2F)<br>−88.6 (m, 2F)<br>−66.5 (s, 3F) | anti:<br><br><br>−63.0 |
| 275 | oil | — | syn:<br>−137.3 (m, 2F)<br>−87.8 (m, 2F)<br>−66.3 (s, 3F) | |
| 276 | oil | — | syn:<br>−137.1 (m, 2F)<br>−88.5 (m, 2F)<br>−74.4 (t, 3F)<br>−66.5 (s, 3F) | |
| 285 | oil | — | syn:<br>−74.3 (t, 3F)<br>−66.3 (s, 3F) | |
| 288 | oil | — | syn:<br>−74.1 (t, 3F)<br>−66.3 (s, 3F) | |
| 361 | oil | — | syn:<br>−131.6 (m, 1F)<br>−65.6 (s, 3F) | |
| 363 | oil | — | syn:<br>−144.4 (m, 4F)<br>−65.6 (s, 3F) | |
| 378 | oil | — | syn:<br>−131.5 (m, 1F)<br>−65.5 (s, 3F) | |
| 380 | 108–110 | — | syn:<br>−144.3 (m, 4F)<br>−65.5 (s, 3F) | |
| 384 | oil | — | syn:<br>−131.6 (m, 1F)<br>−65.6 (s, 3F) | |
| 386 | oil | — | syn:anti = 84:16 | |
| | | | syn:<br>−144.2 (m, 4F)<br>−65.8 (s, 3F) | anti:<br><br>−60.5 |

-continued

| Example Number | M.p. (°C.) | B.p. (°C.;GC) | ¹⁹F NMR (94.2 MHz, CDCl₃, CFCl₃) |
|---|---|---|---|
| 397 | 72 | — | syn: <br> −162.5 (m, 2F) <br> −154.0 (m, 1F) <br> −142.5 (m, 2F) <br> −74.3 (t, 3F) |
| 398 | 71 | — | syn: <br> −144.7 (m, 4F) <br> −74.3 (t, 3F) |
| 402 | oil | — | syn: <br> −131.6 (m, 1F) <br> −74.0 (t, 3F) |
| 403 | oil | — | syn: <br> −74.3 (t) |
| 404 | oil | — | syn: <br> −74.2 (t) |
| 405 | oil | — | syn: <br> −162.8 (m, 2F) <br> −154.1 (m, 1F) <br> −146.3 (m, 2F) <br> −74.3 (t, 3F) |
| 406 | oil | — | syn: <br> −145.0 (m, 4F) <br> −74.0 (t, 3F) |
| 407 | oil | — | syn: <br> −157.4 (m, 2F) <br> −143.6 (m, 2F) <br> −74.3 (t, 3F) <br> −66.5 (s, 3F) |
| 429 | oil | — | syn: <br> −162.9 (m, 2F) <br> −154.3 (m, 1F) <br> −142.5 (m, 2F) |
| 430 | oil | — | syn: <br> −144.9 (m) |
| 432 | oil | — | syn: <br> −143.0 (m, 2F) <br> −135.4 (m, 2F) |
| 454 | oil | — | syn: <br> −74.3 (t, 3F) <br> −66.4 (s, 3F) |
| 458 | oil | — | syn: <br> −74.1 (t, 3F) <br> −66.3 (s, 3F) |
| 460 | oil | — | syn: <br> −74.4 (t, 3F) <br> −66.5 (s, 3F) |
| 462 | oil | — | syn: <br> −66.5 (s, 3F) <br> −60.0 (s, 3F) |
| 464 | oil | — | syn: <br> −66.0 (s, 3F) <br> −60.3 (s, 3F) |
| 465 | oil | — | syn: <br> −74.3 (t, 3F) <br> −66.5 (s, 3F) <br> −60.3 (s, 3F) |
| syn:anti 466 | 57:43- oil | — | syn:anti = 57:43 <br> syn: anti: <br> −66.6 (s, 3F) <br> −63.5 (s, 3F) −63.5 |
| 468 | oil | — | syn: <br> −66.3 (s, 3F) <br> −63.3 (s, 3F) |
| 469 | oil | — | syn: <br> −74.2 (t, 3F) <br> −66.5 (s, 3F) <br> −63.2 (s, 3F) |
| 470 | oil | — | syn: <br> −66.5 (s, 3F) <br> −63.1 (s, 3F) |
| 471 | oil | — | syn: <br> −65.8 (s, 3F) <br> −63.1 (s, 3F) |
| 472 | oil | — | syn: <br> −66.5 (s, 3F) <br> −63.0 (s, 3F) |
| 473 | oil | 301 | syn: <br> −74.3 (s, 3F) <br> −66.4 (s, 3F) <br> −63.0 (s, 3F) |
| 474 | 98 | — | syn: <br> −74.3 (t, 3F) <br> −66.4 (s, 3F) |
| 475 | oil | — | syn:anti = 87:13 <br> syn: anti: <br> −66.0 (s) −62.9 |
| 477 | oil | — | syn: <br> −66.3 (s) |
| 478 | oil | — | syn: <br> −74.2 (t, 3F) <br> −66.3 (s, 3F) |
| 480 | oil | — | syn: <br> −73.9 (t, 3F) <br> −66.4 (s, 3F) |
| 481 | oil | — | syn: <br> −74.1 (t, 3F) <br> −66.3 (s, 3F) |
| 485 | oil | — | syn: <br> −74.3 (t, 3F) <br> −66.5 (s, 3F) <br> −58.3 (s, 3F) |
| 489 | oil | — | syn: <br> −74.3 (t, 3F) <br> −66.4 (s, 3F) <br> −58.1 (s, 3F) |
| 493 | oil | — | syn: <br> −74.5 (t, 3F) <br> −66.5 (s, 3F) |
| 496 | oil | — | syn: <br> −66.0 (s, 3F) |
| 497 | oil | — | syn: <br> −74.3 (t, 3F) <br> −66.3 (s, 3F) |
| 502 | oil | — | syn: <br> −66.5 (s, 3F) |
| 506 | oil | — | syn: <br> −66.0 (s, 3F) |
| 507 | 51 | 368 | syn: <br> −74.3 (t, 3F) <br> −66.3 (s, 3F) |
| 513 | oil | — | syn: <br> −66.3 (s, 3F) |
| 514 | 68 | — | syn: <br> −74.3 (t, 3F) <br> −66.3 (s, 3F) |
| 517 | oil | — | syn: <br> −66.5 (s, 3F) |
| 518 | 104 | — | syn: <br> −74.5 (t, 3F) <br> −66.5 (s, 3F) |
| 764 | oil | — | syn: <br> −144.3 (m, 4F) <br> −66.8 (s, 3F) |
| 765 | oil | — | syn: <br> −158.6 (m, 2F) <br> −144.3 (m, 2F) <br> −66.6 (s, 3F) |
| 766 | oil | — | syn: <br> −143.0 (m, 2F) <br> −134.5 (m, 2F) <br> −67.0 (s, 3F) |
| 778 | oil | — | syn: <br> −144.3 (m, 4F) <br> −66.8 (s, 3F) |
| 779 | 56 | — | syn: <br> −158.5 (m, 2F) <br> −144.3 (m, 2F) <br> −66.5 (s, 3F) |
| 785 | oil | — | syn: <br> −66.4 (s, 3F) |
| 791 | 53 | — | syn: <br> −74.4 (m, 4F) <br> −66.8 (s, 3F) |

-continued

| Example Number | M.p. (°C.) | B.p. (°C.;GC) | 19F NMR (94.2 MHz, CDCl3, CFCl3) | |
|---|---|---|---|---|
| 804 | oil | — | syn:anti = 90:10 | |
| | | | syn: | anti: |
| | | | −144.5 (m, 4F) | |
| | | | −103.0 (m, 1F) | |
| | | | −66.1 (s, 3F) | −62.5 |
| 805 | oil | — | syn: | |
| | | | −158.3 (m, 2F) | |
| | | | −142.5 (m, 2F) | |
| | | | −103.0 (m, 1F) | |
| | | | −66.5 (s, 3F) | |
| 817 | oil | 328 | syn: | |
| | | | −143.4 (m, 4F) | |
| | | | −66.5 (s, 3F) | |
| 818 | oil | 335 | syn: | |
| | | | −158.5 (m, 2F) | |
| | | | −144.3 (m, 2F) | |
| | | | −66.3 (s, 3F) | |
| syn-819 | oil | — | syn: | |
| | | | −142.9 (m, 2F) | |
| | | | −137.8 (m, 2F) | |
| | | | −66.4 (s, 3F) | |
| syn:anti = 87:13-819 | oil | — | syn:anti = 87:13 | |
| | | | syn: | anti: |
| | | | −142.9 (m, 2F) | |
| | | | −137.8 (m, 2F) | |
| | | | −66.4 (s, 3F) | −62.5 |
| 824 | oil | — | syn: | |
| | | | −66.2 (s, 3F) | |
| | | | −62.9 (s, 3F) | |
| 825 | oil | — | syn: | |
| | | | −65.8 (s, 3F) | |
| 826 | oil | — | syn: | |
| | | | −66.5 (s, 3F) | |
| | | | −56.0 (s, 3F) | |
| 831 | oil | — | syn:anti = 59:41 | |
| | | | syn: | anti: |
| | | | −144.4 (m, 4F) | |
| | | | −66.3 (s, 3F) | −62.5 |
| 832 | oil | — | syn:anti = 59:41 | |
| | | | syn: | anti: |
| | | | −158.5 (m, 2F) | |
| | | | −144.4 (m, 2F) | |
| | | | −66.4 (s, 3F) | −62.3 |
| 838 | oil | — | syn:anti = 66:34 | |
| | | | syn: | anti: |
| | | | −66.4 (s, 3F) | −62.0 |
| 845 | oil | — | syn:anti = 89:11 | |
| | | | syn: | anti: |
| | | | −144.5 (m, 4F) | |
| | | | −81.6 (md, 2F) | |
| | | | −66.5 (s, 3F) | −62.5 |
| 846 | oil | — | syn: | |
| | | | −158.5 (m, 2F) | |
| | | | −144.3 (m, 2F) | |
| | | | −81.8 (md, 2F) | |
| | | | −66.5 (s, 3F) | |
| 852 | oil | — | syn: | |
| | | | −81.9 (md, 2F) | |
| | | | −66.5 (s, 3F) | |
| 859 | oil | — | syn: | |
| | | | −144.3 (m, 4F) | |
| | | | −66.6 (s, 3F) | |
| | | | −58.3 (s, 3F) | |
| 860 | oil | 295 | syn: | |
| | | | −158.5 (m, 2F) | |
| | | | −144.4 (m, 2F) | |
| | | | −66.9 (s, 3F) | |
| | | | −58.5 (s, 3F) | |
| 866 | oil | — | syn: | |
| | | | −66.4 (s, 3F) | |
| | | | −58.0 (s, 3F) | |
| 872 | oil | — | syn: | |
| | | | −161.9 (m, 2F) | |
| | | | −152.1 (m, 1F) | |
| | | | −142.0 (m, 2F) | |

-continued

| Example Number | M.p. (°C.) | B.p. (°C.;GC) | 19F NMR (94.2 MHz, CDCl3, CFCl3) | |
|---|---|---|---|---|
| | | | −74.3 (t, 3F) | |
| | | | −66.5 (s, 3F) | |
| 873 | oil | — | syn: | |
| | | | −144.4 (m, 4F) | |
| | | | −74.3 (t, 3F) | |
| | | | −66.4 (s, 3F) | |
| 874 | oil | — | syn: | |
| | | | −74.3 (t, 3F) | |
| | | | −66.8 (s, 3F) | |
| 879 | oil | — | syn: | |
| | | | −74.3 (t, 3F) | |
| | | | −66.5 (s, 3F) | |
| 886 | oil | — | syn: | |
| | | | −144.4 (m, 4F) | |
| | | | −66.5 (s, 3F) | |
| 892 | oil | — | syn: | |
| | | | −66.5 (s, 3F) | |
| 898 | oil | — | syn:anti = 80:20 | |
| | | | syn: | anti: |
| | | | −144.5 (m, 4F) | |
| | | | −66.6 (s, 3F) | −62.8 |
| 911 | oil | — | syn: | |
| | | | −145.0 (m, 4F) | |
| | | | −62.0 (s, 3F) | |
| anti-917 | oil | — | anti: | |
| | | | −144.8 (m, 4F) | |
| | | | −113.0 (m, 1F) | |
| syn:anti-917 | oil | — | syn:anti = 50:50 | |
| | | | syn: | anti: |
| | | | −144.8 (m, 4F) | |
| | | | −112.3 (m, 1F) | −113.0 |
| syn:anti = 12:88-918 | 63 | | syn:anti = 12:88 (1H) | |
| | | | −159.0 (m, 2F) | |
| | | | −144.5 (m, 2F) | |
| | | | −113.0 (m, 1F) | |
| 924 | oil | — | syn: | |
| | | | −144.6 (m, 4F) | |
| 932 | oil | — | syn: | |
| | | | −144.7 (m, 4F) | |
| 938 | oil | — | syn: | |
| | | | −132.3 (m, 1F) | |
| | | | −120.0 (m, 1F) | |
| | | | −66.6 (s, 3F) | |
| | | | −63.5 (s, 3F) | |
| 939 | oil | — | syn: | |
| | | | −130.8 (m, 1F) | |
| | | | −111.5 (m, 1F) | |
| | | | −66.8 (s, 3F) | |
| | | | −63.8 (s, 3F) | |
| 942 | oil | — | syn: | |
| | | | −144.3 (m, 4F) | |
| | | | −67.0 (s, 3F) | |
| | | | −63.8 (s, 3F) | |
| 943 | oil | — | syn: | |
| | | | −158.5 (m, 2F) | |
| | | | −144.3 (m, 2F) | |
| | | | −66.9 (s, 3F) | |
| | | | −63.8 (s, 3F) | |
| 944 | oil | — | syn: | |
| | | | −143.0 (m, 2F) | |
| | | | −134.5 (m, 2F) | |
| | | | −66.8 (s, 3F) | |
| | | | −63.8 (s, 3F) | |
| 945 | oil | — | syn: | |
| | | | −144.2 (m, 4F) | |
| | | | −65.9 (s, 3F) | |
| 949 | oil | — | syn: | |
| | | | −66.5 (s, 3F) | |
| | | | −63.5 (s, 3F) | |
| 950 | oil | — | syn: | |
| | | | −74.3 (t, 3F) | |
| | | | −66.7 (s, 3F) | |
| | | | −63.3 (s, 3F) | |
| 954 | oil | — | syn: | |

| Example Number | M.p. (°C.) | B.p. (°C.;GC) | ¹⁹F NMR (94.2 MHz, CDCl₃, CFCl₃) | |
|---|---|---|---|---|
| 955 | oil | — | −66.1 (s, 3F) syn: −66.4 (s, 3F) | |
| 958 | oil | — | −63.5 (s, 3F) syn: −65.7 (s, 3F) | |
| 959 | 66 | — | syn: −66.0 (s, 3F) | |
| syn-987 | oil | — | syn: −66.5 (s, 3F) | |
| syn:anti = 88:12-987 | oil | — | syn:anti = 88:12 syn: −66.5 | anti: −63.0 |
| 988 | oil | — | syn: −74.4 (t, 3F) −66.3 (s, 3F) | |
| 989 | oil | — | syn: −142.3 (m, 1F) −137.3 (m, 1F) −119.5 (m, 3F) −74.3 (t, 3F) −66.5 (s, 3F) | |
| 993 | oil | — | syn: −74.2 (t, 3F) −66.3 (s, 3F) | |
| 994 | 93 | — | syn: −74.0 (t, 3F) −66.1 (s, 3F) | |
| 995 | oil | — | syn: −74.0 (t, 3F) −66.4 (s, 3F) | |
| 996 | oil | — | syn: −74.0 (t, 3F) −66.6 (s, 3F) | |
| 997 | oil | — | syn: −74.3 (t, 3F) −66.4 (s, 3F) | |
| 998 | oil | — | syn: −74.3 (m, 6F) −66.3 (s, 3F) | |
| 1028 | oil | — | syn:anti = 75:25 syn: −161.6 (m, 2F) −151.8 (m, 1F) −138.1 (m, 2F) −114.0 (m, 2F) −74.3 (t, 3F) | anti: −137.0 −115.5 |
| 1029 | oil | — | syn:anti = 75:25 syn: −144.5 (m, 4F) −138.5 (m, 2F) −114.1 (m, 2F) −73.3 (t, 3F) | anti: −137.0 −115.8 |
| 1030 | oil | — | syn:anti = 70:30 syn: −158.0 (m, 2F) −143.3 (m, 2F) −138.5 (m, 2F) −114.0 (m, 2F) −74.3 (t, 3F) | anti: −137.0 −115.8 |
| 1036 | oil | — | syn:anti = 54:46 syn: −138.0 (m, 2F) −113.9 (m, 2F) −74.3 (t, 3F) −63.3 (s, 3F) | anti: −137.0 −116.0 |
| 1093 | oil | — | syn: −144.1 (m, 4F) | |
| 1094 | oil | — | syn:anti = 75:25 (¹H) −158.3 (m, 2F) −144.5 (m, 2F) | |
| 1095 | oil | — | syn: −103.0 (m, 1F) −66.8 (s, 3F) | |
| 1096 | oil | — | −63.0 (s, 3F) syn:anti = 80:20 (¹H) −63.0 (s, 3F) | |
| 1098 | 86–88 | — | syn: −66.0 (s, 3F) | |
| 1099 | oil | — | syn: −66.4 (s, 3F) | |
| 1100 | oil | — | syn: −66.0 (s, 3F) | |
| 1101 | oil | — | syn: −142.6 (m, 1F) −137.3 (m, 1F) −119.3 (m, 3F) −66.3 (s, 3F) | |
| 1105 | oil | — | syn: −111.5 (m, 2F) −106.3 (m, 1F) −66.2 (s, 3F) | |
| syn:anti = 14:86-1137 | oil | — | syn:anti = 14:86 (¹H) −144.7 (m, 4F) | |
| syn:anti = 49:51-1137 | oil | — | syn:anti = 49:51 (¹H) −145.0 (m, 4F) | |
| 1201 | oil | — | syn: −144.3 (m, 4F) −112.9 (m, 1F) −66.5 (s, 3F) | |
| 1207 | oil | — | syn: −113.0 (m, 1F) −66.3 (s, 3F) | |
| 1210 | oil | — | syn: −144.4 (m, 4F) −127.5 (m, 1F) −66.6 (s, 3F) | |
| 1216 | oil | — | syn: −127.3 (m, 1F) −66.5 (s, 3F) | |
| 1219 | oil | — | syn:anti = 92:8 syn: −144.4 (m, 4F) −66.2 (s, 3F) | anti: −62.5 |
| 1228 | oil | — | syn: −144.3 (m, 4F) −66.8 (s, 3F) −63.5 (s, 3F) | |
| 1234 | oil | — | syn: −66.4 (s, 3F) −63.3 (s, 3F) | |
| 1291 | oil | — | syn: −145.3 (m, 4F) −65.3 (s, 3F) | |
| 1318 | oil | — | syn:anti = 33:67 (¹H) −145.5 (m, 4F) | |
| 1324 | oil | — | syn:anti = 35:65 (¹H) −144.3 (m, 4F) | |
| 1390 | 75–80 | — | — | |
| 1396 | 121–123 | — | — | |
| 1426 | oil | — | syn: −131.8 (m, 1F) −65.1 (s, 3F) | |
| 1427 | oil | — | syn: −65.3 (s, 3F) | |
| 1433 | oil | — | syn: −65.3 (s, 3F) | |
| 1437 | oil | — | −145.0 (s, 4F) | |
| 1438 | oil | — | −158.8 (m, 2F) −144.3 (m, 2F) | |

BIOLOGICAL EXAMPLES

Example 1

1 ml portions of the test formulation, emulsified in water, are applied uniformly to the internal side of lid and bottom of a Petri dish and, when the coating has dried, batches of 10 imagines of the common house fly (*Musca domestica*) are introduced. The dishes are sealed and stored at room temperature, and the mortality of the test animals is determined after 3 hours. A good activity (100% mortality) against the common house fly is shown, at a concentration of 250 ppm (based on active substance content), of the preparations 6, 27, 32, 35, 48, 58, 62 to 67, 72, 73, 91, syn-92, (syn:anti=63:37)-92, 96, 97, 104, 108, 127, 141, 145, 148, 153, 169, 208, 244, 250, 252, 254, 258, 261, 264, 267, 275, 276, 285, 288, 361, 397, 398, 402 to 407, 429, 430, 432, 454, 458, 464, 465, 466, 468, 469, 470, 471, 472, 473, 474, 477, 480, 481, 485, 493, 496, 497, 506, 507, 513, 517, 764 to 766, 804, 805, 817, 818, syn-819, 824, 831, 832, 838, 845, 852, 859, 860, 866, 872, 873, 874, 879, 892, 898, 911, 924, 932, 938, 939, 942, 943, 944, 949, 958, 959, 987, 988, 989, 993, 994, 995, 996, 997, 998, 1029, 1030, 1094, 1098, 1099, 1101, 1105, (syn:anti=14:86)-1137, (syn:anti=49:51)-1137, 1318, 1426, 1427, 1433, 1437 and 1438.

Example 2

Rice seed is germinated on moist cotton wool in glass containers and, after the stem length had reached a length of approximately 8 cm, the plants were immersed in the test solution with the leaves. The test solution was allowed to run off, and the rice plants which had been treated in this manner were separated according to the test concentration, transferred into glass containers and infested with batches of 10 larvae (L3) of the species *Nilaparvata lugens*. The glass containers were sealed and kept for 4 days at 21° C., whereupon the mortality of the cicada larvae can be determined.

Under these experimental conditions, an activity of 100% was shown by the compounds 27, 48, 58, 64, 65, syn-92, 96, 97, 104, 125, 127, 145, 148, 208, 402, 403, 406, 407, 478, 507, 791, 804, 817, 818, syn-819, (syn:anti=87:13)-819, 825, 826, 831, 832, 845, 852, 859, 860, 866, 873, 874, 879, 892, (syn:anti=50:50)-917, 924, 932, 938, 942, 949, 959, 987, 996, 1029, 1101, 1105, (syn:anti=14:86)-1137 and 1201 at a test concentration of 250 ppm of a.i.

Example 3

Wheat seed is pregerminated for 6 hours under water, then transferred into 10 ml glass test tubes and covered with 2 ml portions of soil. 1 ml of water is added, and the plants remain in the glass containers at room temperature (21° C.) until they have reached a height of approximately 3 cm. *Diabrotica undecempunctata* larvae in the medium stages (in each case 10 specimens) are subsequently introduced into the glass containers by being placed on the soil and, after 2 hours, 1 ml of the test concentration of test liquid is pipetted onto the soil surface in the glass containers. After the containers have been left for 5 days under laboratory conditions (21° C.), the soil and the roots are examined for live *Diabrotica larvae* and the mortality is determined. It emerged that, under the abovementioned test conditions, an activity of 100% was shown by the compounds 2, 27, 48, 58, 59, 63 to 65, 67, 72, 73, syn-92, (syn:anti=63:27)-92, 96, 97, 104, 121, 125, 127, 148, 169, 208, 250, 254, 258, 261, 267, 274, 363, 380, 402 to 407, 429, 430, 469, 474, 481, 817, 831, 845, 852, 859, 860, 866, 873, 924, 942, 943, 987, 1101, (syn:anti=14:86)-1137 and (syn:anti=49:51)-1137 at a test concentration of 250 ppm of a.i.

Example 4

Field beans (*Vicia faba*) which are heavily populated with the black bean aphid (*Aphis fabae*) are sprayed with aqueous dilutions of concentrates of wettable powders with an active substance content of 250 ppm to run off point. The mortality of the aphids is determined after 3 days. A 100% mortality can be obtained using the compounds of Examples 27, 48, 58, 96, 97, 148, 402 to 404, 406, 407, 470, 506, 791, 817, 818, syn-819, 825, 826, 838, 852, 859, 860, 866, 873, 874, 879, 898, 924, 938, 939, 942, 944, 949, 987, 1101, (syn:anti=14:86)-1137 and (syn:anti=49:50)-1137.

Example 5

Bean plants (*Phaseolus v.*) which are heavily populated with greenhouse red spider mites (*Tetranychus urticae*, full population) were sprayed with the aqueous dilution of a concentrate of wettable powder which contained 250 ppm of the active substance in question. The mortality of the mites was checked after 7 days. A 100% mortality was obtained using the compounds of Examples 35, 58, 402 to 404, 454, 506, 818, 866, 879 and 949.

Example 6

Filter paper disks on which eggs of cotton bugs (*Oncopeltus fasciatus*) have been placed are treated with 0.5 ml portions of aqueous dilution of the test formulation. When the coating has dried on, the Petri dish is sealed and the inside is kept at maximum atmospheric humidity. The dishes are stored at room temperature and, after 7 days, the ovicidal and larvicidal activities are determined. A 100% mortality was obtained by the compounds of Examples 27, 58, 64, 67, 70, 73, 92, 96, 127, 145, 148, 208, 250, 402 to 407, 429, 496, 497 and 817 at an active substance content of 500 ppm.

We claim:

1. A compound of the formula I in the form of the syn or the anti compound or a mixture of these or a salt thereof,

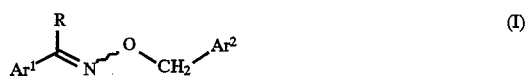

in which

R is $CF_3$;

$Ar^1$ is phenyl, naphthyl, indanyl, benzofuryl, benzothienyl

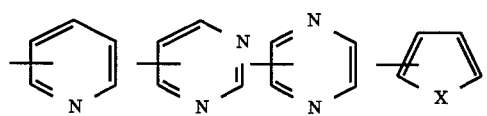

or

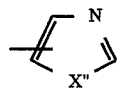

and has optionally up to 5 identical or different substituents $R^1$ selected from the group consisting of
1) $(C_1-C_6)$-alkyl,
2) $(C_2-C_6)$-alkenyl,
3) $(C_2-C_6)$-alkynyl 4) $(C_3-C_8)$-cycloalkyl which is optionally substituted by up to 6 identical or different radicals selected from the group consisting of halogen and $(C_1-C_4)$-alkyl,
5) halogen,
6) $(C_1-C_6)$-haloalkyl,
7) $(C_2-C_6)$-haloalkenyl,
8) $(C_2-C_6)$-haloalkynyl,
9) $(C_1-C_6)$-alkoxy-$(C_1-C_6)$-alkyl,
10) $(C_6-C_{12})$-aryl which is optionally up to trisubstituted by identical or different radicals selected from the group consisting of $(C_1-C_6)$-alkyl, $(C_1-C_6)$-alkoxy, $(C_1-C_6)$-haloalkyl and $(C_1-C_6)$-haloalkoxy,
11) heteroaryl which has up to 10 carbon atoms and which is optionally substituted as described under 10.,
12) $(C_6-C_{12})$-aryl-$(C_1-C_4)$-alkyl which is optionally substituted in the aryl moiety as described under 10.,
13) heteroaryl-$(C_1-C_4)$-alkyl which has up to 10 carbon atoms in the heteroaryl moiety and is optionally substituted in this moiety as described under 10.,
14) $(C_1-C_6)$-alkoxy,
15) $(C_2-C_6)$-alkenyloxy,
16) $(C_2-C_6)$-alkynyloxy,
17) $(C_3-C_8)$-cycloalkyloxy which is optionally substituted as described under 4.,
18) $(C_1-C_6)$-alkoxy, $(C_1-C_4)$-alkoxy,
19) $(C_6-C_{12})$-aryloxy which is optionally substituted as described under 10.,
20) heteroaryloxy which has up to 10 carbon atoms and which is optionally substituted as described under 10.,
21) $(C_1-C_6)$-haloalkoxy,
22) $(C_2-C_6)$-haloalkenyloxy,
23) $(C_2-C_6)$-haloalkynyloxy,
24) —O—N=CR'$_2$ in which R' radicals are identical or different radicals selected from the group consisting of hydrogen, $(C_1-C_6)$-alkyl, $(C_3-C_8)$-cycloalkyl and $(C_6-C_{12})$-aryl,
25) $(C_1-C_6)$-alkylamino,
26) di-$(C_1-C_6)$-alkylamino,
27) $(C_3-C_8)$-cycloalkylamino which is optionally substituted as described under 4.,
28) $(C_6-C_{12})$-arylamino which is optionally substituted as described under I.b) 10.,
29) heteroarylamino which has up to 10 carbon atoms and is optionally substituted as described under 10.,
30) $(C_1-C_6)$-alkylmercapto,
31) $(C_6-C_{12})$-arylmercapto,
32) heteroarylmercapto having up to 10 carbon atoms,
33) $(C_1-C_6)$-alkylsulfinyl,
34) $(C_6-C_{12})$-arylsulfinyl,
35) heteroarylsulfinyl having up to 10 carbon atoms,
36) $(C_1-C_6)$-alkylsulfonyl,
37) $(C_6-C_{12})$-arylsulfonyl,
38) heteroarylsulfonyl having up to 10 carbon atoms,
39) nitro,
40) cyano,
41) cyano-$(C_1-C_6)$-alkyl,
42) $(C_1-C_6)$-alkoxycarbonyl,
43) $(C_6-C_{12})$-aryloxycarbonyl and
44) heteroaryloxycarbonyl having up to 10 carbon atoms in the heteroaryl moiety, or
45) a) two of the substituents represent methylenedioxy,
b) the methylenedioxy group optionally being substituted by one or two identical or different radicals selected from the group consisting of halogen and $(C_1-C_4)$-alkyl;

X is O, S or $MR^3$;
$R^3$ is hydrogen,
 $(C_1-C_6)$-alkyl,
 $(C_2-C_6)$-alkenyl,
 $(C_2-C_6)$-alkynyl
 $(C_3-C_8)$-cycloalkyl which is optionally substituted by up to 6 identical or different radicals selected from the group consisting of halogen and $(C_1-C_4)$-alkyl,
 $(C_1-C_6)$-haloalkyl,
 $(C_2-C_6)$-haloalkenyl,
 $(C_2-C_6)$-haloalkynyl
 $(C_1-C_6)$-alkoxy-$(C_1-C_6)$-alkyl,
 $(C_6-C_{12})$-aryl-$(C_1-C_4)$-alkyl,
 heteroaryl-$(C_1-C_4)$-alkyl having up to 10 carbon atoms in the heteroaryl moiety,
 cyano-$(C_1-C_6)$-alkyl,
 $(C_1-C_6)$-alkoxycarbonyl,
 $(C_6-C_{12})$-aryloxycarbonyl or
 heteroaryloxycarbonyl having up to 10 carbon atoms;
$Ar^2$ is

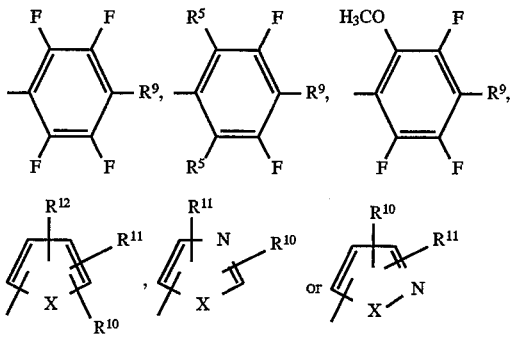

X is as defined above;
X' is $NR^3$ and $R^3$ is as defined above;
$R^5$ is hydrogen, methyl or methoxy;
$R^9$ is $(C_1-C_6)$-alkyl, $(C_1-C_6)$-alkoxy, $(C_1-C_6)$-halogenalkyl or $(C_1-C_{10})$-halogenalkoxy; and
$R^{10}$, $R^{11}$ and $R^{12}$ are identical or different and are hydrogen or are one of the substituents defined above under 1.–45., or $Ar^2$ if not encompassed by the preceding definitions, additionally denotes

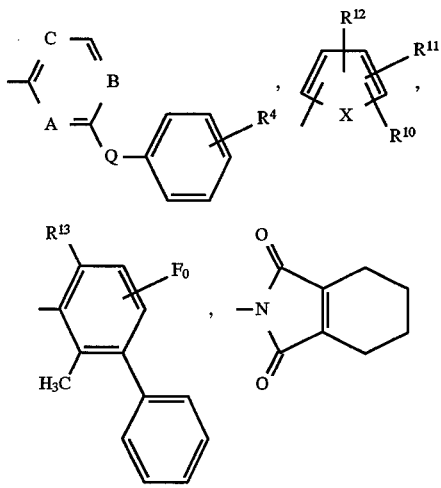

77

-continued

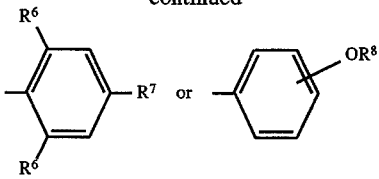

one of the groups A, B and C is nitrogen and the remaining two groups are identical or different and are CH or C-Hal;

Q is O, S, NH or $CH_2$, $R^4$ is hydrogen, halogen, O—$CH_2$—CH=$CH_2$ or O—$CH_2$—C≡CH, Hal is halogen, X" is O or S, $R^{10}$, $R^{11}$ and $R^{12}$ are as defined above $R^{13}$ is hydrogen, fluoro or methyl, o is 0, 1 or 2, $R^6$ is hydrogen, fluoro or ($C_1$-$C_6$)-alkyl, $R^7$ is halogenophenoxy, halogenobenzyl, O—$CH_2$—CH=$CH_2$, O—$CH_2$—C≡CH, $CH_2$—CH=$CH_2$ or $CH_2$—C≡CH and $R^8$ is ($C_2$-$C_6$)-alkenyl or ($C_2$-$C_6$)-halogenalkyl; and in case $Ar^1$ is one of the heteroaryl groups selected from the group consisting of benzofuryl, benzothienyl, pyridyl, pyrimidinyl, pyrazinyl,

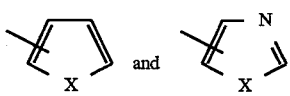

in which X is as defined above, which heteroaryl group is optionally substituted as defined above for $Ar^1$, then $Ar^2$, if not encompassed by the preceding definitions additionally denotes

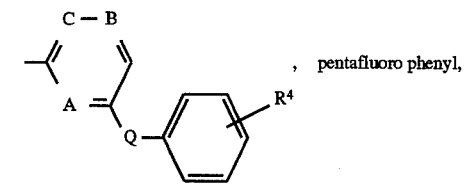

, pentafluoro phenyl,

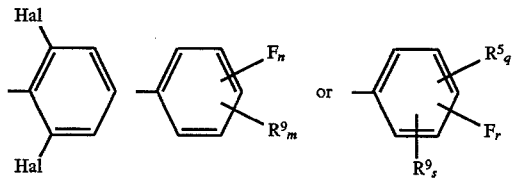

A, B and C are identical or different and are N, CH or C-Hal,

Q, $R^4$, Hal and $R^9$ are as defined above, m and n are identical or different and are in each case 1, 2, 3 or 4, m+n is 5, $R^5$ is as defined above, q, r, s are identical or different and are in each case 1, 2 or 3 and q+r+s is 5.

2. A compound as claimed in claim 1 or a salt thereof, in which

78

$Ar^1$ is a radical of the formula

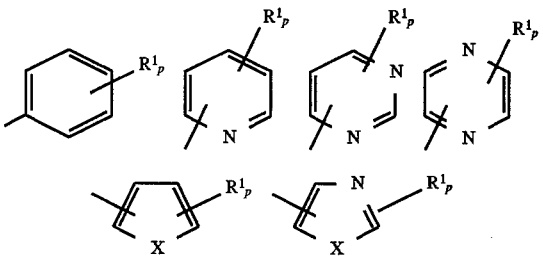

X is as defined in claim 1,

P is an integer from 0 to 5, and $R^1$ radicals are identical or different and are halogen, ($C_1$-$C_6$)-alkyl, ($C_2$-$C_6$)-alkenyl, ($C_2$-$C_6$)-alkynyl, ($C_3$-$C_8$)-cycloalkyl which is optionally substituted by up to 6 identical or different radicals selected from the group consisting of halogen and ($C_1$-$C_4$)-alkyl, ($C_1$-$C_6$)-haloalkyl, ($C_2$-$C_6$)-haloalkenyl, ($C_2$-$C_6$)-haloalkynyl ($C_1$-$C_6$)-alkoxy-($C_1$-$C_6$)-alkyl, ($C_6$-$C_{12}$)-aryl which is optionally up to tri-substituted by identical or different radicals selected from the group consisting of halogen, ($C_1$-$C_6$)-alkyl, ($C_1$-$C_6$)-alkoxy, ($C_1$-$C_6$)-haloalkyl, and ($C_1$-$C_6$)-haloalkoxy, heteroaryl which has up to 10 carbon atoms and which is optionally substituted like the above-mentioned aryl, ($C_6$-$C_{12}$)-aryl-($C_1$-$C_4$)-alkyl which is optionally substituted in the aryl moiety like the above-mentioned aryl, heteroaryl-($C_1$-$C_6$)-alkyl which has up to 10 carbon atoms in the heteroaryl moiety and is optionally substituted in this moiety like the above-mentioned aryl, ($C_1$-$C_6$)-alkoxy, ($C_2$-$C_6$)-alkenyloxy, ($C_2$-$C_6$)-alkynyloxy, ($C_3$-$C_8$)-cycloalkyloxy, ($C_1$-$C_6$)-alkoxy-($C_1$-$C_6$)-alkoxy, ($C_6$-$C_{12}$)-aryloxy which is optionally substituted like the above-mentioned aryl, heteroaryloxy which has up to 10 carbon atoms and which is optionally substituted like the above-mentioned aryl, ($C_1$-$C_6$)-haloalkoxy, ($C_2$-$C_6$)-haloalkenyloxy, ($C_2$-$C_6$)-haloalkynyloxy or —O—N=$CR'_2$ in which R' radicals are identical or different radicals selected from the group consisting of hydrogen, ($C_1$-$C_6$)-alkyl, ($C_3$-$C_8$)-cycloalkyl and ($C_6$-$C_{12}$)-aryl, or two of the radicals $R^1$ are methylenedioxy which is optionally substituted as described under 45.b).

3. A compound as claimed in claim 2 or a salt thereof, in which $R^1$ is ($C_1$-$C_6$)-alkyl, ($C_2$-$C_6$)-alkenyl, ($C_2$-$C_6$)-alkynyl, ($C_3$-$C_8$)-cycloalkyl, halogen, ($C_1$-$C_6$)-haloalkyl, ($C_2$-$C_6$)-haloalkenyl, ($C_2$-$C_6$)-haloalkynyl, heteroaryl having up to 10 carbon atoms or ($C_6$-$C_{12}$)-aryl, optionally substituted as described in claim 2, ($C_1$-$C_6$)-alkoxy, ($C_2$-$C_6$)-alkenyloxy, ($C_2$-$C_6$)-alkynyloxy, ($C_3$-$C_8$)-cycloalkyloxy, heteroaryloxy having up to 10 carbon atoms or ($C_6$-$C_{12}$)- aryloxy, optionally substituted as described in claim 2, $(C_1-C_6)$-alkoxy-$(C_1-C_6)$-alkyl, $(C_1-C_6)$-alkoxy-$(C_1-C_6)$-alkoxy, $(C_1-C_6)$-haloalkoxy, $(C_2-C_6)$-haloalkenyloxy or $(C_2-C_6)$-haloalkynyloxy, or two of the radicals $R^1$ are methylenedioxy which is optionally substituted as described under 45. b).

4. A compound as claimed in claim 2 or a salt thereof, in which $R^1$ is $(C_1-C_6)$-haloalkoxy, $(C_1-C_6)$-alkoxy, fluorine, chlorine, bromine, $(C_1-C_6)$-alkyl, $(C_1-C_6)$-haloalkenyloxy, $(C_2-C_6)$-haloalkenyloxy, $(C_1-C_6)$-haloalkyl, $(C_2-C_6)$-haloalkenyl, $(C_2-C_6)$-haloalkynyl.

5. A compound as claimed in claim 2 or a salt thereof, in which $Ar^1$ is

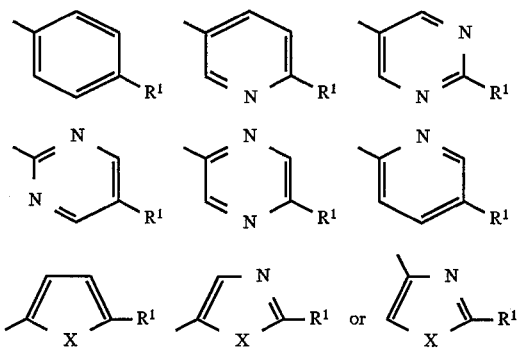

and $R^1$ and X are as defined in claim 2.

6. A compound as claimed in claim 1 or a salt thereof, in which R is trifluoromethyl and $Ar^2$ is

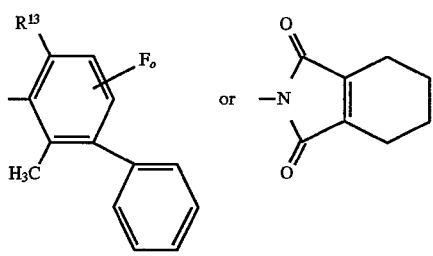

7. A compound as claimed in claim 1 or a salt thereof, in which $Ar^2$ is

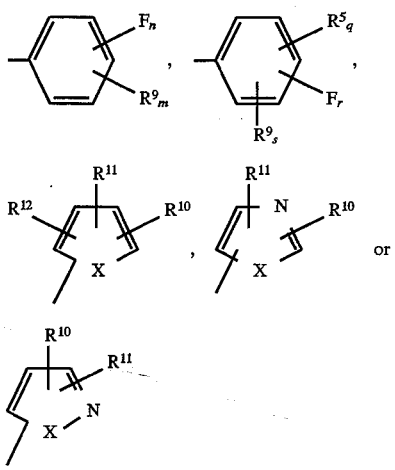

8. A compound as claimed in claim 1 or a salt thereof, in which Q is o or $CH_2$.

9. A compound of the formula

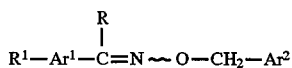

in the form of the syn or the anti-compound or a mixture of these or a salt thereof,
in which
$R^1$ is 4-$OCF_3$;
$Ar^1$ is phenyl;
R is $CF_3$; and
$Ar^2$ is 2-methyl-3-phenylphenyl.

10. A process for the preparation of a compound as claimed in claim 1, which comprises
a) reacting a compound of the formula II

in which $Ar^1$ and R are as defined in formula I and M is hydrogen or an alkali metal atom, with a compound of the formula III

in which $Ar^2$ is as defined in formula I and X is a leaving group; if M is hydrogen, in the presence of a suitable base; or
b) reacting a compound of the formula IV

with a compound of the formula V or a salt thereof

if appropriate in the presence of a base, and if appropriate, converting the resulting compound of the formula I into a salt thereof.

11. An insecticidal agent which comprises an insecticidally effective amount of at least one compound as claimed in claim 1 together with the customary additives or auxiliaries.

12. A method for controlling insect pests, in which an effective amount of a compound as claimed in claim 1 is applied to these insect pests or the plants, areas or substrates infested with them.

13. An acaricidal agent which comprises an acaricidally effective amount of at least one compound as claimed in claim 1 together with the customary additives or auxiliaries.

14. A method for controlling Acarina, in which an effective amount of a compound as claimed in claim 1 is applied to these Acarina or the plants, areas or substrates infested with them.

15. An nematical agent which comprises a nematicidally effective amount of at least one compound as claimed in claim 1 together with the customary additives or auxiliaries.

16. A method for controlling nematodes, in which an effective amount of a compound as claimed in claim 1 is applied to these nematodes or the plants, areas or substrates infested with them.

* * * * *